(12) United States Patent
Murphy et al.

(10) Patent No.: US 10,519,230 B2
(45) Date of Patent: Dec. 31, 2019

(54) NUCLEIC ACIDS ENCODING IL-33 ANTIBODIES

(71) Applicant: Regeneron Pharmaceuticals, Inc., Tarrytown, NY (US)

(72) Inventors: Andrew J. Murphy, Croton-on-Hudson, NY (US); Nicholas J. Papadopoulos, LaGrangeville, NY (US); Jamie M. Orengo, Cortlandt Manor, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 33 days.

(21) Appl. No.: 15/979,187

(22) Filed: May 14, 2018

(65) Prior Publication Data

US 2018/0251542 A1 Sep. 6, 2018

Related U.S. Application Data

(62) Division of application No. 15/248,348, filed on Aug. 26, 2016, now Pat. No. 10,000,564, which is a division of application No. 14/205,512, filed on Mar. 12, 2014, now Pat. No. 9,453,072.

(60) Provisional application No. 61/819,018, filed on May 3, 2013, provisional application No. 61/778,687, filed on Mar. 13, 2013.

(51) Int. Cl.

| *C12N 5/10* | (2006.01) |
| *C12N 15/24* | (2006.01) |
| *C07K 16/24* | (2006.01) |
| *A61K 45/06* | (2006.01) |
| *A61K 39/395* | (2006.01) |
| *A61K 39/00* | (2006.01) |

(52) U.S. Cl.
CPC ........ *C07K 16/244* (2013.01); *A61K 39/3955* (2013.01); *A61K 45/06* (2013.01); *A61K 2039/505* (2013.01); *C07K 2317/21* (2013.01); *C07K 2317/33* (2013.01); *C07K 2317/56* (2013.01); *C07K 2317/76* (2013.01); *C07K 2317/92* (2013.01); *C07K 2317/94* (2013.01)

(58) Field of Classification Search
CPC .............................. C12N 15/00; C12N 15/09
See application file for complete search history.

(56) References Cited

U.S. PATENT DOCUMENTS

| 5,500,362 | A | 3/1996 | Robinson et al. |
| 5,576,191 | A | 11/1996 | Gayle et al. |
| 5,821,337 | A | 10/1998 | Carter et al. |
| 8,119,771 | B2 | 2/2012 | Martin |
| 8,187,596 | B1 | 5/2012 | Chackerian et al. |
| 9,453,072 | B2 | 9/2016 | Murphy et al. |
| 9,637,535 | B2 | 5/2017 | Murphy et al. |
| 1,000,056 | A1 | 6/2018 | Murphy et al. |
| 1,001,164 | A1 | 7/2018 | Murphy et al. |
| 2007/0042978 | A1 | 2/2007 | Girard et al. |
| 2007/0087411 | A1 | 4/2007 | Sharma et al. |
| 2009/0041718 | A1 | 2/2009 | Schmitz et al. |
| 2009/0304699 | A1 | 12/2009 | Amatucci et al. |
| 2010/0260705 | A1 | 10/2010 | Martin |
| 2010/0260770 | A1 | 10/2010 | Coyle |
| 2012/0207752 | A1 | 8/2012 | Chackerian et al. |
| 2012/0263709 | A1 | 10/2012 | Rankin et al. |
| 2013/0287777 | A1 | 10/2013 | Duffy et al. |
| 2013/0336980 | A1 | 12/2013 | Duffy et al. |
| 2014/0004107 | A1 | 1/2014 | Smith et al. |
| 2014/0140954 | A1 | 5/2014 | Schmitz et al. |
| 2016/0289322 | A1 | 10/2016 | Fujino et al. |
| 2016/0362487 | A1 | 12/2016 | Murphy et al. |

FOREIGN PATENT DOCUMENTS

| EP | 2069784 A1 | 6/2009 |
| EP | 2152740 A1 | 2/2010 |
| EP | 1725261 B1 | 1/2011 |
| EP | 2283860 A2 | 2/2011 |
| EP | 2475388 A1 | 7/2012 |
| WO | 05/079844 A2 | 9/2005 |
| WO | 08/132709 A1 | 11/2008 |
| WO | 08/144610 A1 | 11/2008 |
| WO | 09/053098 A1 | 4/2009 |
| WO | 11/031600 A1 | 3/2011 |

(Continued)

OTHER PUBLICATIONS

"AnaptysBio Announces Development of Novel Anti-IL33 Therapeutic Antibody," AnaptysBio, Inc., 1 page, (2014). [Retrieved from the Internet Jul. 3, 2014: <URL: http://www.anaptysbio.com/anti-1133/>]. (Author Unknown).

(Continued)

*Primary Examiner* — Prema M Mertz

(74) *Attorney, Agent, or Firm* — Schwabe, Williamson & Wyatt PC; Veronica Mallon

(57) ABSTRACT

The present invention provides antibodies that bind to interleukin-33 (IL-33) and methods of using the same. The invention includes antibodies that inhibit or attenuate IL-33-mediated signaling. The antibodies of the invention may function to block the interaction between IL-33 and ST2. Alternatively, certain antibodies of the invention inhibit or attenuate IL-33-mediated signaling without blocking the IL-33/ST2 interaction. According to certain embodiments of the invention, the antibodies are fully human antibodies that bind to human IL-33 with high affinity. The antibodies of the invention are useful for the treatment of diseases and disorders associated with IL-33 signaling and/or IL-33 cellular expression, such as inflammatory diseases, or allergic diseases.

20 Claims, 2 Drawing Sheets

Specification includes a Sequence Listing.

(56) References Cited

FOREIGN PATENT DOCUMENTS

| WO | 14/152195 A1 | 9/2014 |
|---|---|---|
| WO | 14/164959 A2 | 10/2014 |
| WO | 15/099175 A1 | 7/2015 |
| WO | 15/106080 A2 | 7/2015 |

OTHER PUBLICATIONS

Ali et al., "Caspase 3 inactivates biologically active full length interleukin-33 as a classical cytokine but does not prohibit nuclear translocation," Biochemical and Biophysical Research Communications, 391(3):1512-1516, (2010).
Ali, "Characterization of Interleukin-33 and the IL-33 Receptor Complex," Dissertation, pp. 1-126, (2009).
Alignment between Human IL-33 and Cynomolgus Monkey IL-33 with 93.704% identity. 26; Sep. 2017.
GenBank: Accession No. AEP47229, "Sequence 67 from U.S. Pat. No. 8,008,076," Sep. 30, 2011. [Retrieved from the Internet Mar. 28, 2017: <URL: http://www.ncbi.nlm.nih.gov/protein/AEP47229>].
GenBank: Accession No. AEP47235, "Sequence 111 from U.S. Pat. No. 8,008,076," Sep. 30, 2011. [Retrieved from the Internet Mar. 28, 2017: <URL: http://www.ncbi.nlm.nih.gov/protein/AEP47235>].
GenBank: Accession No. AFD49488, "Sequence 28 from U.S. Pat. No. 8,129,503," Mar. 14, 2012. [Retrieved from the Internet Mar. 28, 2017: <URL: http://www.ncbi.nlm.nih.gov/protein/AFD49488>].
GenBank: Accession No. BAC05421, "unnamed protein product [*Homo sapiens*]," Sep. 14, 2016. [Retrieved from the Internet Mar. 28, 2017: <URL: http://www.ncbi.nlm.nih.gov/protein/BAC05421>].
Hayakawa et al., "Soluble ST2 Blocks Interleukin-33 Signaling in Allergic Airway Inflammation," Journal of Biological Chemistry, 282(36):26369-26380, (2007).
Hong et al., "The inhibitory function of Fc-ST2 depends on cell type; IL-1RAcP and ST2 are necessary but insufficient for IL-33 activity," Immunol Res, 56:122-130, (2013).
Hueber et al., "IL-33 induces skin inflammation with mast cell and neutrophil activation," Eur. J. Immunol, 41: 2229-2237, doi: 10.1002/eji.201041360, (2011).
Kim et al., "Beneficial effect of anti-interleukin-33 on the murine model of allergic inflammation of the lower airway," J Asthma., 49(7):738-743, doi: 10.3109/02770903.2012.702841, (2012).
Kim et al., "Anti-IL-33 antibody has a therapeutic effect in a murine model of allergic rhinitis," Allergy, 8 pages, doi: 10.1111/j.1398-9995.2011.02735.x., (2011).
Li et al., "IL-33 blockade suppresses the development of experimental autoimmune encephalomyelitis in C57BL/6 mice," Journal of Neuroimmunology, 247: 25-31, (2012).
Liew et al., "Disease-associated functions: of1L-33: the new kid in the IL-1 family," Nature Reviews, Immunology, 10(2):103-110, (2010).
Liew et al., "Interleukin-33 in Health and Disease," Nature Reviews—Immunology, vol. 16; Nov. 2016; pp. 676-689. [Retrieved from the Internet at <www.nature.com/nri>].
Liu et al., "Anti-Il-33 antibody treatment inhibits airway inflammation in a murine model of allergic asthma," Biomedical and Biophysical Research Communications, vol. 386: (2009) pp. 181-185.
Lohning et al., "T1/ST2 is preferentially expressed on murine Th2 cells, independent of interleukin 4, interleukin 5, and interleukin 10, and important for Th2 effector function," Proc. Natl. Acad. Sci. USA, 95(12):6930-6935, (1998).

Miller, "Role of IL-33 in inflammation and disease," Journal of Inflammation, vol. 8:22, (2011). Available on the Internet at <http://journal-inflammation.com/content/8/1/22>.
Oshikawa et al., "Acute eosinophilic pneumonia with increased soluble ST2 in serum and bronchoalveolar lavage fluid," Respiratory Medicine, 95:532-533, (2001).
Oshikawa et al., "Elevated Soluble ST2 Protein Levels in Sera of Patients with Asthma with an Acute Exacerbation," Am J Respir Crit Care Med, 164:277-281, (2001).
Palmer et al., "Interleukin-33 biology with potential insights into human diseases," Nature Reviews, Rheumatology, 7(No):321-329, (2011).
Palmer et al., "The IL-1 receptor accessory protein (AcP) is required for IL-33 signaling and soluble AcP enhances the ability of soluble ST2 to inhibit IL-33," Cytokine, 42(3):358-364, (2008).
Pastorelli et al., "Epithelial-derived IL-33 and its receptor ST2 are dysregulated in ulcerative colitis and in experimental Th1/Th2 driven enteritis," PNAS, 107(17):8017-8022, doi: 10.1073/pnas.0912678107, (2010).
Schmitz et al., "IL-33, an Interleukin-1-like Cytokine that Signals via the IL-1 Receptor-Related Protein ST2 and Induces T Helper Type 2-Associated Cytokines," Immunity, 23:479-490, (2005).
Stevenson et al., "Moving towards a new generation of animal models for asthma and COPD with improved clinical relevance," Pharmacol Ther., 130(2):93-105, Abstract Only, doi: 10.1016/j.pharmthera.2010.10.008, (2011). Epub Nov. 11, 2010.
Stolarski et al., "IL-33 Exacerbates Eosinophil-Mediated Airway Inflammation," J Immunol, 185:3472-3480, doi: 10.4049/jimmunol.1000730, (2010).
Tajima et al., "The Increase in Serum Soluble ST2 Protein Upon Acute Exacerbation of Idiopathic Pulmonary Fibrosis," Chest, 124:1206-1214, (2003).
U.S. Appl. No. 14/205,512, Notice of Allowance dated May 27, 2016.
U.S. Appl. No. 14/205,512, Requirement for Restriction/Election dated Mar. 15, 2016.
U.S. Appl. No. 14/210,599, Non-Final Office Action dated Sep. 25, 2015.
U.S. Appl. No. 14/210,599, Non-Final Office Action dated May 23, 2016.
U.S. Appl. No. 14/210,599, Notice of Allowance dated Dec. 19, 2016.
U.S. Appl. No. 14/210,599, Requirement for Restriction/Election dated Jun. 29, 2015.
U.S. Appl. No. 15/248,348, Notice of Allowance dated Jan. 17, 2018.
U.S. Appl. No. 15/248,348, Requirement for Restriction/Election dated Sep. 14, 2017.
U.S. Appl. No. 15/463,910, Notice of Allowance dated Feb. 26, 2018.
Uniprot: "Alignment human and cynomolgus monkey IL-33", Aug. 3, 2017 (Aug. 3, 2017), XP055396027, retrieved from the Internet: <http://www.uniprot.org/align/A20170803AAFB7E4D2F1D05654627429E83DA5CCEC7E4343> [retrieved on Aug. 3, 2017].
WIPO Application No. PCT/US2014/023930, PCT International Preliminary Report on Patentability dated Sep. 24, 2015.
WIPO Application No. PCT/US2014/023930, PCT International Search Report and Written Opinion of the International Searching Authority dated Dec. 12, 2014.
WIPO Application No. PCT/US2014/027058, PCT International Preliminary Report on Patentability dated Sep. 24, 2015.
WIPO Application No. PCT/US2014/027058, PCT International Search Report and Written Opinion of the International Searching Authority dated Jun. 26, 2014.

NUCLEIC ACIDS ENCODING IL-33 ANTIBODIES

CROSS-REFERENCE TO RELATED APPLICATIONS

This application is a division of U.S. application Ser. No. 15/248,348, filed Aug. 26, 2016, which is a division of U.S. application Ser. No. 14/205,512, filed Mar. 12, 2014, now U.S. Pat. No. 9,453,072, which claims the benefit under 35 USC § 119(e) of U.S. Provisional Application Nos. 61/778,687, filed Mar. 13, 2013, and 61/819,018, filed May 3, 2013, each of which is herein specifically incorporated by reference in its entirety.

SEQUENCE LISTING

This application incorporates by reference the Sequence Listing submitted in Computer Readable Form as file 1850US03-Sequence.txt, created on May 14, 2018 and containing 111,015 bytes.

FIELD OF THE INVENTION

The present invention relates to antibodies, and antigen-binding fragments thereof, which are specific for human IL-33, and methods of use thereof.

BACKGROUND

Interleukin-33 (IL-33) is a ligand for ST2, a toll-like/interleukin-1 receptor super-family member that associates with an accessory protein, IL-1RAcP (for reviews, see, e.g., Kakkar and Lee, *Nature Reviews—Drug Discovery* 7(10): 827-840 (2008), Schmitz et al., Immunity 23:479-490 (2005); Liew et al., *Nature Reviews—Immunology* 10:103-110 (2010); US 2010/0260770; US 2009/0041718). Upon activation of ST2/IL-1RAcP by IL-33, a signaling cascade is triggered through downstream molecules such as MyD88 (myeloid differentiation factor 88) and TRAF6 (TNF receptor associated factor 6), leading to activation of NFκB (nuclear factor-κB), among others. IL-33 signaling has been implicated as a factor in a variety of diseases and disorders. (Liew et al., *Nature Reviews—Immunology* 10:103-110 (2010)).

BRIEF SUMMARY OF THE INVENTION

The present invention provides antibodies that bind human interleukin-33 ("IL-33"). The antibodies of the invention are useful, inter alia, for inhibiting IL-33-mediated signaling and for treating diseases and disorders caused by or related to IL-33 activity and/or signaling.

The antibodies of the invention can be full-length (for example, an IgG1 or IgG4 antibody) or may comprise only an antigen-binding portion (for example, a Fab, F(ab')$_2$ or scFv fragment), and may be modified to affect functionality, e.g., to eliminate residual effector functions (Reddy et al., 2000, J. Immunol. 164:1925-1933).

In one embodiment, the antibodies that bind specifically to human interleukin-33 are isolated fully human monoclonal antibodies.

In one embodiment, the antibodies that bind specifically to human interleukin-33, or antigen-binding fragments thereof inhibit or attenuate IL-33-mediated signaling.

In one embodiment, the antibodies that bind specifically to human interleukin-33, or antigen-binding fragments thereof block the interaction of IL-33 and ST2.

In one embodiment, the antibodies that bind specifically to human interleukin-33, or antigen-binding fragments thereof block the interaction of IL-33 and ST2 with an IC$_{50}$ value of less than about 10 nM, or blocks greater than about 50% of the interaction of IL-33 and ST2 as measured in an in vitro receptor/ligand binding assay at 25° C.

In one embodiment, the antibodies that bind specifically to human interleukin-33, or antigen-binding fragments thereof do not block, or only partially block the interaction of IL-33 and ST2.

In one embodiment, the antibodies that bind specifically to human interleukin-33, or antigen-binding fragments thereof bind human IL-33 with a binding dissociation equilibrium constant (K$_D$) of less than about 1 nM as measured in a surface plasmon resonance assay at 37° C.

In one embodiment, the antibodies that bind specifically to human interleukin-33, or antigen-binding fragments thereof bind human IL-33 with a dissociative half-life (t½) of greater than about 8 minutes as measured in a surface plasmon resonance assay at 37° C.

In one embodiment, the antibodies that bind specifically to human interleukin-33, or antigen-binding fragments thereof inhibit IL-33-mediated degranulation of human basophils.

In one embodiment, the antibodies that bind specifically to human interleukin-33, or antigen-binding fragments thereof inhibit IL-33-mediated degranulation of human basophils with an IC$_{50}$ of less than about 600 pM as measured in an in vitro basophil activation test (BAT).

In one embodiment, the antibodies that bind specifically to human interleukin-33, or antigen-binding fragments thereof inhibit IL-33-mediated IFN-gamma production from human PBMCs.

In one embodiment, the antibodies that bind specifically to human interleukin-33, or antigen-binding fragments thereof inhibit IL-33-mediated IFN-gamma production from human PBMCs with an IC$_{50}$ of less than about 25 nM as measured in an in vitro PBMC IFN-gamma production assay.

In one embodiment, the antibodies that bind specifically to human interleukin-33, or antigen-binding fragments thereof inhibit IL-33-mediated IFN-gamma production from human PBMCs with an IC$_{50}$ of less than about 3 nM as measured in an in vitro PBMC IFN-gamma production assay.

In one embodiment, the antibodies that bind specifically to human interleukin-33, or antigen-binding fragments thereof inhibit IL-33-mediated IFN-gamma production from human PBMCs with an IC$_{50}$ of less than about 0.5 nM as measured in an in vitro PBMC IFN-gamma production assay.

In one embodiment, the antibodies that bind specifically to human interleukin-33, or antigen-binding fragments thereof reduce the frequency of CD4+ T cells, eosinophils and ILC2 cells in the lungs when administered to an animal model of allergen-induced lung inflammation.

In one embodiment, the antibodies that bind specifically to human interleukin-33, or antigen-binding fragments thereof reduces the level of IL-4 and IL-5 in the lungs when administered to an animal model of allergen-induced lung inflammation.

In one embodiment, the antibodies that bind specifically to human interleukin-33, or antigen-binding fragments thereof, when administered to an animal model of allergen-induced lung inflammation, result in at least a 4 fold reduction of IL-4 levels and/or at least a 5 fold reduction in IL-5 levels when compared to allergen-challenged animals receiving an isotype control antibody.

The present invention provides antibodies, or antigen-binding fragments thereof comprising a heavy chain variable region (HCVR) having an amino acid sequence selected from the group consisting of SEQ ID NO: 2, 18, 34, 50, 66, 82, 98, 114, 130, 146, 162, 178, 194, 210, 226, 242, 258, 274, 290, and 308, or a substantially similar sequence thereof having at least 90%, at least 95%, at least 98% or at least 99% sequence identity.

The present invention also provides an antibody or antigen-binding fragment of an antibody comprising a light chain variable region (LCVR) having an amino acid sequence selected from the group consisting of SEQ ID NO: 10, 26, 42, 58, 74, 90, 106, 122, 138, 154, 170, 186, 202, 218, 234, 250, 266, 282, 298, and 316, or a substantially similar sequence thereof having at least 90%, at least 95%, at least 98% or at least 99% sequence identity.

The present invention also provides an antibody or antigen-binding fragment thereof comprising a HCVR and LCVR (HCVR/LCVR) sequence pair selected from the group consisting of SEQ ID NO: 2/10, 18/26, 34/42, 50/58, 66/74, 82/90, 98/106, 114/122, 130/138, 146/154, 162/170, 178/186, 194/202, 210/218, 226/234, 242/250, 258/266, 274/282, 290/298, and 308/316.

The present invention also provides an antibody or antigen-binding fragment of an antibody comprising a heavy chain CDR3 (HCDR3) domain having an amino acid sequence selected from the group consisting of SEQ ID NO: 8, 24, 40, 56, 72, 88, 104, 120, 136, 152, 168, 184, 200, 216, 232, 248, 264, 280, 296, and 314, or a substantially similar sequence thereof having at least 90%, at least 95%, at least 98% or at least 99% sequence identity; and a light chain CDR3 (LCDR3) domain having an amino acid sequence selected from the group consisting of SEQ ID NO: 16, 32, 48, 64, 80, 96, 112, 128, 144, 160, 176, 192, 208, 224, 240, 256, 272, 288, 304, and 322, or a substantially similar sequence thereof having at least 90%, at least 95%, at least 98% or at least 99% sequence identity.

In certain embodiments, the antibody or antigen-binding portion of an antibody comprises a HCDR3/LCDR3 amino acid sequence pair selected from the group consisting of SEQ ID NO: 8/16, 24/32, 40/48, 56/64, 72/80, 88/96, 104/112, 120/128, 136/144, 152/160, 168/176, 184/192, 200/208, 216/224, 232/240, 248/256, 264/272, 280/288, 296/304 and 314/322.

The present invention also provides an antibody or fragment thereof further comprising a heavy chain CDR1 (HCDR1) domain having an amino acid sequence selected from the group consisting of SEQ ID NO: 4, 20, 36, 52, 68, 84, 100, 116, 132, 148, 164, 180, 196, 212, 228, 244, 260, 276, 292, and 310, or a substantially similar sequence thereof having at least 90%, at least 95%, at least 98% or at least 99% sequence identity; a heavy chain CDR2 (HCDR2) domain having an amino acid sequence selected from the group consisting of SEQ ID NO: 6, 22, 38, 54, 70, 86, 102, 118, 134, 150, 166, 182, 198, 214, 230, 246, 262, 278, 294, and 312, or a substantially similar sequence thereof having at least 90%, at least 95%, at least 98% or at least 99% sequence identity; a light chain CDR1 (LCDR1) domain having an amino acid sequence selected from the group consisting of SEQ ID NO: 12, 28, 44, 60, 76, 92, 108, 124, 140, 156, 172, 188, 204, 220, 236, 252, 268, 284, 300, and 318, or a substantially similar sequence thereof having at least 90%, at least 95%, at least 98% or at least 99% sequence identity; and a light chain CDR2 (LCDR2) domain having an amino acid sequence selected from the group consisting of SEQ ID NO: 14, 30, 46, 62, 78, 94, 110, 126, 142, 158, 174, 190, 206, 222, 238, 254, 270, 286, 302, and 320, or a substantially similar sequence thereof having at least 90%, at least 95%, at least 98% or at least 99% sequence identity.

Certain non-limiting, exemplary antibodies and antigen-binding fragments of the invention comprise HCDR1-HCDR2-HCDR3-LCDR1-LCDR2-LCDR3 domains, respectively, having the amino acid sequences selected from the group consisting of: SEQ ID NOs: 4-6-8-12-14-16 (e.g. H1M9559N); 20-22-24-28-30-32 (e.g. H1M9566N); 36-38-40-44-46-48 (e.g. H1M9568N); 52-54-56-60-62-64 (e.g. H4H9629P); 68-70-72-76-78-80 (e.g. H4H9633P); 84-86-88-92-94-96 (e.g. H4H9640P); 100-102-104-108-110-112 (e.g. H4H9659P); 116-118-120-124-126-128 (e.g. H4H9660P); 132-134-136-140-142-144 (e.g. H4H9662P); 148-150-152-156-158-160 (e.g., H4H9663P); 164-166-168-172-174-176 (e.g. H4H9664P); 180-182-184-188-190-192 (e.g., H4H9665P); 196-198-200-204-206-208 (e.g. H4H9666P); 212-214-216-220-222-224 (e.g. H4H9667P); 228-230-232-236-238-240 (e.g. H4H9670P); 244-246-248-252-254-256 (e.g. H4H9671P); 260-262-264-268-270-272 (e.g. H4H9672P); 276-278-280-284-286-288 (e.g. H4H9675P); 292-294-296-300-302-304 (e.g. H4H9676P); and 310-312-314-318-320-322 (H1M9565N).

In a related embodiment, the invention includes an antibody or antigen-binding fragment of an antibody which specifically binds IL-33, wherein the antibody or fragment comprises the heavy and light chain CDR domains contained within heavy and light chain variable region (HCVR/LCVR) sequences selected from the group consisting of SEQ ID NO: 2/10, 18/26, 34/42, 50/58, 66/74, 82/90, 98/106, 114/122, 130/138, 146/154, 162/170, 178/186, 194/202, 210/218, 226/234, 242/250, 258/266, 274/282, 290/298, and 308/316. Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., *J. Mol. Biol.* 273:927-948 (1997); and Martin et al., *Proc. Natl. Acad. Sci. USA* 86:9268-9272 (1989). Public databases are also available for identifying CDR sequences within an antibody.

In another aspect, the invention provides nucleic acid molecules encoding anti-IL-33 antibodies or antigen-binding fragments thereof. Recombinant expression vectors carrying the nucleic acids of the invention, and host cells into which such vectors have been introduced, are also encompassed by the invention, as are methods of producing the antibodies by culturing the host cells under conditions permitting production of the antibodies, and recovering the antibodies produced.

In one embodiment, the invention provides an antibody or fragment thereof comprising a HCVR encoded by a nucleic acid sequence selected from the group consisting of SEQ ID NO: 1, 17, 33, 49, 65, 81, 97, 113, 129, 145, 161, 177, 193, 209, 225, 241, 257, 273, 289, and 307, or a substantially identical sequence having at least 90%, at least 95%, at least 98%, or at least 99% homology thereof.

The present invention also provides an antibody or fragment thereof comprising a LCVR encoded by a nucleic acid sequence selected from the group consisting of SEQ ID NO: 9, 25, 41, 57, 73, 89, 105, 121, 137, 153, 169, 185, 201, 217, 233, 249, 265, 281, 297, and 315, or a substantially identical sequence having at least 90%, at least 95%, at least 98%, or at least 99% homology thereof.

The present invention also provides an antibody or antigen-binding fragment of an antibody comprising a HCDR3 domain encoded by a nucleotide sequence selected from the group consisting of SEQ ID NO: 7, 23, 39, 55, 71, 87, 103, 119, 135, 151, 167, 183, 199, 215, 231, 247, 263, 279, 295, and 313, or a substantially identical sequence having at least 90%, at least 95%, at least 98%, or at least 99% homology thereof; and a LCDR3 domain encoded by a nucleotide sequence selected from the group consisting of SEQ ID NO: 15, 31, 47, 63, 79, 95, 111, 127, 143, 159, 175, 191, 207, 223, 239, 255, 271, 287, 303, and 321, or a substantially identical sequence having at least 90%, at least 95%, at least 98%, or at least 99% homology thereof.

The present invention also provides an antibody or fragment thereof which further comprises a HCDR1 domain encoded by a nucleotide sequence selected from the group consisting of SEQ ID NO: 3, 19, 35, 51, 67, 83, 99, 115, 131, 147, 163, 179, 195, 211, 227, 243, 259, 275, 291, and 309, or a substantially identical sequence having at least 90%, at least 95%, at least 98%, or at least 99% homology thereof; a HCDR2 domain encoded by a nucleotide sequence selected from the group consisting of SEQ ID NO: 5, 21, 37, 53, 69, 85, 101, 117, 133, 149, 165, 181, 197, 213, 229, 245, 261, 277, 293, and 311, or a substantially identical sequence having at least 90%, at least 95%, at least 98%, or at least 99% homology thereof; a LCDR1 domain encoded by a nucleotide sequence selected from the group consisting of SEQ ID NO: 11, 27, 43, 59, 75, 91, 107, 123, 139, 155, 171, 187, 203, 219, 235, 251, 267, 283, 299, and 317, or a substantially identical sequence having at least 90%, at least 95%, at least 98%, or at least 99% homology thereof; and a LCDR2 domain encoded by a nucleotide sequence selected from the group consisting of SEQ ID NO: 13, 29, 45, 61, 77, 93, 109, 125, 141, 157, 173, 189, 205, 221, 237, 253, 269, 285, 301, and 319, or a substantially identical sequence having at least 90%, at least 95%, at least 98%, or at least 99% homology thereof.

According to certain embodiments, the antibody or fragment thereof comprises the heavy and light chain CDR sequences encoded by the nucleic acid sequences of SEQ ID NOs: 1 and 9 (e.g. H1M9559N), 17 and 25 (e.g. H1M9566N), 33 and 41 (e.g. H1M9568N), 49 and 57 (e.g. H4H9629P), 65 and 73 (e.g. H4H9633P), 81 and 89 (e.g. H4H9640P), 97 and 105 (e.g. H4H9659P), 113 and 121 (e.g. H4H9660P), 129 and 137 (e.g. H4H9662P), 145 and 153 (e.g. H4H9663P), 161 and 169 (e.g. H4H9664P), 177 and 185 (e.g. H4H9665P), 193 and 201 (e.g. H4H9666P), 209 and 217 (e.g. H4H9667P), 225 and 233 (e.g. H4H9670P), 241 and 249 (e.g. H4H9671P), 257 and 265 (e.g. H4H9672P), 273 and 281 (e.g. H4H9675P), 289 and 297 (e.g. H4H9676P), or 307 and 315 (H1M9565N).

The present invention includes anti-IL-33 antibodies having a modified glycosylation pattern. In some applications, modification to remove undesirable glycosylation sites may be useful, or an antibody lacking a fucose moiety present on the oligosaccharide chain, for example, to increase antibody dependent cellular cytotoxicity (ADCC) function (see Shield et al. (2002) JBC 277:26733). In other applications, modification of galactosylation can be made in order to modify complement dependent cytotoxicity (CDC).

In another aspect, the invention provides a pharmaceutical composition comprising a recombinant human antibody or fragment thereof, which specifically binds IL-33 and a pharmaceutically acceptable carrier. In a related aspect, the invention features a composition which is a combination of an anti-IL-33 antibody and a second therapeutic agent. In one embodiment, the second therapeutic agent is any agent that is advantageously combined with an anti-IL-33 antibody. Exemplary agents that may be advantageously combined with an anti-IL-33 antibody include, without limitation, other agents that inhibit IL-33 activity (including other antibodies or antigen-binding fragments thereof, peptide inhibitors, small molecule antagonists, etc.) and/or agents, which do not directly bind IL-33 but nonetheless interfere with, block or attenuate IL-33-mediated signaling. In one embodiment the second therapeutic agent may be selected from the group consisting of a non-steroidal anti-inflammatory (NSAID), a corticosteroid, a bronchial dilator, an antihistamine, epinephrine, a decongestant, a thymic stromal lymphopoietin (TSLP) antagonist, an IL-13 antagonist, an IL-4 antagonist, an IL-5 antagonist, an IL-6 antagonist, an IL-25 antagonist, an IL-17 antagonist, and another IL-33 antagonist or a different antibody to IL-33. In certain embodiments, the cytokine antagonist may be a small molecule inhibitor (synthetic or naturally derived), or a protein (e.g. an antibody) that interacts with either the cytokine itself, or to a receptor for the cytokine, or to a complex comprising both the cytokine and its receptor(s) (e.g. an antibody to IL-4 or IL-6, or an antibody to the receptor for IL-4 or IL-6). Additional combination therapies and co-formulations involving the anti-IL-33 antibodies of the present invention are disclosed elsewhere herein.

In yet another aspect, the invention provides therapeutic methods for inhibiting IL-33 activity using an anti-IL-33 antibody or antigen-binding portion of an antibody of the invention, wherein the therapeutic methods comprise administering a therapeutically effective amount of a pharmaceutical composition comprising an antibody or antigen-binding fragment of an antibody of the invention. The disorder treated is any disease or condition which is improved, ameliorated, inhibited or prevented by removal, inhibition or reduction of IL-33 activity or signaling. The anti-IL-33 antibodies or antibody fragments of the invention may function to block the interaction between IL-33 and an IL-33 binding partner (e.g., an IL-33 receptor component), or otherwise inhibit the signaling activity of IL-33.

In one embodiment, the invention provides a method for treating an inflammatory disease or disorder, or at least one symptom associated with the inflammatory disease or disorder, the method comprising administering an antibody that binds specifically to IL-33, or an antigen-binding fragment thereof, or a pharmaceutical composition comprising an antibody that binds specifically to IL-33, or an antigen-binding fragment thereof, to a patient in need thereof, wherein the inflammatory disease or disorder is alleviated, or reduced in severity, duration or frequency of occurrence, or at least one symptom associated with the inflammatory disease or disorder is alleviated, or reduced in severity, duration, or frequency of occurrence.

In one embodiment, the inflammatory disease or condition is selected from the group consisting of asthma, atopic dermatitis, chronic obstructive pulmonary disease (COPD), inflammatory bowel disease, multiple sclerosis, arthritis, allergic rhinitis, eosinophilic esophagitis and psoriasis.

In one embodiment, the invention provides a method for treating a patient who demonstrates a sensitivity to an allergen, the method comprising administering an effective amount of an antibody or antigen binding fragment thereof that binds specifically to IL-33, or a pharmaceutical composition comprising an antibody that binds specifically to IL-33, or an antigen-binding fragment thereof, to a patient in need thereof, wherein the patient demonstrates a reduced sensitivity to, or a diminished allergic reaction against the allergen, or does not experience any sensitivity or allergic reaction to, or anaphylactic response to the allergen following administration of the antibody or a composition comprising the antibody.

In one embodiment, the invention provides for administering an effective amount of a second therapeutic agent useful for alleviating the inflammatory disease or disorder, or at least one symptom of the inflammatory disease or disorder, or for diminishing an allergic response to an allergen. As noted above, the second therapeutic agent may be selected from the group consisting of a non-steroidal anti-inflammatory (NSAID), a corticosteroid, a bronchial dilator, an antihistamine, epinephrine, a decongestant, a thymic stromal lymphopoietin (TSLP) antagonist, an IL-13 antagonist, an IL-4 antagonist, an IL-4/IL-13 dual antagonist, an IL-5 antagonist, an IL-6 antagonist, an IL-12/23 antagonist, an IL-22 antagonist, an IL-25 antagonist, an IL-17 antagonist, an IL-31 antagonist, an oral PDE4 inhibitor and another IL-33 antagonist or a different antibody to IL-33.

In a related aspect, the invention provides an anti-IL-33 antibody of the invention, or an antigen-binding fragment thereof, or a pharmaceutical composition comprising the antibody or an-gen-binding fragment thereof for use in treating a disease or disorder related to, or caused by IL-33 activity in a patient. In one embodiment, the disease or disorder related to, or caused by IL-33 activity in a patient is an inflammatory disease or disorder, wherein the inflammatory disease or disorder is selected from the group consisting of asthma, atopic dermatitis, chronic obstructive pulmonary disease (COPD), inflammatory bowel disease, multiple sclerosis, arthritis, allergic rhinitis, eosinophilic esophagitis and psoriasis.

The present invention also includes the use of an anti-IL-33 antibody or antigen binding portion of an antibody of the invention in the manufacture of a medicament for the treatment of a disease or disorder related to or caused by IL-33 activity in a patient. In one embodiment, the disease or disorder related to, or caused by IL-33 activity in a patient is an inflammatory disease or disorder, wherein the inflammatory disease or disorder is selected from the group consisting of asthma, atopic dermatitis, chronic obstructive pulmonary disease (COPD), inflammatory bowel disease, multiple sclerosis, arthritis, allergic rhinitis, eosinophilic esophagitis and psoriasis.

Other embodiments will become apparent from a review of the ensuing detailed description.

BRIEF DESCRIPTION OF THE FIGURES

FIG. 1. Cross Competition between Anti-IL-33 Antibodies for Human IL-33

FIG. 2. Cross Competition between Anti-IL-33 Antibodies for Recombinant Monkey IL-33

DETAILED DESCRIPTION

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice or testing of the present invention, the preferred methods and materials are now described. All patents, applications and non-patent publications mentioned in this specification are incorporated herein by reference in their entireties.

Definitions

The expressions "interleukin-33," "IL-33," and the like, as used herein, refer to a human IL-33 protein as obtained from, for example, R&D Systems, catalogue #3625-IL-010/CF. All references to proteins, polypeptides and protein fragments herein are intended to refer to the human version of the respective protein, polypeptide or protein fragment unless explicitly specified as being from a non-human species (e.g., "mouse IL-33," "monkey IL-33," etc.).

As used herein, "an antibody that binds IL-33" or an "anti-IL-33 antibody" includes antibodies, and antigen-binding fragments thereof, that bind a soluble fragment of an IL-33 protein. Soluble IL-33 molecules include natural IL-33 proteins as well as recombinant IL-33 protein variants such as, e.g., monomeric and dimeric IL-33 constructs.

The term "antibody", as used herein, means any antigen-binding molecule or molecular complex comprising at least one complementarity determining region (CDR) that specifically binds to or interacts with a particular antigen (e.g., IL-33). The term "antibody" includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the invention, the FRs of the anti-IL-33 antibody (or antigen-binding portion thereof) may be identical to the human germline sequences, or may be naturally or artificially modified. An amino acid consensus sequence may be defined based on a side-by-side analysis of two or more CDRs.

The term "antibody", as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H$1; (ii) $V_H$-$C_H$2; (iii) $V_H$-$C_H$3; (iv) $V_H$-$C_H$1-$C_H$2; (v) $V_H$-$C_H$1-$C_H$2-$C_H$3; (vi) $V_H$-$C_H$2-$C_H$3; (vii) $V_H$-$C_L$; (viii) $V_L$-$C_H$1; (ix) $V_L$-$C_H$2; (x) $V_L$-$C_H$3; (xi) $V_L$-$C_H$1-$C_H$2; (xii) $V_L$-$C_H$1-$C_H$2-$C_H$3; (xiii) $V_L$-$C_H$2-$C_H$3; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, including the exemplary bispecific antibody formats disclosed herein, may be adapted for use in the context of an antigen-binding fragment of an antibody of the present invention using routine techniques available in the art.

The antibodies of the present invention may function through complement-dependent cytotoxicity (CDC) or antibody-dependent cell-mediated cytotoxicity (ADCC). "Complement-dependent cytotoxicity" (CDC) refers to lysis of antigen-expressing cells by an antibody of the invention in the presence of complement. "Antibody-dependent cell-mediated cytotoxicity" (ADCC) refers to a cell-mediated reaction in which nonspecific cytotoxic cells that express Fc receptors (FcRs) (e.g., Natural Killer (NK) cells, neutrophils, and macrophages) recognize bound antibody on a target cell and thereby lead to lysis of the target cell. CDC and ADCC can be measured using assays that are well known and available in the art. (See, e.g., U.S. Pat. Nos. 5,500,362 and 5,821,337, and Clynes et al. (1998) Proc. Natl. Acad. Sci. (USA) 95:652-656). The constant region of an antibody is important in the ability of an antibody to fix complement and mediate cell-dependent cytotoxicity. Thus, the isotype of an antibody may be selected on the basis of whether it is desirable for the antibody to mediate cytotoxicity.

In certain embodiments of the invention, the anti-IL-33 antibodies of the invention are human antibodies. The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The antibodies of the invention may, in some embodiments, be recombinant human antibodies. The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

Human antibodies can exist in two forms that are associated with hinge heterogeneity. In one form, an immunoglobulin molecule comprises a stable four chain construct of approximately 150-160 kDa in which the dimers are held together by an interchain heavy chain disulfide bond. In a second form, the dimers are not linked via inter-chain disulfide bonds and a molecule of about 75-80 kDa is formed composed of a covalently coupled light and heavy chain (half-antibody). These forms have been extremely difficult to separate, even after affinity purification.

The frequency of appearance of the second form in various intact IgG isotypes is due to, but not limited to, structural differences associated with the hinge region isotype of the antibody. A single amino acid substitution in the hinge region of the human IgG4 hinge can significantly reduce the appearance of the second form (Angal et al. (1993) Molecular Immunology 30:105) to levels typically observed using a human IgG1 hinge. The instant invention encompasses antibodies having one or more mutations in the hinge, $C_H2$ or $C_H3$ region which may be desirable, for example, in production, to improve the yield of the desired antibody form.

The antibodies of the invention may be isolated antibodies. An "isolated antibody," as used herein, means an antibody that has been identified and separated and/or recovered from at least one component of its natural environment. For example, an antibody that has been separated or removed from at least one component of an organism, or from a tissue or cell in which the antibody naturally exists or is naturally produced, is an "isolated antibody" for purposes of the present invention. An isolated antibody also includes an antibody in situ within a recombinant cell. Isolated antibodies are antibodies that have been subjected to at least one purification or isolation step. According to certain embodiments, an isolated antibody may be substantially free of other cellular material and/or chemicals.

The present invention includes neutralizing and/or blocking anti-IL-33 antibodies. A "neutralizing" or "blocking" antibody, as used herein, is intended to refer to an antibody whose binding to IL-33: (i) interferes with the interaction between IL-33 or an IL-33 fragment and an IL-33 receptor component (e.g., ST2, IL-1RAcP, etc.); and/or (ii) results in inhibition of at least one biological function of IL-33. The inhibition caused by an IL-33 neutralizing or blocking antibody need not be complete so long as it is detectable using an appropriate assay. Exemplary assays for detecting IL-33 inhibition are described in the working Examples herein.

The anti-IL-33 antibodies disclosed herein may comprise one or more amino acid substitutions, insertions and/or deletions in the framework and/or CDR regions of the heavy and light chain variable domains as compared to the corresponding germline sequences from which the antibodies were derived. Such mutations can be readily ascertained by comparing the amino acid sequences disclosed herein to germline sequences available from, for example, public antibody sequence databases. The present invention includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present invention may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present invention.

The present invention also includes anti-IL-33 antibodies comprising variants of any of the HCVR, LCVR, and/or CDR amino acid sequences disclosed herein having one or more conservative substitutions. For example, the present invention includes anti-IL-33 antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences disclosed herein.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 95%, and more preferably at least about 96%, 97%, 98% or 99% of the nucleotide bases, as measured by any well-known algorithm of sequence identity, such as FASTA, BLAST or Gap, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 95% sequence identity, even more preferably at least 98% or 99% sequence identity. Preferably, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24: 307-331, herein incorporated by reference. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443-1445, herein incorporated by reference. A "moderately conservative" replacement is any change having a nonnegative value in the PAM250 log-likelihood matrix.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG software contains programs such as Gap and Bestfit which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol. 215:403-410 and Altschul et al. (1997) Nucleic Acids Res. 25:3389-402, each herein incorporated by reference.

An "inflammatory disease or disorder", as used herein, refers to a disease, disorder or pathological condition where the pathology results, in whole or in part, from, e.g., a change in number, change in rate of migration, or change in activation, of cells of the immune system. Cells of the immune system include, e.g., T cells, B cells, monocytes or macrophages, antigen presenting cells (APCs), dendritic cells, microglia, NK cells, neutrophils, eosinophils, mast cells, or any other cell specifically associated with the immunology, for example, cytokine-producing endothelial or epithelial cells. As used herein, in one embodiment, the "inflammatory disease or disorder" is an immune disorder or condition selected from the group consisting of asthma, (including steroid resistant asthma, steroid sensitive asthma, eosinophilic asthma or non-eosinophilic asthma, allergy, anaphylaxis, multiple sclerosis, inflammatory bowel disorder (e.g. Crohn's disease or ulcerative colitis), chronic obstructive pulmonary disease (COPD, which may or may not be related to, caused in part by, or resulting from, exposure to first or second hand cigarette smoke), lupus, atopic dermatitis, psoriasis, scleroderma and other fibrotic diseases, sjogren's syndrome, vasculitis (behcet's disease, Giant cell arteritis, Henoch-Schonlein purpura and Churg Strauss syndrome) and arthritis. In another embodiment, the arthritis is selected from the group consisting of rheumatoid arthritis, osteoarthritis, and psoriatic arthritis. In another embodiment, the "inflammatory disease or disorder" is an immune disorder or condition comprises a $TH_1$-type response or a $TH_2$-type response.

The phrase "Inhibits or attenuates IL-33-mediated signaling", as used herein, refers to the degree to which IL-33 stimulates signal transduction through ST2 and IL-1RAcP, which is diminished in the presence of an antagonist, such as an IL-33 antibody as described herein, relative to the degree to which IL-33 stimulates signal transduction through ST2 and IL-1RAcP in the absence of the antagonist such as an IL-33 antibody as described herein. To examine the extent of inhibition, a sample is treated with a potential inhibitor/antagonist and is compared to a control sample without the inhibitor/antagonist. Control samples, i.e., not treated with antagonist, are assigned a relative activity value of 100%. Inhibition is achieved when the activity value relative to the control is about 90%, 85%, 80%, 75%, 70%, 65%, 60%, 55%, 50%, 45%, 40%, 35%, 30%, 25%, or 20% or less. An endpoint in inhibition may comprise a predetermined quantity or percentage of, e.g., an indicator of inflammation, or cell degranulation, secretion or activation, such as the release of a cytokine. Inhibition of IL-33 signal transduction through ST2 and IL-1RAcP can be determined by assaying for IL-33 signal transduction in an in vitro assay, such as that described herein in Example 6. In addition, in vivo assays can be used to determine whether a molecule is an antagonist of IL-33. For example, an in vivo assay such as that described in Examples 11 and 12 may be used to assess the effect of an antibody to IL-33 on lung inflammation in allergen-sensitized animals that are homozygous for expression of human IL-33. Following sensitization of the animals with allergen, a subset of the animals is treated with either an anti-IL-33 antibody of the invention or a negative isotype control antibody. Afterwards, the animals are sacrificed and the lungs are harvested for assessment of cellular infiltrates, as well as cytokine measurements (IL-4 and IL-5). An IL-33 antibody that is effective as an antagonist should demonstrate a trend towards reduction in inflammatory cells in the lung, as well as a trend towards reduction in cytokines such as IL-4 and IL-5.

Biological Characteristics of the Antibodies

The present invention includes anti-IL-33 antibodies and antigen-binding fragments thereof that bind human IL-33 and inhibit or attenuate IL-33-mediated signaling. An anti-IL-33 antibody is deemed to "inhibit or attenuate IL-33-mediated signaling" if, e.g., the antibody exhibits one or more properties selected from the group consisting of: (1) inhibition of IL-33-mediated signaling in a cell-based bioassay; (2) inhibition of IL-33-induced degranulation of human basophils; (3) inhibition of IL-33-induced IFNγ production from human PBMCs; (4) reduction in cytokine levels that are elevated in a mammal as a result of exposure to an allergen, e.g. IL-4 or IL-5; and (5) inhibition of lung inflammation resulting from acute or chronic exposure to an allergen (e.g. house dust mites (HDM)).

Inhibition of IL-33-mediated signaling in a cell-based bioassay means that an anti-IL-33 antibody or antigen-binding fragment thereof inhibits or reduces the signal produced in cells that express an IL-33 receptor and a reporter element that produces a detectable signal in response to IL-33 binding, e.g., using the assay format as defined in Example 6 herein, or a substantially similar assay. For example, the present invention includes antibodies and antigen-binding fragments thereof that block IL-33-mediated signaling in cells expressing human ST2, with an $IC_{50}$ of less than about 2 nM, less than about 1 nM, less than about 900 pM, less than about 800 pM, less than about 700 pM, less than about 600 pM, less than about 500 pM, less than about 400 pM, less than about 350 pM, less than about 300 pM, less than about 250 pM, less than about 200 pM, less than about 150 pM, less than about 100 pM, less than about 90 pM, less than about 80 pM, less than about 70 pM, less than about 60 pM, less than about 50 pM, less than about 40 pM, less than about 30 pM, less than about 20 pM, or less than about 10 pM, as measured in a cell-based blocking bioassay, e.g., using the assay format as defined in Example 5 herein, or a substantially similar assay.

Inhibition of IL-33-induced degranulation of human basophils means that an anti-IL-33 antibody or antigen-binding fragment thereof inhibits or reduces the extent of IL-33-induced basophil degranulation in vitro, e.g., as measured using the assay system of Example 7 or a substantially similar assay. For example, the present invention includes antibodies and antigen-binding fragments thereof that inhibit degranulation of human basophils in the presence of human IL-33 (e.g., about 100 pM final concentration), with an $IC_{50}$ of less than about 500 pM, less than about 400 pM, less than about 350 pM, less than about 300 pM, less than about 250 pM, less than about 200 pM, less than about 150 pM, less than about 100 pM, less than about 90 pM, less than about 80 pM, less than about 70 pM, less than about 60 pM, less than about 50 pM, less than about 40 pM, less than about 30 pM, less than about 20 pM, or less than about 10 pM, as measured in an in vitro human basophil degranulation assay, e.g., using the assay format as defined in Example 7 herein, or a substantially similar assay.

Inhibition of IL-33-induced IFNγ production from human PBMCs means that an anti-IL-33 antibody or antigen-binding fragment thereof inhibits or reduces the amount of IFNγ released from PBMCs treated with human IL-33 in the presence of human IL-12, e.g., as measured using the assay system of Example 8 or a substantially similar assay. For example, the present invention includes antibodies and antigen-binding fragments thereof that inhibit IL-33-induced release of IFNy, in the presence of human IL-12, with an $IC_{50}$ of less than about 50 nM, less than about 25 nM, less than about 20 nM, less than about 15 nM, less than about 10 nM, less than about 5 nM, less than about 1 nM, less than about 900 pM, less than about 800 pM, less than about 700 pM, less than about 600 pM, less than about 500 pM, less than about 400 pM or less than about 300 pM, as measured in an IL-33-induced IFNγ release assay, e.g., using the assay format as defined in Example 8 herein, or a substantially similar assay.

In certain embodiments, the anti-IL-33 antibodies and antigen-binding fragments of the present invention block the binding of IL-33 to an IL-33 receptor (e.g., ST2). For example, the present invention includes anti-IL-33 antibodies that block the binding of IL-33 to ST2 in vitro, with an $IC_{50}$ value of less than about 15 nM, as measured by an ELISA-based immunoassay, e.g., using the assay format as defined in Example 4 herein, or a substantially similar assay. In certain embodiments, the antibodies or antigen-binding fragments of the present invention block the binding of IL-33 to ST2 in vitro with an $IC_{50}$ value of less than about 10 nM, less than about 5 nM, less than about 900 pM, less than about 800 pM, less than about 700 pM, less than about 600 pM, less than about 500 pM, less than about 400 pM, less than about 300 pM, less than about 280 pM, less than about 260 pM, less than about 250 pM, less than about 240 pM, less than about 230 pM, less than about 220 pM, less than about 200 pM, less than about 180 pM, less than about 160 pM, or less than about 150 pM, as measured by an ELISA-based immunoassay, e.g., using the assay format as defined in Example 4 herein, or a substantially similar assay.

In other embodiments, however, certain anti-IL-33 antibodies and antigen-binding fragments of the present invention, despite having the ability to inhibit or attenuate IL-33-mediated signaling, do not block or only partially block the interaction of IL-33 and ST2. Such antibodies and antigen-binding fragments thereof, may be referred to herein as "indirect blockers." Without being bound by theory, it is believed that the indirect blockers of the invention function by binding to IL-33 at an epitope that does overlap, or overlaps only partially, with the ST2-binding domain of IL-33, but nonetheless interfere with IL-33-mediated signaling without blocking the IL-33/ST2 interaction directly.

The present invention includes anti-IL-33 antibodies and antigen-binding fragments thereof that bind soluble IL-33 molecules with high affinity. For example, the present invention includes antibodies and antigen-binding fragments of antibodies that bind IL-33 (e.g., at 25° C. or 37° C.) with a $K_D$ of less than about 10 nM as measured by surface plasmon resonance, e.g., using the assay format as defined in Example 3 herein. In certain embodiments, the antibodies or antigen-binding fragments of the present invention bind IL-33 with a $K_D$ of less than about 5 nM, less than about 2 nM, less than about 1 nM, less than about 800 pM, less than about 600 pM, less than about 500 pM, less than about 400 pM, less than about 300 pM, less than about 200 pM, less than about 180 pM, or less than about 160 pM, as measured by surface plasmon resonance, e.g., using the assay format as defined in Example 3 herein, or a substantially similar assay.

The present invention also includes anti-IL-33 antibodies and antigen-binding fragments thereof that specifically bind to IL-33 with a dissociative half-life (t½) of greater than about 10 minutes as measured by surface plasmon resonance at 25° C. or 37° C., e.g., using the assay format as defined in Example 3 herein, or a substantially similar assay. In certain embodiments, the antibodies or antigen-binding fragments of the present invention bind IL-33 with a t½ of greater than about 20 minutes, greater than about 30 minutes, greater than about 40 minutes, greater than about 50 minutes, greater than about 60 minutes, greater than about 70 minutes, greater than about 80 minutes, greater than about 90 minutes, greater than about 100 minutes, as measured by surface plasmon resonance at 25° C. or 37° C., e.g., using the assay format as defined in Example 3 herein, or a substantially similar assay.

The antibodies of the present invention may possess one or more of the aforementioned biological characteristics, or any combinations thereof. Other biological characteristics of the antibodies of the present invention will be evident to a person of ordinary skill in the art from a review of the present disclosure including the working Examples herein.

Anti-IL-33 Antibodies Comprising Fc Variants

According to certain embodiments of the present invention, anti-IL-33 antibodies are provided comprising an Fc domain comprising one or more mutations which enhance or diminish antibody binding to the FcRn receptor, e.g., at acidic pH as compared to neutral pH. For example, the present invention includes anti-IL-33 antibodies comprising a mutation in the $C_H2$ or a $C_H3$ region of the Fc domain, wherein the mutation(s) increases the affinity of the Fc domain to FcRn in an acidic environment (e.g., in an endosome where pH ranges from about 5.5 to about 6.0). Such mutations may result in an increase in serum half-life of the antibody when administered to an animal. Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., H/L/R/S/P/Q or K) and/or 434 (e.g., H/F or Y); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P). In yet another embodiment, the modification comprises a 265A (e.g., D265A) and/or a 297A (e.g., D297A) modification.

For example, the present invention includes anti-IL-33 antibodies comprising an Fc domain comprising one or more pairs or groups of mutations selected from the group consisting of: 250Q and 248L (e.g., T250Q and M248L); 252Y, 254T and 256E (e.g., M252Y, S254T and T256E); 428L and 434S (e.g., M428L and N434S); and 433K and 434F (e.g., H433K and N434F). All possible combinations of the foregoing Fc domain mutations, and other mutations within the antibody variable domains disclosed herein, are contemplated within the scope of the present invention.

The present invention also includes anti-IL-33 antibodies comprising a chimeric heavy chain constant ($C_H$) region, wherein the chimeric $C_H$ region comprises segments derived from the $C_H$ regions of more than one immunoglobulin isotype. For example, the antibodies of the invention may comprise a chimeric $C_H$ region comprising part or all of a $C_H2$ domain derived from a human IgG1, human IgG2 or human IgG4 molecule, combined with part or all of a $C_H3$ domain derived from a human IgG1, human IgG2 or human IgG4 molecule. According to certain embodiments, the antibodies of the invention comprise a chimeric $C_H$ region having a chimeric hinge region. For example, a chimeric hinge may comprise an "upper hinge" amino acid sequence (amino acid residues from positions 216 to 227 according to EU numbering) derived from a human IgG1, a human IgG2 or a human IgG4 hinge region, combined with a "lower hinge" sequence (amino acid residues from positions 228 to 236 according to EU numbering) derived from a human IgG1, a human IgG2 ora human IgG4 hinge region. According to certain embodiments, the chimeric hinge region comprises amino acid residues derived from a human IgG1 or a human IgG4 upper hinge and amino acid residues derived from a human IgG2 lower hinge. An antibody comprising a chimeric $C_H$ region as described herein may, in certain embodiments, exhibit modified Fc effector functions without adversely affecting the therapeutic or pharmacokinetic properties of the antibody. (See, e.g., U.S. Provisional Appl. No. 61/759,578, filed Feb. 1, 2013, the disclosure of which is hereby incorporated by reference in its entirety).

Epitope Mapping and Related Technologies

The present invention includes anti-IL-33 antibodies which interact with one or more amino acids of IL-33. For example, the present invention includes anti-IL-33 antibodies that interact with one or more amino acids located within the ST2-interacting domain of IL-33. The epitope to which the antibodies bind may consist of a single contiguous sequence of 3 or more (e.g., 3, 4, 5, 6, 7, 8, 9, 10, 11, 12, 13, 14, 15, 16, 17, 18, 19, 20 or more) amino acids of IL-33. Alternatively, the epitope may consist of a plurality of non-contiguous amino acids (or amino acid sequences) of IL-33.

Various techniques known to persons of ordinary skill in the art can be used to determine whether an antibody "interacts with one or more amino acids" within a polypeptide or protein. Exemplary techniques include, e.g., routine cross-blocking assay such as that described *Antibodies*, Harlow and Lane (Cold Spring Harbor Press, Cold Spring Harb., N.Y,.), alanine scanning mutational analysis, peptide blots analysis (Reineke, 2004, Methods Mol Biol 248:443-463), and peptide cleavage analysis. In addition, methods such as epitope excision, epitope extraction and chemical modification of antigens can be employed (Tomer, 2000, Protein Science 9:487-496). Another method that can be used to identify the amino acids within a polypeptide with which an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water to allow hydrogen-deuterium exchange to occur at all residues except for the residues protected by the antibody (which remain deuterium-labeled). After dissociation of the antibody, the target protein is subjected to protease cleavage and mass spectrometry analysis, thereby revealing the deuterium-labeled residues which correspond to the specific amino acids with which the antibody interacts. See, e.g., Ehring (1999) *Analytical Biochemistry* 267(2):252-259; Engen and Smith (2001) *Anal. Chem.* 73:256A-265A.

The present invention further includes anti-IL-33 antibodies that bind to the same epitope as any of the specific exemplary antibodies described herein (e.g. H1M9559N, H1M9566N, H1M9568N, H4H9629P, H4H9633P, H4H9640P, H4H9659P, H4H9660P, H4H9662P, H4H9663P, H4H9664P, H4H9665P, H4H9666P, H4H9667P, H4H9670P, H4H9671P, H4H9672P, H4H9675P, H4H9676P, H1M9565N, etc.). Likewise, the present invention also includes anti-IL-33 antibodies that compete for binding to IL-33 with any of the specific exemplary antibodies described herein (e.g. H1M9559N, H1M9566N, H1M9568N, H4H9629P, H4H9633P, H4H9640P, H4H9659P, H4H9660P, H4H9662P, H4H9663P, H4H9664P, H4H9665P, H4H9666P, H4H9667P, H4H9670P, H4H9671P, H4H9672P, H4H9675P, H4H9676P, H1M9565N, etc.).

One can easily determine whether an antibody binds to the same epitope as, or competes for binding with, a reference anti-IL-33 antibody by using routine methods known in the art and exemplified herein. For example, to determine if a test antibody binds to the same epitope as a reference anti-IL-33 antibody of the invention, the reference antibody is allowed to bind to an IL-33 protein. Next, the ability of a test antibody to bind to the IL-33 molecule is assessed. If the test antibody is able to bind to IL-33 following saturation binding with the reference anti-IL-33 antibody, it can be concluded that the test antibody binds to a different epitope than the reference anti-IL-33 antibody. On the other hand, if the test antibody is not able to bind to the IL-33 molecule following saturation binding with the reference anti-IL-33 antibody, then the test antibody may bind to the same epitope as the epitope bound by the reference anti-IL-33 antibody of the invention. Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, Biacore, flow cytometry or any other quantitative or qualitative antibody-binding assay available in the art. In accordance with certain embodiments of the present invention, two antibodies bind to the same (or overlapping) epitope if, e.g., a 1-, 5-, 10-, 20- or 100-fold excess of one antibody inhibits binding of the other by at least 50% but preferably 75%, 90% or even 99% as measured in a competitive binding assay (see, e.g., Junghans et al., Cancer Res. 1990:50:1495-1502). Alternatively, two antibodies are deemed to bind to the same epitope if essentially all amino acid mutations in the antigen that reduce or eliminate binding of one antibody reduce or eliminate binding of the other. Two antibodies are deemed to have "overlapping epitopes" if only a subset of the amino acid mutations that reduce or eliminate binding of one antibody reduce or eliminate binding of the other.

To determine if an antibody competes for binding (or cross-competes for binding) with a reference anti-IL-33 antibody, the above-described binding methodology is performed in two orientations: In a first orientation, the reference antibody is allowed to bind to an IL-33 protein under saturating conditions followed by assessment of binding of the test antibody to the IL-33 molecule. In a second orientation, the test antibody is allowed to bind to an IL-33 molecule under saturating conditions followed by assessment of binding of the reference antibody to the IL-33 molecule. If, in both orientations, only the first (saturating) antibody is capable of binding to the IL-33 molecule, then it is concluded that the test antibody and the reference antibody compete for binding to IL-33. As will be appreciated by a person of ordinary skill in the art, an antibody that competes for binding with a reference antibody may not necessarily bind to the same epitope as the reference antibody, but may sterically block binding of the reference antibody by binding an overlapping or adjacent epitope.

Preparation of Human Antibodies

Methods for generating monoclonal antibodies, including fully human monoclonal antibodies are known in the art. Any such known methods can be used in the context of the present invention to make human antibodies that specifically bind to human IL-33.

Using VELOCIMMUNE™ technology, for example, or any other known method for generating fully human monoclonal antibodies, high affinity chimeric antibodies to IL-33 are initially isolated having a human variable region and a mouse constant region. As in the experimental section below, the antibodies are characterized and selected for desirable characteristics, including affinity, selectivity, epitope, etc. If necessary, mouse constant regions are replaced with a desired human constant region, for example wild-type or modified IgG1 or IgG4, to generate a fully human anti-IL-33 antibody. While the constant region selected may vary according to specific use, high affinity antigen-binding and target specificity characteristics reside in the variable region. In certain instances, fully human anti-IL-33 antibodies are isolated directly from antigen-positive B cells.

Bioequivalents

The anti-IL-33 antibodies and antibody fragments of the present invention encompass proteins having amino acid sequences that vary from those of the described antibodies but that retain the ability to bind human IL-33. Such variant antibodies and antibody fragments comprise one or more additions, deletions, or substitutions of amino acids when compared to parent sequence, but exhibit biological activity that is essentially equivalent to that of the described antibodies. Likewise, the anti-IL-33 antibody-encoding DNA sequences of the present invention encompass sequences that comprise one or more additions, deletions, or substitutions of nucleotides when compared to the disclosed sequence, but that encode an anti-IL-33 antibody or antibody fragment that is essentially bioequivalent to an anti-IL-33 antibody or antibody fragment of the invention. Examples of such variant amino acid and DNA sequences are discussed above.

Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single does or multiple dose. Some antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins are bioequivalent if there are no clinically meaningful differences in their safety, purity, and potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antibody.

Bioequivalent variants of anti-IL-33 antibodies of the invention may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antibodies may include anti-IL-33 antibody variants comprising amino acid changes which modify the glycosylation characteristics of the antibodies, e.g., mutations which eliminate or remove glycosylation.

Species Selectivity and Species Cross-Reactivity

The present invention, according to certain embodiments, provides anti-IL-33 antibodies that bind to human IL-33 but not to IL-33 from other species. The present invention also includes anti-IL-33 antibodies that bind to human IL-33 and to IL-33 from one or more non-human species. For example, the anti-IL-33 antibodies of the invention may bind to human IL-33 and may bind or not bind, as the case may be, to one or more of mouse, rat, guinea pig, hamster, gerbil, pig, cat, dog, rabbit, goat, sheep, cow, horse, camel, cynomolgous, marmoset, rhesus or chimpanzee IL-33. According to certain exemplary embodiments of the present invention, anti-IL-33 antibodies are provided which specifically bind human IL-33 and cynomolgus monkey (e.g., Macaca fascicularis) IL-33.

Immunoconjugates

The invention encompasses anti-IL-33 monoclonal antibodies conjugated to a therapeutic moiety ("immunoconjugate"), such as a cytotoxin, a chemotherapeutic drug, an immunosuppressant or a radioisotope. Cytotoxic agents include any agent that is detrimental to cells. Examples of suitable cytotoxic agents and chemotherapeutic agents for forming immunoconjugates are known in the art, (see for example, WO 05/103081).

Multispecific Antibodies

The antibodies of the present invention may be monospecific, bi-specific, or multispecific. Multispecific antibodies may be specific for different epitopes of one target polypeptide or may contain antigen-binding domains specific for more than one target polypeptide. See, e.g., Tutt et al., 1991, J. Immunol. 147:60-69; Kufer et al., 2004, Trends Biotechnol. 22:238-244. The anti-IL-33 antibodies of the present invention can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment to produce a bi-specific or a multispecific antibody with a second binding specificity. For example, the present invention includes bi-specific antibodies wherein one arm of an immunoglobulin is specific for human IL-33 or a fragment thereof, and the other arm of the immunoglobulin is specific for a second therapeutic target or is conjugated to a therapeutic moiety.

An exemplary bi-specific antibody format that can be used in the context of the present invention involves the use of a first immunoglobulin (Ig) $C_H3$ domain and a second Ig $C_H3$ domain, wherein the first and second Ig $C_H3$ domains differ from one another by at least one amino acid, and wherein at least one amino acid difference reduces binding of the bispecific antibody to Protein A as compared to a bi-specific antibody lacking the amino acid difference. In one embodiment, the first Ig $C_H3$ domain binds Protein A and the second Ig $C_H3$ domain contains a mutation that reduces or abolishes Protein A binding such as an H95R modification (by IMGT exon numbering; H435R by EU numbering). The second $C_H3$ may further comprise a Y96F modification (by IMGT; Y436F by EU). Further modifications that may be found within the second $C_H3$ include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419Q, and V422I by EU) in the case of IgG4 antibodies. Variations on the bi-specific antibody format described above are contemplated within the scope of the present invention.

Other exemplary bispecific formats that can be used in the context of the present invention include, without limitation, e.g., scFv-based or diabody bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED) body, leucine zipper, Duobody, IgG1/IgG2, dual acting Fab (DAF)-IgG, and Mabe bispecific formats (see, e.g., Klein et al. 2012, mAbs 4:6, 1-11, and references cited therein, for a review of the foregoing formats). Bispecific antibodies can also be constructed using peptide/nucleic acid conjugation, e.g., wherein unnatural amino acids with orthogonal chemical reactivity are used to generate site-specific antibody-oligonucleotide conjugates which then self-assemble into multimeric complexes with defined composition, valency and geometry. (See, e.g., Kazane et al., *J. Am. Chem. Soc.* [Epub: Dec. 4, 2012]).

pH-Dependent Binding

The present invention provides antibodies and antigen-binding fragments thereof that bind IL-33 in a pH-dependent manner. For example, an anti-IL-33 antibody of the invention may exhibit reduced binding to IL-33 at acidic pH as compared to neutral pH. Alternatively, an anti-IL-33 antibody of the invention may exhibit enhanced binding to its antigen at acidic pH as compared to neutral pH.

In certain instances, "reduced binding to IL-33 at acidic pH as compared to neutral pH" is expressed in terms of a ratio of the $K_D$ value of the antibody binding to IL-33 at acidic pH to the $K_D$ value of the antibody binding to IL-33 at neutral pH (or vice versa). For example, an antibody or antigen-binding fragment thereof may be regarded as exhibiting "reduced binding to IL-33 at acidic pH as compared to neutral pH" for purposes of the present invention if the antibody or antigen-binding fragment thereof exhibits an acidic/neutral $K_D$ ratio of about 3.0 or greater. In certain exemplary embodiments, the acidic/neutral $K_D$ ratio for an antibody or antigen-binding fragment of the present invention can be about 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 20.0. 25.0, 30.0, 40.0, 50.0, 60.0, 70.0, 100.0 or greater Antibodies with pH-dependent binding characteristics may be obtained, e.g., by screening a population of antibodies for reduced (or enhanced) binding to a particular antigen at acidic pH as compared to neutral pH. Additionally, modifications of the antigen-binding domain at the amino acid level may yield antibodies with pH-dependent characteristics. For example, by substituting one or more amino acids of an antigen-binding domain (e.g., within a CDR) with a histidine residue, an antibody with reduced antigen-binding at acidic pH relative to neutral pH may be obtained. As used herein, the expression "acidic pH" means a pH of about 6.0 or less, about 5.5 or less, or about 5.0 or less. The expression "acidic pH" includes pH values of about 6.0, 5.95, 5.9, 5.85, 5.8, 5.75, 5.7, 5.65, 5.6, 5.55, 5.5, 5.45, 5.4, 5.35, 5.3, 5.25, 5.2, 5.15, 5.1, 5.05, 5.0, or less. As used herein, the expression "neutral pH" means a pH of about 7.0 to about 7.4. The expression "neutral pH" includes pH values of about 7.0, 7.05, 7.1, 7.15, 7.2, 7.25, 7.3, 7.35, and 7.4.

Therapeutic Formulation and Administration

The invention provides pharmaceutical compositions comprising the anti-IL-33 antibodies or antigen-binding fragments thereof of the present invention. The pharmaceutical compositions of the invention are formulated with suitable carriers, excipients, and other agents that provide improved transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™, Life Technologies, Carlsbad, Calif.), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of antibody administered to a patient may vary depending upon the age and the size of the patient, target disease, conditions, route of administration, and the like. The preferred dose is typically calculated according to body weight or body surface area. When an antibody of the present invention is used for treating a condition or disease associated with IL-33 activity in an adult patient, it may be advantageous to intravenously administer the antibody of the present invention normally at a single dose of about 0.01 to about 20 mg/kg body weight, more preferably about 0.02 to about 7, about 0.03 to about 5, or about 0.05 to about 3 mg/kg body weight. Depending on the severity of the condition, the frequency and the duration of the treatment can be adjusted. Effective dosages and schedules for administering anti-IL-33 antibodies may be determined empirically; for example, patient progress can be monitored by periodic assessment, and the dose adjusted accordingly. Moreover, interspecies scaling of dosages can be performed using well-known methods in the art (e.g., Mordenti et al., 1991, *Pharmaceut. Res.* 8:1351).

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al., 1987, J. Biol. Chem. 262:4429-4432). Methods of introduction include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but are not limited to AUTOPEN™ (Owen Mumford, Inc., Woodstock, UK), DISETRONIC™ pen (Disetronic Medical Systems, Bergdorf, Switzerland), HUMALOG MIX 75/25™ pen, HUMALOG™ pen, HUMALIN 70/30™ pen (Eli Lilly and Co., Indianapolis, Ind.), NOVOPENTM I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (sanofi-aventis, Frankfurt, Germany), to name only a few. Examples of disposable pen delivery devices having applications in subcutaneous delivery of a pharmaceutical composition of the present invention include, but are not limited to, the SOLOSTAR™ pen (sanofi-aventis), the FLEXPEN™ (Novo Nordisk), and the KWIKPEN™ (Eli Lilly), the SURECLICK™ Autoinjector (Amgen, Thousand Oaks, Calif.), the PENLET™ (Haselmeier, Stuttgart, Germany), the EPIPEN (Dey, L.P.), and the HUMIRA™ Pen (Abbott Labs, Abbott Park Ill.), to name only a few.

In certain situations, the pharmaceutical composition can be delivered in a controlled release system. In one embodiment, a pump may be used (see Langer, supra; Sefton, 1987, CRC Crit. Ref. Biomed. Eng. 14:201). In another embodiment, polymeric materials can be used; see, Medical Applications of Controlled Release, Langer and Wise (eds.), 1974, CRC Pres., Boca Raton, Fla. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, 1990, Science 249:1527-1533.

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid antibody contained is generally about 5 to about 500 mg per dosage form in a unit dose; especially in the form of injection, it is preferred that the aforesaid antibody is contained in about 5 to about 100 mg and in about 10 to about 250 mg for the other dosage forms.

Therapeutic Uses of the Antibodies

Experiments using mouse model systems, conducted by the present inventors, have contributed to the identification of various diseases and conditions that can be treated, prevented and/or ameliorated by IL-33 antagonism. For example, hydrodynamic delivery of mouse IL-33 DNA resulted in the induction of lung mucus accumulation and increases in total serum IgE in mice. In addition, mIL-33 DNA delivery resulted in up-regulation of ST2 and various downstream cytokines as measured by microarray analysis. Experiments conducted by the present inventors using IL-33 knock-out mice also revealed various potential therapeutic benefits of IL-33 antagonism. For example, macroscopic scoring and skin infiltrates were found to be comparable between wild-type mice and IL-33$^{-/-}$ mice in a model of IMQ-induced psoriasis. Moreover, IL-33$^{-/-}$ mice showed reduced eosinophilia and residual mucus accumulation in an allergen-induced lung inflammation model.

The antibodies of the invention are useful, inter alia, for the treatment, prevention and/or amelioration of any disease or disorder associated with or mediated by IL-33 expression, signaling, or activity, or treatable by blocking the interaction between IL-33 and a IL-33 ligand (e.g., ST2) or otherwise inhibiting IL-33 activity and/or signaling. For example, the present invention provides methods for treating, asthma (e.g., allergic asthma, non-allergic asthma, severe refractory asthma, asthma exacerbations, steroid resistant asthma, steroid sensitive asthma, eosinophilic asthma or non-eosinophilic asthma, etc.), atopic dermatitis, psoriasis, other inflammatory disorders, allergy, anaphylaxis, cardiovascular disease, central nervous system disease, pain, arthritis (e.g., rheumatoid arthritis, osteoarthritis, psoriatic arthritis, etc.), giant cell arteritis, vasculitis (behcet's disease and Churg Strauss syndrome), Henoch-Schonlein purpura., multiple sclerosis, inflammatory bowel disorder (e.g. Crohn's disease or ulcerative colitis), lupus, and sjogren's syndrome.

The antibodies of the present invention are also useful for the treatment, prevention and/or amelioration of one or more fibrotic diseases. Exemplary fibrotic diseases that are treatable by administering the anti-IL-33 antibodies of the invention include pulmonary fibrosis (e.g., idiopathic pulmonary fibrosis, bleomycin-induced pulmonary fibrosis, asbestos-induced pulmonary fibrosis, and bronchiolitis obliterans syndrome), chronic asthma, fibrosis associated with acute lung injury and acute respiratory distress (e.g., bacterial pneumonia induced fibrosis, trauma induced fibrosis, viral pneumonia induced fibrosis, ventilator induced fibrosis, non-pulmonary sepsis induced fibrosis and aspiration induced fibrosis), silicosis, radiation-induced fibrosis, chronic obstructive pulmonary disease (COPD, which may or may not be related to, caused in part by, or resulting from, exposure to first or second hand cigarette smoke), scleroderma, ocular fibrosis, skin fibrosis (e.g., scleroderma), hepatic fibrosis (e.g., cirrhosis, alcohol-induced liver fibrosis, non-alcoholic steatohepatitis (NASH), bilary duct injury, primary bilary cirrhosis, infection- or viral-induced liver fibrosis, autoimmune hepatitis, kidney (renal) fibrosis, cardiac fibrosis, atherosclerosis, stent restenosis, and myelofibrosis.

In the context of the methods of treatment described herein, the anti-IL-33 antibody may be administered as a monotherapy (i.e., as the only therapeutic agent) or in combination with one or more additional therapeutic agents (examples of which are described elsewhere herein).

Combination Therapies and Formulations

The present invention includes compositions and therapeutic formulations comprising any of the anti-IL-33 antibodies described herein in combination with one or more additional therapeutically active components, and methods of treatment comprising administering such combinations to subjects in need thereof.

The anti-IL-33 antibodies of the present invention may be co-formulated with and/or administered in combination with, e.g., cytokine inhibitors, including small-molecule cytokine inhibitors and antibodies that bind to cytokines such as IL-1, IL-2, IL-3, IL-4, IL-5, IL-6, IL-8, IL-9, IL-11, IL-12, IL-13, IL-17, IL-18, IL-21, IL-23, IL-25, IL-26, or antagonists of their respective receptors.

The anti-IL-33 antibodies of the invention may also be administered and/or co-formulated in combination with antivirals, antibiotics, analgesics, corticosteroids, steroids, oxygen, antioxidants, metal chelators, IFN-gamma, and/or NSAIDs.

The additional therapeutically active component(s) may be administered just prior to, concurrent with, or shortly after the administration of an anti-IL-33 antibody of the present invention; (for purposes of the present disclosure, such administration regimens are considered the administration of an anti-IL-33 antibody "in combination with" an additional therapeutically active component). The present invention includes pharmaceutical compositions in which an anti-IL-33 antibody of the present invention is co-formulated with one or more of the additional therapeutically active component(s) as described elsewhere herein.

Administration Regimens

According to certain embodiments of the present invention, multiple doses of an anti-IL-33 antibody (or a pharmaceutical composition comprising a combination of an anti-IL-33 antibody and any of the additional therapeutically active agents mentioned herein) may be administered to a subject over a defined time course. The methods according to this aspect of the invention comprise sequentially administering to a subject multiple doses of an anti-IL-33 antibody of the invention. As used herein, "sequentially administering" means that each dose of anti-IL-33 antibody is administered to the subject at a different point in time, e.g., on different days separated by a predetermined interval (e.g., hours, days, weeks or months). The present invention includes methods which comprise sequentially administering to the patient a single initial dose of an anti-IL-33 antibody, followed by one or more secondary doses of the anti-IL-33 antibody, and optionally followed by one or more tertiary doses of the anti-IL-33 antibody.

The terms "initial dose," "secondary doses," and "tertiary doses," refer to the temporal sequence of administration of the anti-IL-33 antibody of the invention. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of anti-IL-33 antibody, but generally may differ from one another in terms of frequency of administration. In certain embodiments, however, the amount of anti-IL-33 antibody contained in the initial, secondary and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

In certain exemplary embodiments of the present invention, each secondary and/or tertiary dose is administered 1 to 26 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, 15, 15½, 16, 16½, 17, 17½, 18, 18½, 19, 19½, 20, 20½, 21, 21½, 22, 22½, 23, 23½, 24, 24½, 25, 25½, 26, 26½, or more) weeks after the immediately preceding dose. The phrase "the immediately preceding dose," as used herein, means, in a sequence of multiple administrations, the dose of anti-IL-33 antibody which is administered to a patient prior to the administration of the very next dose in the sequence with no intervening doses.

The methods according to this aspect of the invention may comprise administering to a patient any number of secondary and/or tertiary doses of an anti-IL-33 antibody. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In embodiments involving multiple secondary doses, each secondary dose may be administered at the same frequency as the other secondary doses. For example, each secondary dose may be administered to the patient 1 to 2 weeks or 1 to 2 months after the immediately preceding dose. Similarly, in embodiments involving multiple tertiary doses, each tertiary dose may be administered at the same frequency as the other tertiary doses. For example, each tertiary dose may be administered to the patient 2 to 12 weeks after the immediately preceding dose. In certain embodiments of the invention, the frequency at which the secondary and/or tertiary doses are administered to a patient can vary over the course of the treatment regimen. The frequency of administration may also be adjusted during the course of treatment by a physician depending on the needs of the individual patient following clinical examination.

The present invention includes administration regimens in which 2 to 6 loading doses are administered to a patient a first frequency (e.g., once a week, once every two weeks, once every three weeks, once a month, once every two months, etc.), followed by administration of two or more maintenance doses to the patient on a less frequent basis. For example, according to this aspect of the invention, if the loading doses are administered at a frequency of once a month, then the maintenance doses may be administered to the patient once every six weeks, once every two months, once every three months, etc.).

Diagnostic Uses of the Antibodies

The anti-IL-33 antibodies of the present invention may also be used to detect and/or measure IL-33, or IL-33-expressing cells in a sample, e.g., for diagnostic purposes. For example, an anti-IL-33 antibody, or fragment thereof, may be used to diagnose a condition or disease characterized by aberrant expression (e.g., over-expression, under-expression, lack of expression, etc.) of IL-33. Exemplary diagnostic assays for IL-33 may comprise, e.g., contacting a sample, obtained from a patient, with an anti-IL-33 antibody of the invention, wherein the anti-IL-33 antibody is labeled with a detectable label or reporter molecule. Alternatively, an unlabeled anti-IL-33 antibody can be used in diagnostic applications in combination with a secondary antibody which is itself detectably labeled. The detectable label or reporter molecule can be a radioisotope, such as $^{3}H$, $^{14}C$, $^{32}P$, $^{35}S$, or $^{125}I$; a fluorescent or chemiluminescent moiety such as fluorescein isothiocyanate, or rhodamine; or an enzyme such as alkaline phosphatase, beta-galactosidase, horseradish peroxidase, or luciferase. Specific exemplary assays that can be used to detect or measure IL-33 in a sample include enzyme-linked immunosorbent assay (ELISA), radioimmunoassay (RIA), and fluorescence-activated cell sorting (FACS).

Samples that can be used in IL-33 diagnostic assays according to the present invention include any tissue or fluid sample obtainable from a patient which contains detectable quantities of IL-33 protein, or fragments thereof, under normal or pathological conditions. Generally, levels of IL-33 in a particular sample obtained from a healthy patient (e.g., a patient not afflicted with a disease or condition associated with abnormal IL-33 levels or activity) will be measured to initially establish a baseline, or standard, level of IL-33. This baseline level of IL-33 can then be compared against the levels of IL-33 measured in samples obtained from individuals suspected of having a IL-33 related disease or condition.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Generation of Human Antibodies to Human IL-33

An immunogen comprising human IL-33 was administered directly, with an adjuvant to stimulate the immune response, to a VELOCIMMUNE® mouse comprising DNA encoding human Immunoglobulin heavy and kappa light chain variable regions. The antibody immune response was monitored by an IL-33-specific immunoassay. When a desired immune response was achieved splenocytes were harvested and fused with mouse myeloma cells to preserve their viability and form hybridoma cell lines. The hybridoma cell lines were screened and selected to identify cell lines that produce IL-33-specific antibodies. Using this technique several anti-IL-33 chimeric antibodies (i.e., antibodies possessing human variable domains and mouse constant domains) were obtained; exemplary antibodies generated in this manner were designated as follows: H1M9559N, H1M9566N, H1M9568N and H1M9565N. The human variable domains from the chimeric antibodies were subsequently cloned onto human constant domains to make fully human anti-IL-33 antibodies as described herein.

Anti-IL-33 antibodies were also isolated directly from antigen-positive B cells without fusion to myeloma cells, as described in US 2007/0280945A1. Using this method, several fully human anti-IL-33 antibodies (i.e., antibodies possessing human variable domains and human constant domains) were obtained; exemplary antibodies generated in this manner were designated as follows: H4H9629P, H4H9633P, H4H6940P, H4H9659P, H4H9660P, H4H9662P, H4H9663P, H4H9664P, H4H9665P, H4H9666P, H4H9667P, H4H9670P, H4H9671P, H4H9672P, H4H9675P, and H4H9676P.

Certain biological properties of the exemplary anti-IL-33 antibodies generated in accordance with the methods of this Example are described in detail in the Examples set forth below.

Example 2

Heavy and Light Chain Variable Region Amino Acid Sequences

Table 1 sets forth the heavy and light chain variable region amino acid sequence pairs, and CDR sequences, of selected anti-IL-33 antibodies and their corresponding antibody identifiers.

Antibodies are typically referred to herein according to the following nomenclature: Fc prefix (e.g. "H1 M," or "H4H"), followed by a numerical identifier (e.g. "9559," "9566," or "9629" as shown in Table 1), followed by a "P," or "N" suffix. Thus, according to this nomenclature, an antibody may be referred to herein as, e.g., "H1M9559N," "H1M9566N," "H4H9629P," etc. The H1M and H4H prefixes on the antibody designations used herein indicate the particular Fc region isotype of the antibody. For example, an "H1M" antibody has a mouse IgG1 Fc, whereas an "H4H" antibody has a human IgG4 Fc. As will be appreciated by a person of ordinary skill in the art, an antibody having a particular Fc isotype can be converted to an antibody with a different Fc isotype (e.g., an antibody with a mouse IgG1 Fc can be converted to an antibody with a human IgG4, etc.), but in any event, the variable domains (including the CDRs)—which are indicated by the numerical identifiers shown in Table 1—will remain the same, and the binding properties are expected to be identical or substantially similar regardless of the nature of the Fc domain.

Example 3

Antibody Binding to Human IL-33 as Determined by Surface Plasmon Resonance

Equilibrium dissociation constants ($K_D$ values) for IL-33 binding to purified anti-IL-33 monoclonal antibodies were determined using a real-time surface plasmon resonance biosensor using a Biacore 4000 instrument. The Biacore sensor surface was first derivatized by amine coupling with either a polyclonal rabbit anti-mouse antibody (GE, #BR-1008-38) or with a monoclonal mouse anti-human Fc antibody (GE, #BR-1008-39) to capture anti-IL-33 monoclonal antibodies expressed with mouse or with human IgG4 constant regions, respectively. All Biacore binding studies were performed in 0.01M ADA pH 7.4, 0.15M NaCl, 3 mM EDTA, and 0.05% v/v Surfactant Tween-20 (ABS-ET running buffer). Different concentrations of human IL-33 (hIL-33; R&D Systems, #3625-IL-010/CF) or cynomolgus monkey IL-33 expressed with a C-terminal hexahistidine tag (MfIL-33-6His; SEQ ID NO: 305) prepared in ABS-ET running buffer (ranging from 100 nM to 3.7 nM, 3-fold

TABLE 1

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| 9559N | 2 | 4 | 6 | 8 | 10 | 12 | 14 | 16 |
| 9566N | 18 | 20 | 22 | 24 | 26 | 28 | 30 | 32 |
| 9568N | 34 | 36 | 38 | 40 | 42 | 44 | 46 | 48 |
| 9629P | 50 | 52 | 54 | 56 | 58 | 60 | 62 | 64 |
| 9633P | 66 | 68 | 70 | 72 | 74 | 76 | 78 | 80 |
| 9640P | 82 | 84 | 86 | 88 | 90 | 92 | 94 | 96 |
| 9659P | 98 | 100 | 102 | 104 | 106 | 108 | 110 | 112 |
| 9660P | 114 | 116 | 118 | 120 | 122 | 124 | 126 | 128 |
| 9662P | 130 | 132 | 134 | 136 | 138 | 140 | 142 | 144 |
| 9663P | 146 | 148 | 150 | 152 | 154 | 156 | 158 | 160 |
| 9664P | 162 | 164 | 166 | 168 | 170 | 172 | 174 | 176 |
| 9665P | 178 | 180 | 182 | 184 | 186 | 188 | 190 | 192 |
| 9666P | 194 | 196 | 198 | 200 | 202 | 204 | 206 | 208 |
| 9667P | 210 | 212 | 214 | 216 | 218 | 220 | 222 | 224 |
| 9670P | 226 | 228 | 230 | 232 | 234 | 236 | 238 | 240 |
| 9671P | 242 | 244 | 246 | 248 | 250 | 252 | 254 | 256 |
| 9672P | 258 | 260 | 262 | 264 | 266 | 268 | 270 | 272 |
| 9675P | 274 | 276 | 278 | 280 | 282 | 284 | 286 | 288 |
| 9676P | 290 | 292 | 294 | 296 | 298 | 300 | 302 | 304 |
| 9565N | 308 | 310 | 312 | 314 | 316 | 318 | 320 | 322 | dilutions) were injected over the anti-IL-33 monoclonal antibody captured surface at a flow rate of 30 μL/minute. Association of either hIL-33 or MfIL-33-6His to the captured monoclonal antibody was monitored for 4 minutes and their dissociation in ABS-ET running buffer was monitored for 10 minutes. The effect of reduced pH on the binding of each anti-IL-33 antibody to either hIL-33 or MfIL-33-6His was studied using an in-line pH chase assay format in 0.01M ADA pH 6.0, 0.15M NaCl, 3 mM EDTA, and 0.05% v/v Surfactant Tween-20 (ABS-ET pH6 buffer). To achieve this, association of either hIL-33 or MfIL-33-6His to the captured monoclonal antibody was monitored for 4 minutes in ABS-ET running buffer. Following a 30 second dissociation of either hIL-33 or MfIL-33-6His in ABS-ET running buffer, ABS-ET pH6 buffer was injected for 3 minutes, and the analyte dissociation under the low-pH conditions was measured. All the binding kinetic experiments were performed at both 25° C. and 37° C. Kinetic association ($k_a$) and dissociation ($k_d$) constants were determined by fitting the real-time sensorgrams to a 1:1 binding model using Scrubber 2.0c curve fitting software. Binding dissociation equilibrium constants ($K_D$) and dissociative half-lives (t½) were calculated from the kinetic rate constants as:

$$K_D(M) = k_d/k_a \text{ and } t_{1/2}(\min) = \ln(2)/(60 * k_d)$$

Binding kinetic parameters for hIL-33 and MfIL-33-6His binding to different anti-IL-33 monoclonal antibodies at 25° C. and 37° C. are shown in Tables 2 through 5. At 25° C., hIL-33 bound to the anti-IL-33 antibodies with $K_D$ values ranging from 78 pM to 757 pM, as shown in Table 2. At 37° C., hIL-33 bound to the anti-IL-33 antibodies with $K_D$ values ranging from 411 pM to 2.03 nM, as shown in Table 3. At both 25° C. and 37° C., one anti-IL-33 antibody demonstrated weak binding and therefore its binding kinetic parameters could not be fit using an 1:1 binding model. At 25° C., MfIL-33-6His bound to the anti-IL-33 antibodies with $K_D$ values ranging from 333 pM to 38 nM, as shown in Table 4. At 37° C., MfIL-33-6His bound to the anti-IL-33 antibodies with $K_D$ values ranging from 1 nM to 48.6 nM, as shown in Table 5.

TABLE 2

Binding kinetic parameters of anti-IL-33 monoclonal antibodies binding to human IL-33 at 25° C.

| | Human IL-33 Binding Kinetics in ABS-ET Running Buffer | | | | In-Line Chase in ABS-ET pH 6 Buffer | | t½ Ratio |
|---|---|---|---|---|---|---|---|
| Antibody Captured | $k_a$ (1/Ms) | $k_d$ (1/s) | $K_D$ (M) | t½ (min) | $k_d$ (1/s) | t½ (min) | (pH 7.4/ pH 6.0) |
| H4H9675P | 1.02E+06 | 2.58E−04 | 2.54E−10 | 45 | 1.11E−03 | 10 | 4.3 |
| H4H9662P | 8.11E+05 | 2.50E−04 | 3.08E−10 | 46 | 8.26E−04 | 14 | 3.3 |
| H4H9640P | 9.12E+05 | 2.37E−04 | 2.60E−10 | 49 | 6.57E−04 | 18 | 2.8 |
| H4H9629P | 7.77E+05 | 2.26E−04 | 2.90E−10 | 51 | 1.28E−03 | 9 | 5.7 |
| H4H9659P | 5.26E+05 | 1.72E−04 | 3.27E−10 | 67 | 6.64E−04 | 17 | 3.9 |
| H4H9660P | 6.96E+05 | 2.24E−04 | 3.22E−10 | 52 | 7.08E−04 | 16 | 3.2 |
| H4H9667P | 6.37E+05 | 2.52E−04 | 3.95E−10 | 46 | 5.66E−04 | 20 | 2.2 |
| H4H9670P | 7.86E+05 | 2.89E−04 | 3.68E−10 | 40 | 8.25E−04 | 14 | 2.9 |
| H4H9663P | 1.36E+06 | 4.14E−04 | 3.05E−10 | 28 | 1.10E−03 | 11 | 2.7 |
| H4H9666P | 5.08E+05 | 2.80E−04 | 5.51E−10 | 41 | 1.34E−03 | 9 | 4.8 |
| H4H9676P | 1.03E+06 | 3.45E−04 | 3.34E−10 | 33 | 1.21E−03 | 10 | 3.5 |
| H4H9633P | 6.56E+05 | 2.83E−04 | 4.32E−10 | 41 | 8.10E−04 | 14 | 2.9 |
| H4H9671P | 7.71E+05 | 3.49E−04 | 4.53E−10 | 33 | 1.62E−03 | 7 | 4.6 |
| H4H9672P | 6.68E+05 | 3.52E−04 | 5.27E−10 | 33 | 1.41E−03 | 8 | 4.0 |
| H4H9665P | 8.88E+05 | 4.74E−04 | 5.33E−10 | 24 | 2.12E−03 | 5 | 4.5 |
| H4H9664P | 3.39E+05 | 2.57E−04 | 7.57E−10 | 45 | 8.23E−04 | 14 | 3.2 |
| H1M9568N | 7.02E+05 | 1.30E−04 | 1.84E−10 | 89 | 1.78E−04 | 65 | 1.4 |
| H1M9566N | 1.27E+05 | 1.00E−05** | 7.88E−11** | 1155** | 1.10E−04 | 105 | 11.0 |
| H1M9559N | 4.04E+05 | 2.74E−04 | 6.78E−10 | 42 | 1.87E−04 | 62 | 0.7 |
| H1M9565N | IC* | IC* | IC* | IC* | IC* | IC* | IC* |

*IC: inconclusive since very weak binding was observed under the experimental conditions and the real-time binding data could not be reliably fit into the 1:1 binding model.
**Under the experimental conditions no dissociation of IL33 from the captured monoclonal antibody was observed' therefore the value of $k_d$ was fixed to 1.00E−05, and the derived t½ and $K_D$ values represent lower and upper limits, respectively.

TABLE 3

Binding kinetic parameters of anti-IL-33 monoclonal antibodies binding to human IL-33 at 37° C.

| | Human IL-33 Binding Kinetics in ABS-ET Running Buffer | | | | In-Line Chase in ABS-ET pH 6 Buffer | | t½ Ratio |
|---|---|---|---|---|---|---|---|
| Antibody Captured | $k_a$ (1/Ms) | $k_d$ (1/s) | $K_D$ (M) | t½ (min) | $k_d$ (1/s) | t½ (min) | (pH 7.4/ pH 6.0) |
| H4H9675P | 2.12E+06 | 8.72E−04 | 4.11E−10 | 13 | 4.63E−03 | 2 | 5.3 |
| H4H9662P | 1.40E+06 | 6.20E−04 | 4.43E−10 | 19 | 3.83E−03 | 3 | 6.2 |

TABLE 3-continued

Binding kinetic parameters of anti-IL-33 monoclonal antibodies binding to human IL-33 at 37° C.

| | Human IL-33 Binding Kinetics in ABS-ET Running Buffer | | | | In-Line Chase in ABS-ET pH 6 Buffer | | $t\frac{1}{2}$ Ratio |
|---|---|---|---|---|---|---|---|
| Antibody Captured | $k_a$ (1/Ms) | $k_d$ (1/s) | $K_D$ (M) | $t\frac{1}{2}$ (min) | $k_d$ (1/s) | $t\frac{1}{2}$ (min) | (pH 7.4/ pH 6.0) |
| H4H9640P | 1.15E+06 | 5.73E−04 | 4.98E−10 | 20 | 2.65E−03 | 4 | 4.6 |
| H4H9629P | 1.27E+06 | 6.46E−04 | 5.08E−10 | 18 | 5.82E−03 | 2 | 9.0 |
| H4H9659P | 7.07E+05 | 4.03E−04 | 5.70E−10 | 29 | 2.99E−03 | 4 | 7.4 |
| H4H9660P | 8.03E+05 | 4.79E−04 | 5.96E−10 | 24 | 3.23E−03 | 4 | 6.8 |
| H4H9667P | 9.76E+05 | 6.03E−04 | 6.18E−10 | 19 | 2.44E−03 | 5 | 4.0 |
| H4H9670P | 1.16E+06 | 7.83E−04 | 6.76E−10 | 15 | 3.83E−03 | 3 | 4.9 |
| H4H9663P | 1.83E+06 | 1.24E−03 | 6.77E−10 | 9 | 4.62E−03 | 3 | 3.7 |
| H4H9666P | 1.13E+06 | 7.70E−04 | 6.81E−10 | 15 | 6.80E−03 | 2 | 8.8 |
| H4H9676P | 1.38E+06 | 1.28E−03 | 9.22E−10 | 9 | 5.24E−03 | 2 | 4.1 |
| H4H9633P | 7.40E+05 | 6.89E−04 | 9.31E−10 | 17 | 2.40E−03 | 5 | 3.5 |
| H4H9671P | 1.21E+06 | 1.14E−03 | 9.38E−10 | 10 | 5.85E−03 | 2 | 5.1 |
| H4H9672P | 1.09E+06 | 1.15E−03 | 1.05E−09 | 10 | 5.41E−03 | 2 | 4.7 |
| H4H9665P | 1.21E+06 | 1.44E−03 | 1.19E−09 | 8 | 9.65E−03 | 1 | 6.7 |
| H4H9664P | 5.19E+05 | 7.21E−04 | 1.39E−09 | 16 | 2.79E−03 | 4 | 3.9 |
| H1M9568N | 6.72E+05 | 9.61E−04 | 1.43E−09 | 12 | 1.10E−03 | 10 | 1.1 |
| H1M9566N | 1.66E+05 | 2.83E−04 | 1.70E−09 | 41 | 9.67E−04 | 12 | 3.4 |
| H1M9559N | 4.73E+05 | 9.62E−04 | 2.03E−09 | 12 | 9.92E−04 | 12 | 1.0 |
| H1M9565N | IC* | IC* | IC* | IC* | IC* | IC* | IC* |

*IC: inconclusive since very weak binding was observed under the experimental conditions and the real-time binding data could not be reliably fit into the 1:1 binding model.

TABLE 4

Binding kinetic parameters of anti-IL-33 monoclonal antibodies binding to MfIL-33-6His at 25° C.

| | MfIL-33-6His Binding Kinetics in ABS-ET Running Buffer | | | | In-Line Chase in ABS-ET pH 6 Buffer | | $t\frac{1}{2}$ Ratio |
|---|---|---|---|---|---|---|---|
| Antibody Captured | $k_a$ (1/Ms) | $k_d$ (1/s) | $K_D$ (M) | $t\frac{1}{2}$ (min) | $k_d$ (1/s) | $t\frac{1}{2}$ (min) | (pH 7.4/ pH 6.0) |
| H4H9675P | 5.06E+05 | 1.29E−03 | 2.55E−09 | 9 | 1.56E−03 | 7 | 1.2 |
| H4H9662P | 3.53E+05 | 4.42E−04 | 1.25E−09 | 26 | 1.17E−04 | 99 | 0.3 |
| H4H9640P | 4.50E+05 | 1.37E−03 | 3.06E−09 | 8 | 5.01E−04 | 23 | 0.4 |
| H4H9629P | 5.62E+05 | 1.35E−02 | 2.39E−08 | 0.9 | 3.58E−02 | 0.3 | 2.7 |
| H4H9659P | 3.25E+05 | 4.86E−04 | 1.50E−09 | 24 | 1.23E−04 | 94 | 0.3 |
| H4H9660P | 4.26E+05 | 1.49E−03 | 3.49E−09 | 8 | 1.08E−03 | 11 | 0.7 |
| H4H9667P | 3.43E+05 | 9.91E−04 | 2.89E−09 | 12 | 6.96E−04 | 17 | 0.7 |
| H4H9670P | 4.40E+05 | 2.10E−03 | 4.77E−09 | 6 | 3.93E−04 | 29 | 0.2 |
| H4H9663P | 8.69E+05 | 9.25E−04 | 1.06E−09 | 12 | 6.83E−04 | 17 | 0.7 |
| H4H9666P | 2.22E+05 | 3.54E−03 | 1.59E−08 | 3.3 | 8.09E−03 | 1.4 | 2.3 |
| H4H9676P | 8.52E+05 | 4.12E−03 | 4.84E−09 | 2.8 | 1.45E−03 | 8 | 0.4 |
| H4H9633P | 2.62E+05 | 9.97E−03 | 3.80E−08 | 1.2 | 2.87E−03 | 4 | 0.3 |
| H4H9671P | 5.87E+05 | 1.50E−03 | 2.55E−09 | 8 | 1.61E−03 | 7 | 1.1 |
| H4H9672P | 4.37E+05 | 3.60E−03 | 8.22E−09 | 3.2 | 2.67E−03 | 4 | 0.7 |
| H4H9665P | 5.57E+05 | 5.66E−04 | 1.02E−09 | 20 | 7.53E−04 | 15 | 1.3 |
| H4H9664P | 1.40E+05 | 1.65E−03 | 1.18E−08 | 7 | 4.80E−04 | 24 | 0.3 |
| H1M9568N | 2.44E+05 | 2.61E−04 | 1.07E−09 | 44 | 3.02E−04 | 38 | 1.2 |
| H1M9566N | 2.93E+05 | 9.75E−05 | 3.33E−10 | 119 | 1.26E−04 | 91 | 1.3 |
| H1M9559N | 3.21E+05 | 1.23E−03 | 3.82E−09 | 9 | 1.52E−03 | 8 | 1.2 |
| H1M9565N | 4.06E+04 | 7.20E−05 | 1.77E−09 | 160 | 1.43E−04 | 81 | 2.0 |

TABLE 5

Binding kinetic parameters of anti-IL-33 monoclonal antibodies binding to MfIL-33-6His at 37° C.

| Antibody Captured | MfIL-33-6His Binding Kinetics in ABS-ET Running Buffer | | | | In-Line Chase in ABS-ET pH 6 Buffer | | $t_{1/2}$ Ratio (pH 7.4/ pH 6.0) |
|---|---|---|---|---|---|---|---|
| | $k_a$ (1/Ms) | $k_d$ (1/s) | $K_D$ (M) | $t_{1/2}$ (min) | $k_d$ (1/s) | $t_{1/2}$ (min) | |
| H4H9675P | 1.02E+06 | 4.91E−03 | 4.81E−09 | 2.4 | 7.35E−03 | 1.6 | 1.5 |
| H4H9662P | 7.07E+05 | 1.58E−03 | 2.24E−09 | 7 | 1.68E−03 | 7 | 1.1 |
| H4H9640P | 8.10E+05 | 4.36E−03 | 5.38E−09 | 2.6 | 2.26E−03 | 5 | 0.5 |
| H4H9629P | 1.07E+06 | 3.47E−02 | 3.24E−08 | 0.3 | FT* | FT* | FT* |
| H4H9659P | 5.98E+05 | 1.86E−03 | 3.11E−09 | 6 | 1.02E−03 | 11 | 0.5 |
| H4H9660P | 6.80E+05 | 4.44E−03 | 6.53E−09 | 2.6 | 4.63E−03 | 2.5 | 1.0 |
| H4H9667P | 6.81E+05 | 3.17E−03 | 4.66E−09 | 4 | 2.68E−03 | 4 | 0.8 |
| H4H9670P | 7.35E+05 | 5.03E−03 | 6.84E−09 | 2.3 | 1.65E−03 | 7 | 0.3 |
| H4H9663P | 1.62E+06 | 3.61E−03 | 2.22E−09 | 3.2 | 3.54E−03 | 3.3 | 1.0 |
| H4H9666P | 4.32E+05 | 1.41E−02 | 3.27E−08 | 0.8 | FT* | FT* | FT* |
| H4H9676P | 1.87E+06 | 1.44E−02 | 7.70E−09 | 0.8 | FT* | FT* | FT* |
| H4H9633P | 4.68E+05 | 2.27E−02 | 4.86E−08 | 0.5 | FT* | FT* | FT* |
| H4H9671P | 1.20E+06 | 6.07E−03 | 5.08E−09 | 1.9 | 8.19E−03 | 1.4 | 1.3 |
| H4H9672P | 9.46E+05 | 1.30E−02 | 1.37E−08 | 0.9 | FT* | FT* | FT* |
| H4H9665P | 1.10E+06 | 2.10E−03 | 1.91E−09 | 5 | 4.00E−03 | 2.9 | 1.9 |
| H4H9664P | 3.61E+05 | 5.84E−03 | 1.62E−08 | 2.0 | 1.93E−03 | 6 | 0.3 |
| H1M9568N | 3.89E+05 | 1.73E−03 | 4.46E−09 | 7 | 2.24E−03 | 5 | 1.3 |
| H1M9566N | 3.99E+05 | 4.00E−04 | 1.00E−09 | 29 | 1.15E−03 | 10 | 2.9 |
| H1M9559N | 4.93E+05 | 3.47E−03 | 7.04E−09 | 3.3 | 3.07E−03 | 4 | 0.9 |
| H1M9565N | 7.82E+04 | 2.02E−04 | 2.59E−09 | 57 | 2.28E−04 | 51 | 1.1 |

*FT: fast $t_{1/2}$.

Example 4

Anti-IL-33 Antibodies Block Binding of IL-33 to the Human ST2 Receptor

The ability of anti-IL-33 antibodies to block either human IL-33 (hIL-33) or cynomologus monkey IL-33 binding to the human ST2 receptor was measured using a competition sandwich ELISA. A portion of human ST2 protein ecto domain that was expressed with a C-terminal human IgG1 Fc tag (hST2-hFc; SEQ ID NO:306), was coated at a concentration of 1 µg/ml in PBS buffer on a 96-well microtiter plate overnight at 4° C. Nonspecific binding sites were subsequently blocked using a 0.5% (w/v) solution of BSA in PBS. Constant concentrations of either 30 pM biotinylated hIL-33 protein (R&D systems, Cat #3625-IL/CF) (biotin-hIL-33) or 150 pM cynomologus monkey IL-33 expressed with hexahistidine tag (MfIL-33-6His; SEQ ID NO:305) were separately added to serial dilutions of antibodies so that the final concentrations of antibodies ranged from 0 to 100 nM. The antibody/IL-33 mixtures were incubated for 1 hour at room temperature before they were transferred to the hST2-hFc-coated microtiter plates. After incubating for 1 hour at room temperature, the wells were then washed, and plate-bound biotin-hIL-33 was detected with streptavidin conjugated with horse-radish peroxidase (HRP) (Thermo Scientific, Cat #N200), and plate-bound MfIL-33-6His was detected with a HRP conjugated anti-His monoclonal antibody (Qiagen, #34460). All samples were developed with a TMB solution (BD biosciences, #51-2607KC) to produce a colorimetric reaction and then quenched by acidification with 1M sulfuric acid before measuring absorbance at 450 nm on a Victor X5 plate reader. Data analysis was performed using a sigmoidal dose-response model within Prism™ software. The calculated $IC_{50}$ value, defined as the concentration of antibody required to reduce by 50% from maximal signal the biotin-hIL-33 or MfIL-33-6His binding to plate-coated hST2-hFc, was used as an indicator of blocking potency. Percent blockade was calculated as the ratio of the reduction in signal observed in the presence of antibody relative to the difference between the signal with IL-33 alone and background (signal from HRP-conjugated secondary antibody or streptavidin alone). The absorbance measured for the constant concentration of biotin-hIL-33 or MfIL-33-6His alone is defined as 0% blocking and the absorbance measured for no added IL-33 is defined as 100% blocking. The absorbance values of the wells containing the highest concentration for each antibody were used to determine the percent maximum blocking.

TABLE 6

ELISA blocking of biotin-hIL-33 or MfIL-33-6His binding to hST2-hFc by anti-IL-33 antibodies

| Ab ID | Blocking 30 pM biotin-hIL-33 on hST2-hFc, $IC_{50}$ (M) | % Maximum blocking biotin-hIL-33 on hST2-hFc | Blocking 150 pM Mf-IL-33-6His on hST2-hFc, $IC_{50}$ (M) | % Maximum blocking Mf-IL-33-6His on hST2-hFc |
|---|---|---|---|---|
| H1M9559N* | 1.4E−10 | 88 | 1.0E−08 | 53 |
| H1M9566N* | 3.2E−10 | 69 | 2.2E−10 | 41 |
| H1M9565N* | 2.2E−08 | 68 | 1.2E−08 | 86 |
| H1M9568N* | 1.9E−10 | 55 | 8.4E−10 | 38 |
| H4H9629P | 4.5E−10 | 80 | N/A | NBl |
| H4H9633P | 4.4E−10 | 66 | N/A | NBl |
| H4H9640P | 3.5E−10 | 78 | 3.5E−09 | 73 |
| H4H9659P | 4.0E−10 | 78 | 6.0E−10 | 92 |
| H4H9660P | 3.1E−10 | 57 | 4.2E−09 | 68 |
| H4H9662P | 1.0E−09 | 77 | 8.6E−10 | 87 |
| H4H9663P | 5.0E−10 | 74 | 1.2E−09 | 81 |
| H4H9664P | 3.0E−10 | 73 | 3.8E−09 | 67 |
| H4H9665P | 8.7E−10 | 55 | 4.2E−10 | 81 |
| H4H9666P | 6.0E−10 | 71 | 1.3E−08 | 40 |

TABLE 6-continued

ELISA blocking of biotin-hIL-33 or MfIL-33-6His
binding to hST2-hFc by anti-IL-33 antibodies

| Ab ID | Blocking 30 pM biotin-hIL-33 on hST2-hFc, IC$_{50}$ (M) | % Maximum blocking biotin-hIL-33 on hST2-hFc | Blocking 150 pM Mf-IL-33-6His on hST2-hFc, IC$_{50}$ (M) | % Maximum blocking Mf-IL-33-6His on hST2-hFc |
|---|---|---|---|---|
| H4H9667P | 4.1E−10 | 78 | 4.1E−09 | 72 |
| H4H9670P | 4.8E−10 | 69 | 3.5E−09 | 69 |
| H4H9671P | 4.6E−10 | 46 | 5.8E−09 | 62 |
| H4H9672P | 4.4E−10 | 63 | 5.5E−09 | 48 |
| H4H9675P | 4.4E−10 | 58 | 1.5E−09 | 72 |
| H4H9676P | 4.6E−10 | 54 | 3.2E−09 | 57 |

N/A = not applicable
NB1 = non-blocker
*= Experiment performed on a separate day Binding experiments for 20 antibodies were performed on two separate days, as indicated in Table 6. All 20 of the anti-IL-33 antibodies blocked biotin-hIL-33 binding to hST2-hFc with IC$_{50}$ values ranging from 140 pM to 22nM and percent maximum blocking ranging from 46% to 88%. Eighteen of the 20 anti-IL-33 antibodies blocked MfIL-33-6His binding to hST2-hFc with IC$_{50}$ values ranging from 220 pM to 13 nM and percent maximum blocking ranging from 38% to 92%, as shown in Table 6. Two of the antibodies tested, H4H9629P and H4H9633P, did not demonstrate measurable blockade of MfIL-33-6His binding to hST2-hFc.

Example 5

Inhibition of IL-33 Binding to Anti-IL-33 Monoclonal Antibody by ST2 as Shown by Biacore Analysis The ability of anti-IL-33 antibodies to bind to a pre-formed complex of IL-33 with ST2 was tested using Biacore T-200 instrument equipped with a real-time surface plasmon resonance biosensor. The experiment was performed at 25° C. with a running buffer composed of 0.01M HEPES pH 7.4, 0.15M NaCl, 3 mM EDTA, and 0.05% v/v Surfactant Tween-20 (HBS-ET). The Biacore sensor surface was first derivatized by amine coupling an anti-myc tag-specific monoclonal antibody (Clone #9E10), and on this derivatized sensor was captured approximately 160 response units (RU) of human ST2 protein expressed with a C-terminal myc-myc-hexahistadine tag (hST2-MMH; SEQ ID NO: 323). The captured hST2-MMH surface was then saturated by injecting 100 nM of human IL-33 (hIL-33; R&D Systems, #3625-IL-010/CF) for 3 minutes followed by a 3 minute injection of a 100 nM solution of the anti-IL-33 monoclonal antibody. The real-time binding response was monitored during the entire course of the experiment, and the observed binding response at 3 minutes after injection of anti-IL-33 antibody to the pre-formed complex of hIL-33 and captured hST2-MMH was recorded and tabulated and shown in Table 7. No non-specific binding of anti-IL-33 monoclonal antibody to the anti-myc tag capture surface was observed. As shown in Table 7, 17 of the tested antibodies did not show measurable binding to hIL-33 after it was pre-complexed with hST2-MMH, while three antibodies (H1M9565N, H1M9566N, and H1M9568N) bound to hIL-33 after it was pre-complexed with hST2-MMH.

TABLE 7

Binding of anti-IL-33 antibodies to a pre-formed complex of hIL-33 and hST2-MMH

| Antibody | Antibody Binding Response (RU) |
|---|---|
| H4H9629P | −1 |
| H4H9633P | −1 |
| H4H9640P | −1 |
| H4H9659P | −1 |
| H4H9660P | −1 |
| H4H9662P | 0 |
| H4H9663P | −1 |
| H4H9664P | −1 |
| H4H9665P | 0 |
| H4H9666P | −1 |
| H4H9667P | −1 |
| H4H9670P | −1 |
| H4H9671P | −1 |
| H4H9672P | −1 |
| H4H9675P | −1 |
| H4H9676P | −1 |
| H1M9559N | −4 |
| H1M9565N | 11 |
| H1M9566N | 13 |
| H1M9568N | 131 |

Example 6

Inhibition of IL-33-Mediated Receptor Signaling by Anti-IL-33 Antibodies

Interleukin-33 (IL-33) is a ligand for ST2, a toll-like/interleukin-1 receptor super-family member that associates with an accessory protein, IL-1RAcP (for review, see Kakkar and Lee, 2008). Upon activation of ST2/IL-1RAcP by IL-33, a signaling cascade is triggered through downstream molecules such as MyD88 (myeloid differentiation factor 88) and TRAF6 (TNF receptor associated factor 6), leading to activation of NFκB (nuclear factor—κB), among others. To develop a biologically relevant bioassay system to test anti-IL-33 antibodies, human embryonic kidney cells (HEK293) were stably transfected to express human ST2 (amino acids 1-556 of accession number NP_057316) along with a luciferase reporter [NFκB response element (5x)-luciferase-IRES-GFP] (HEK293/hST2/NFkB-luciferase cell line). The HEK293 cell line expresses IL-1RAcP endogenously and NFκB activation by IL-33 in HEK293 cells has been shown previously (Schmitz et al., *Immunity* 23:479-490 (2005)). The stable cell line was isolated and maintained in 10% FBS, DMEM, NEAA, penicillin/streptomycin, and G418.

For the bioassay, HEK293/hST2/NFkB-luciferase cells were seeded onto 96-well assay plates at 10,000 cells per well in low serum media containing 0.1% w/v FBS and OPTIMEM (Invitrogen, #31985-070) and then incubated at 37° C. in 5% CO$_2$ overnight. The next day, to determine the dose response of IL-33, either human IL-33 (hIL-33; R&D Systems, #3625-IL) or cynomolgus monkey IL-33 expressed with a C-terminal hexahistidine tag (MfIL-33-6His; SEQ ID NO:305) were serially diluted at 1:3 and added to the cells starting from 10 nM and ranging down to 0.0002 nM, plus a control sample containing no IL-33. To measure inhibition, antibodies were serially diluted and added to the cells followed by addition of constant concentrations of IL-33 (10 pM hIL-33 for the human assay and 5 pM MfIL-33-6His for the monkey assay). Three-fold antibody serial dilutions were performed before adding to the cells, starting from 100 pM and ranging down to 0.002 nM or starting from 10 nM and ranging down to 0.0002 nM. In addition to the antibody dilution series, a well containing the constant concentration of IL-33 but without any antibody was also included. After 5.5 hours of incubation at 37° C. in 5% $CO_2$, luciferase activity was detected using a Victor X (Perkin Elmer) plate reader, and the results were analyzed using nonlinear regression (4-parameter logistics) with Prism 5. Results are shown in Table 8.

Peripheral blood mononuclear cells (PBMC) were purified from fresh whole blood from two different human donors by density gradient centrifugation. K2 EDTA whole blood was diluted 1:1 in RPMI 1640, carefully layered over Ficoll-Paque (GE Healthcare, #17-1440-03) and centrifuged to separate PBMC. The interphase layer containing the PBMC was aspirated, transferred to a new tube, and washed twice with MACS buffer that was comprised of a 1:20 dilution of the MACS BSA solution (Militenyi Biotec, #130-091-376)

TABLE 8

Inhibition of human IL-33 and monkey IL-33 activation of HEK293/hST2/NFkB-luciferase cells by anti-IL33 antibodies

| Species | | | | | | | |
|---|---|---|---|---|---|---|---|
| Human | | | | Monkey | | | |
| $EC_{50}$ [M] | | | | | | | |
| 2.2E-12 | | 3.5E-12 | 2.4E-11 | 8.2E-13 | | 3.5E-12 | |
| Constant IL-33 | | | | | | | |
| 10 pM hIL-33 | | | | 5 pM MfIL-33-6His | | | |
| AbPID | $IC_{50}$ [M] | Notes | $IC_{50}$ [M] | $IC_{50}$ [M] | $IC_{50}$ [M] | Notes | $IC_{50}$ [M] |
| H1M9559N | 2.0E-09 | | | | 4.9E-08 | | |
| H1M9566N | 9.5E-10 | Partial Inhibition (Max at 66%) | | | 1.5E-09 | Partial Inhibition (Max at 61%) | |
| H1M9565N | 2.9E-08 | | | | 1.7E-08 | | |
| H1M9568N | 2.5E-10 | Partial Inhibition (Max at 48%) | | | 3.5E-09 | Partial Inhibition (Max at 34%) | |
| H4H9629P | | | | 1.3E-11 | | | 5.5E-08 |
| H4H9633P | | | 2.2E-10 | | | | 1.3E-07 |
| H4H9640P | | | 3.0E-11 | | | | 1.4E-08 |
| H4H9659P | | | 4.7E-11 | | | | 3.3E-09 |
| H4H9660P | | | 3.5E-11 | | | | 1.9E-08 |
| H4H9662P | | | 2.0E-11 | | | | 1.5E-09 |
| H4H9663P | | | 1.3E-10 | | | | 2.7E-09 |
| H4H9664P | | | 5.0E-11 | | | | 2.6E-08 |
| H4H9665P | | | 9.0E-11 | | | | 6.6E-10 |
| H4H9666P | | | 3.5E-11 | | | | 7.8E-08 |
| H4H9667P | | | 7.1E-11 | | | | 1.2E-08 |
| H4H9670P | | | 1.2E-10 | | | | 1.7E-08 |
| H4H9671P | | | 2.5E-11 | | | | 4.8E-09 |
| H4H9672P | | | 2.5E-11 | | | | 2.0E-08 |
| H4H9675P | | | | 7.5E-12 | | | 4.1E-09 |
| H4H9676P | | | 3.5E-11 | | | | 8.4E-09 |

Eighteen of the 20 anti-IL33 antibodies blocked human IL-33 stimulation of the HEK293/hST2/NFkB-luciferase cells with $IC_{50}$ values ranging from 7.5 pM to 29 nM, as shown in Table 8. Two of the antibodies tested, H1M9566N and H1M9568N, partially inhibited hIL-33 with a maximum inhibition of 48% and 66%, with $IC_{50}$ values of 950 pM and 250 pM, respectively. Eighteen of the 20 anti-IL33 antibodies blocked MfIL-33-6His stimulation of HEK293/hST2/ NFkB-luciferase cells with $IC_{50}$ values ranging from 660 pM to 130 nM as shown in Table 8. Two of the antibodies tested, H1M9566N and H1M9568N, partially inhibited MfIL-33-6His with a maximum inhibition of 61% and 34%, with $IC_{50}$ values of 1.5 nM and 3.5 nM, respectively.

Example 7

Inhibition of IL-33-Induced Degranulation of Human Basophils by Anti-IL-33 Antibodies To further assess the in vitro characteristics of select anti-IL-33 antibodies of the invention, their ability to block IL-33-induced basophil degranulation was measured.

in MACS rinsing solution (Militenyi Biotec, #130-091-222). The purified PBMC were then plated in a v-bottom 96-well plate at a final concentration of ~3.0×10⁶ cells/mL in 100 μL of MACS buffer. To prime the basophils contained within the PBMC population, 1 ng of IL-3 (Sigma, #H7166-10UG) in 50 μL Dulbecco's Phosphate-Buffered Saline without $Ca^{++}$ or $Mg^{++}$ (DPBS) was added to the cell suspension, and then incubated at 37° C. for 10 minutes.

Serial dilutions (1:3) of two different exemplary anti-IL-33 antibodies of the invention (H4H9675P and H4H9659P) or an isotype control antibody were made, ranging from 10 nM to 4.6 pM, plus a control with no antibody. The solutions were mixed with a fixed concentration of 100 pM (final concentration) of human IL-33 (R&D Systems, #3625-IL/ CF) or no IL-33 negative control prior to adding to the PBMC. All conditions were tested in duplicate.

After addition of the human IL-33 and antibodies to the cells, the cells were incubated at 37° C. for 20 minutes to facilitate basophil degranulation. Degranulation was then stopped by cooling the assay plates on wet ice for 5 minutes. To enable analysis of the basophil population used to measure degranulation, 20 μL each (as per the manufacturer's instructions) of anti-HLA-DR-FITC (Beckman Coulter, #IM0463U), anti-CD123-APC (BD, #560087), and anti-CD203c-PE (Beckman Coulter, #IM3575) were added to each sample, and the samples were held at 4° C. for 20 minutes in the dark. The cells were then centrifuged, washed with DPBS, and then resuspended in 2% formaldehyde (fixation buffer) at 4° C. The next day, fixed cells were analyzed on a BD FACSCanto II to determine levels of basophil degranulation. Results are summarized in Tables 9 and 10.

TABLE 9

Percent degranulation of human basophils induced by human IL-33 challenge

| Donor | 100 pM IL-33 | | No IL-33 | |
|---|---|---|---|---|
| | Mean | SD | Mean | SD |
| 655687 | 68.800 | 2.263 | 10.295 | 0.856 |
| 655688 | 61.600 | 0.849 | 9.915 | 0.969 |

TABLE 10

Anti-IL-33 antibody blocking human IL-33 induced degranulation of human basophils

| Antibody | Donor 655687 $IC_{50}$ (M) | Donor 655688 $IC_{50}$ (M) |
|---|---|---|
| H4H9675P | 1.329E-10 | 9.712E-11 |
| H4H9659P | 5.786E-10 | 4.465E-10 |
| Isotype Control | non-blocking | non-blocking |

As shown in Table 9, at 100 pM, human IL-33 induced basophil degranulation in two different donors with a mean percent degranulation of 68.8% for donor 655687 and 61.6% for donor 655688.

As shown in Table 10, one anti-IL33 antibody, H4H9675P, blocked basophil degranulation induced by 100 pM human IL-33 challenge with an $IC_{50}$ value of 132.9 pM for donor 655687, and an $IC_{50}$ value of 97.12 pM for donor 655688. Another anti-IL33 antibody, H4H9659P, blocked basophil degranulation induced by 100 pM human IL-33 challenge with an $IC_{50}$ value of 578.6 pM for donor 655687, and an $IC_{50}$ value of 446.5 pM for donor 655688. In contrast, the isotype control did not block basophil degranulation from any of the tested donors.

Example 8

Inhibition of IL-33-Induced IFN-Gamma From Human PBMCs by Anti-IL-33

Antibodies

To further characterize anti-IL-33 antibodies of the invention, a primary cell based assay using peripheral blood mononuclear cells (PBMCs) was utilized. The assay used in this Example was based on the results published by Smithgall et al. in International Immunology, 2008, vol. 20 (8) pp. 1019-1030. For this assay, PBMCs were purified from fresh whole blood from three different donors by density gradient centrifugation. Briefly, K2 EDTA whole blood was diluted two-fold in RPMI 1640, carefully layered over Ficoll-Paque (GE Healthcare, #17-1440-03) and centrifuged for 20 minutes. The interphase layer containing the PBMCs was aspirated, transferred to a new tube, and washed twice with PBS. The isolated PBMCs were plated in round-bottom 96-well plates at a final concentration of $5 \times 10^5$ cells/mL in RPMI 1640 supplemented with 10% FBS, 2 mM L-glutamine, 100 U/mL penicillin, and 100 pg/mL streptomycin. Cells were then incubated with 50 g/mL of human IL-12 (hIL-12; R&D Systems, #219-IL-025/CF) and a serial dilution of human IL-33 (hIL-33; R&D Systems, #3625-IL-010/CF) alone from 10 nM to 0.64 pM, or with 260 pM of hIL-33 in combination with serial dilutions of antibodies from 100 nM to 6.4 pM. The final volume was 200 µL per well. Each condition was tested in triplicate. When antibodies were present, they were added to the cells after 30 minutes of pre-incubation with hIL-33.

The cells were incubated overnight at 37° C. in a humidified incubator with 5% $CO_2$, and then IFNγ levels in the culture supernatant were measured by ELISA (R&D Systems, #DY285). For the ELISA, 96-well flat-bottom plates were coated with the capture antibody, according to the manufacturer's instructions. After washing and blocking, 100 µL of undiluted culture supernatant was added to the plates and incubated for 2 hours. Subsequent washes and detection were done following the manufacturer's instructions.

Human IL-33, in the presence of hIL-12, induced the release of IFNγ from human total PBMC from the three different donors tested, with $EC_{50}$ values between 274 pM to 39 pM as shown in Table 11. Eleven anti-IL-33 antibodies were tested using PBMCs from donors #603486 and #603487, while 3 anti-IL-33 antibodies were tested with PBMCs from donor #603491. All 11 of the anti-IL-33 antibodies tested on donors #603486 and #603487 blocked the release of IFNγ from human PBMC induced by 260pM IL-33, with $IC_{50}$ values ranging from 175 pM to 22 nM, as shown in Table 12. None of the three IL-33 antibodies tested on donor #603491 blocked the release of IFNγ from human PBMC induced by 260 pM hIL-33 and instead caused an increase of IFNγ release with $EC_{50}$ values between 56.1 pM and 189 nM.

TABLE 11 hIL-33 induced IFNγ release from human PBMC from three donors.

| [IL-33] | Donor 603486 | Donor 603487 | Donor 603491 |
|---|---|---|---|
| $EC_{50}$ (M) | 1.101E-10 | 3.878E-11 | 2.739E-10 |

TABLE 12

Anti-IL-33 antibodies blocking IL-33 induced IFN-γ release from human PBMC from donor #603486 and #603487

| Antibody | Donor #603486 $IC_{50}$ (M) | Donor #603487 $IC_{50}$ (M) |
|---|---|---|
| H4H9629P | 8.154E-10 | 5.205E-09 |
| H4H9640P | 4.419E-09 | 1.224E-08 |
| H4H9659P | 1.252E-09 | 2.710E-09 |
| H4H9660P | 6.669E-10 | 2.913E-09 |
| H4H9662P | 9.640E-10 | 3.021E-09 |
| H4H9663P | 1.236E-08 | 2.203E-08 |
| H4H9664P | 3.984E-09 | 6.081E-09 |
| H4H9665P | 1.044E-08 | 2.337E-08 |
| H4H9667P | 8.066E-09 | 1.876E-08 |
| H4H9671P | 2.968E-09 | 8.622E-09 |
| H4H9675P | 1.754E-10 | 4.715E-10 |

TABLE 13

Anti-IL-33 antibodies blocking IL-33 induced IFN-γ release from human PBMC from donor #603491.

| Antibody | Donor #603491 $IC_{50}$ (M) |
|---|---|
| H1M9559N | Non-blocking |
| H1M9566N | Non-blocking |
| H1M9568N | Non-blocking |

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

Example 9

Human IL-33 Cross-competition Using Bio-layer Interferometry

Figure 1:
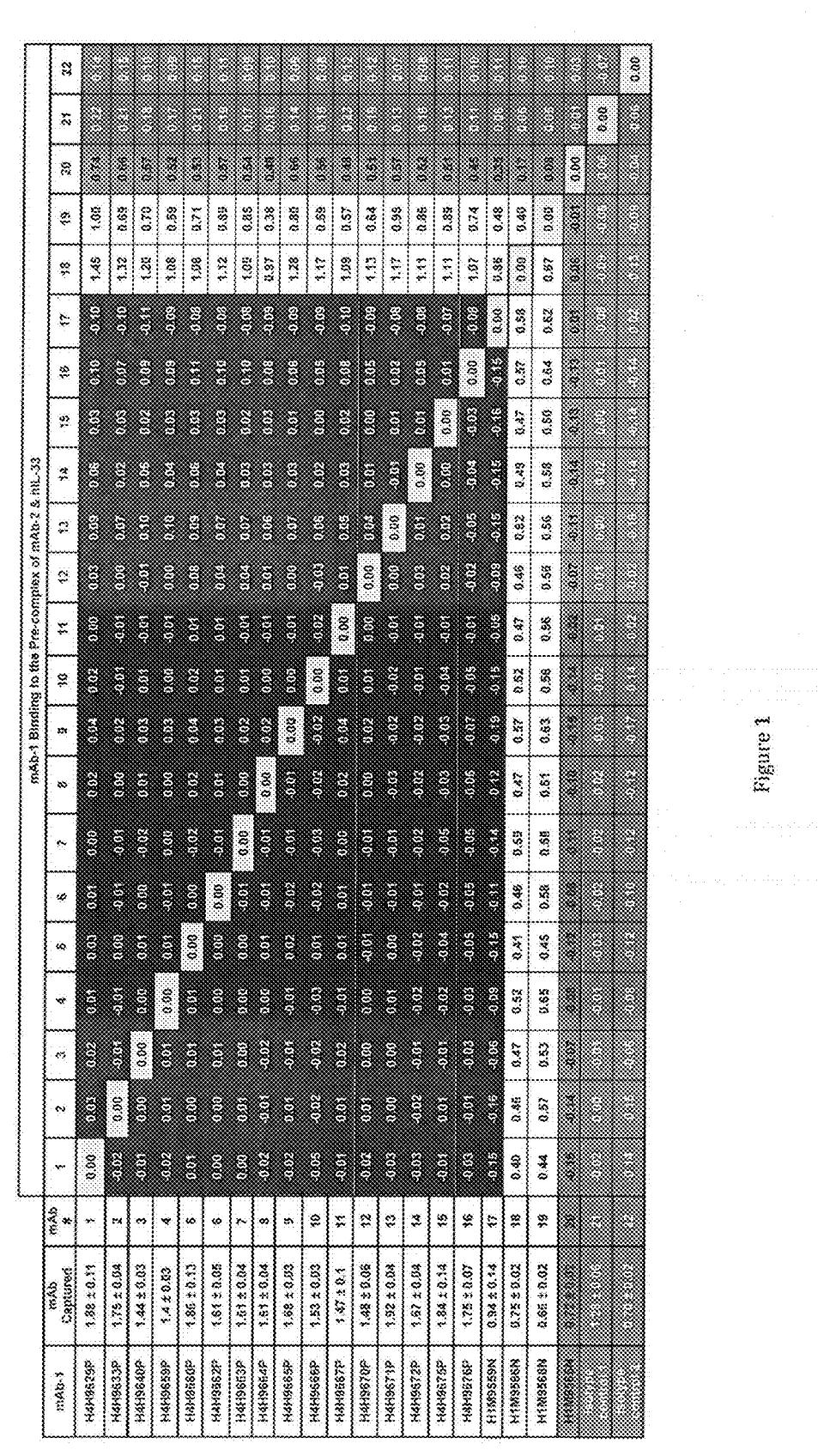

Binding competition between a panel of different anti-IL-33 monoclonal antibodies was determined using a real time, label-free bio-layer interferometry assay on an Octet® HTX biosensor (ForteBio, A Division of Pall Life Sciences). The experiment was performed at 25° C. using a buffer of 0.01M HEPES pH7.4, 0.15M NaCl, 0.05% v/v Surfactant Tween-20, and 0.1 mg/ml BSA (HBS-ET kinetics buffer) with the plate shaking at a speed of 1000 rpm. To assess whether two antibodies were able to compete with one another for binding to human IL-33, a pre-mix assay format was used where 100 nM of human IL-33 (R&D Systems; #3625-IL-010/CF) was pre-mixed with 500 nM of different anti-IL-33 monoclonal antibodies (subsequently referred to as mAb-2) for at least 2 hours prior to running the binding competition assay. Octet biosensors coated with either an anti-mouse Fc polyclonal antibody (Pall ForteBio Corp., #18-5088; subsequently referred as AMC) or with an anti-human Fc polyclonal antibody (Pall ForteBio Corp., #18-5060; subsequently referred as AHC) were first submerged into wells containing 20 μg/mL of individual anti-IL-33 monoclonal antibodies for 3 minutes to capture anti-IL-33 monoclonal antibodies expressed either a with mouse Fc or with a human Fc, respectively (subsequently referred to as mAb-1). Following the capture step, unoccupied anti-mouse Fc polyclonal antibody and anti-human Fc polyclonal antibody on the Octet biosensors were saturated by submerging them for 4 minutes into wells containing 200 pg/mL of a non-specific monoclonal antibody with a mouse Fc or with a human Fc, respectively. Finally, the Octet biosensors were immersed for 4 minutes into wells containing the pre-mixed samples of 100 nM of human IL-33 and 500 nM of mAb-2. At the end of each cycle, the non-covalently captured anti-IL-33 antibodies along with the bound pre-complex of human IL-33 and mAb-2 were removed from the biosensors using three alternate 20 second immersions into 10 mM HCl followed by submerging into HBS-ET kinetics buffer. The biosensors were washed in HBS-ET kinetics buffer in between every step of the experiment. The real-time binding response was monitored during the binding events, and the binding response (in units of nm) at the end of every step was recorded. During the analysis, the self-self background binding signal for a given mAb-2 (where mAb-1=mAb-2, i.e., along the diagonal of the matrix) was subtracted from the observed signal for all mAb-2 binding events (across a column in the cross-competition matrix), and the background-corrected results are shown in FIG. 1. The response of mAb-1 binding to the pre-complex of human IL-33 and each of the different mAb-2 samples was measured to determine the competitive/non-competitive behavior of different anti-IL-33 monoclonal antibodies with respect to each other.

As shown in FIG. 1 light grey boxes with black font represent binding response for self-competition. Antibodies competing with each other in both directions, independent of the order of binding, are represented with black boxes and white font. Cells highlighted in dark grey with black font represent the anti-IL-33 monoclonal antibody that binds weakly to human IL-33, resulting in an observed unidirectional cross-competition. The isotype controls used in the experiment are represented by dark grey boxes with white font. White boxes with black font represent no competition between antibodies, which suggests each antibody has a distinct binding epitope.

Example 10

Monkey IL-33 Cross-competition Using Bio-layer Interferometry

Binding competition between a panel of different anti-IL-33 monoclonal antibodies was determined using a real time, label-free bio-layer interferometry assay on an Octet® HTX biosensor (ForteBio, A Division of Pall Life Sciences). The experiment was performed at 25° C. using a buffer of 0.01M HEPES pH7.4, 0.15M NaCl, 3 mM EDTA, 0.05% v/v Surfactant Tween-20, and 0.1 mg/ml BSA (HBS-ET kinetics buffer) with the plate shaking at a speed of 1000 rpm. To assess whether two antibodies were able to compete with one another for binding to recombinant monkey IL-33 expressed with a C-terminal hexahistidine tag (MfIL-33-6His; SEQ ID: 305), approximately 0.15 nm binding units of MfIL-33-6His was first captured onto anti-penta-His antibody coated Octet biosensors (Fortebio Inc, #18-5079) by submerging the biosensors for 85 seconds into wells containing 2 μg/mL of MfIL-33-6His. The antigen-captured biosensors were then saturated with a first anti-IL-33 monoclonal antibody (subsequently referred to as mAb-1) by immersion into wells containing 50 μg/mL solution of mAb-1 for 5 minutes. The biosensors were then dipped into wells containing a 50 μg/mL solution of a second anti-IL-33 monoclonal antibody (subsequently referred to as mAb-2) for 4 minutes. The biosensors were washed in HBS-ET kinetics buffer in between every step of the experiment. The real-time binding response was monitored during the experiment, and the maximum binding response for each binding step was recorded. The response of mAb-2 binding to MfIL-33-6His pre-complexed with mAb-1 was measured, and competitive/non-competitive behavior of different anti-IL-33 monoclonal antibodies with respect to each other was determined.

Figure 2:
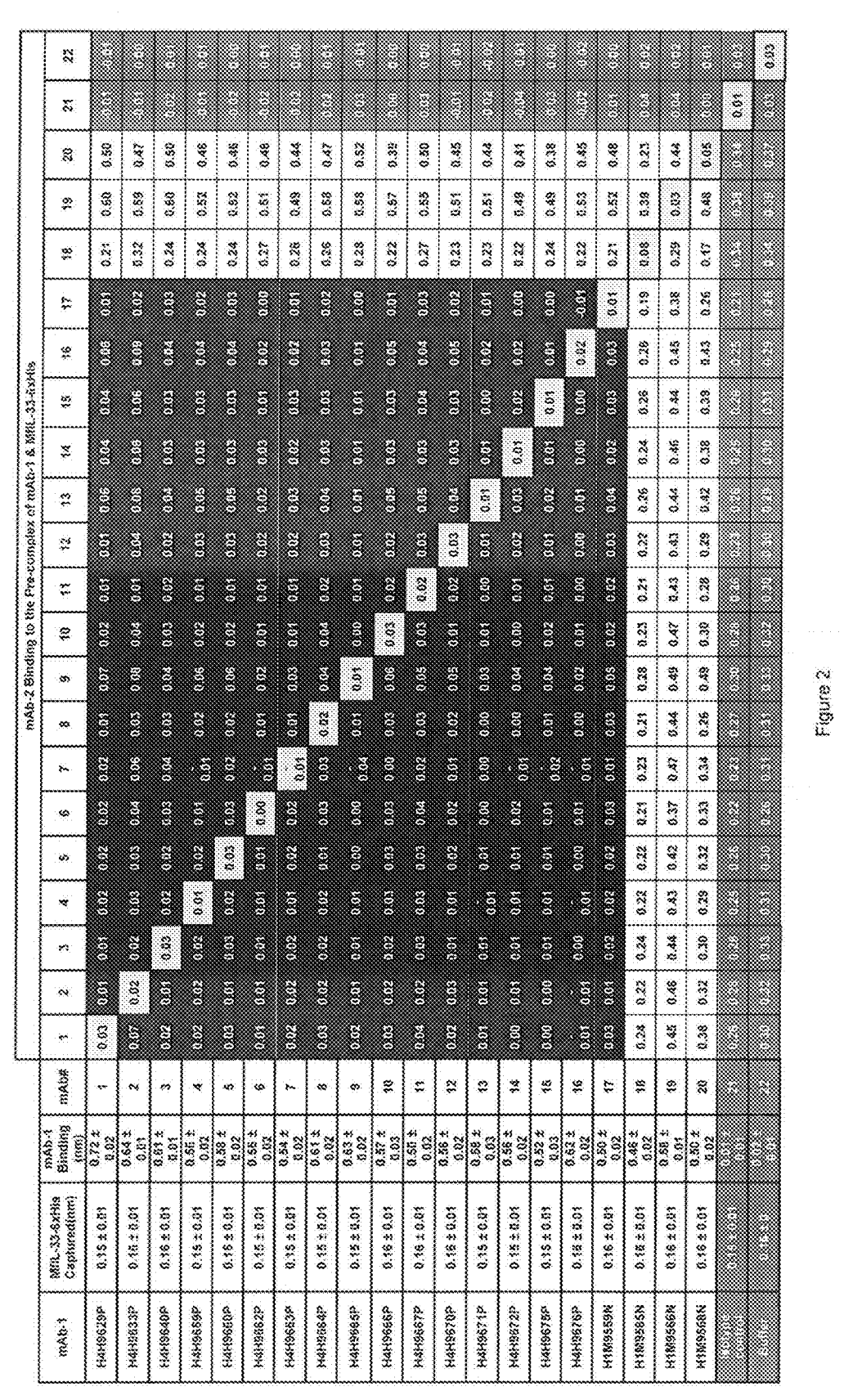

As shown in FIG. 2, light grey boxes with black font (along a diagonal) represent self-competition (where mAb-1=mAb-2). Antibodies competing in both directions, independent of the order of binding, are represented with black boxes and white font. White boxes with black font represent no competition between antibodies, which suggests each antibody has a distinct binding epitope. Dark grey boxes with white font represent the isotype control used in the experiment.

Example 11 mAb Testing in In Vivo Model; Acute HDM-inducted Lung Inflammation Model to Study Role of IL-33 in Lung Inflammation To determine the effect of an anti-IL-33 antibody, H4H9675P, in a relevant in vivo model, an acute HDM-induced lung inflammation study was conducted in mice that were homozygous for the expression of human IL-33 in place of mouse IL-33 (IL-33 Humin mice).

IL-33 Humin mice were intranasally administered either 50 μg of house dust mite extract (HDM; Greer, #XPB70D3A2.5) diluted in 20 μL of 1× phosphate buffered saline (PBS) (n=17) or 20 μL of 1×PBS (n=3) for 5 days per week for 2 weeks. A subset of the HDM challenged mice were injected subcutaneously with either 25 mg/kg of an anti-IL-33 antibody, H4H9675, (n=6) or an isotype control antibody (n=6) starting at three days prior to the first HDM administration and then twice weekly until the end of the HDM challenge. On day 15 after the first intranasal HDM, all mice were sacrificed and their lungs were harvested. Experimental dosing and treatment protocol for groups of mice are shown in Table 14.

TABLE 14

Experimental dosing and treatment protocol for groups of mice

| Group | Mice | Intranasal challenge | Length of intranasal challenge | Antibody |
|---|---|---|---|---|
| 1 | IL-33 HumIn mice | 1X PBS | 2 weeks | None |
| 2 | IL-33 HumIn mice | 50 μg HDM in 20 μL 1X PBS | 2 weeks | None |
| 3 | IL-33 HumIn mice | 50 μg HDM in 20 μL 1X PBS | 2 weeks | Isotype control |
| 4 | IL-33 HumIn mice | 50 μg HDM in 20 μL 1X PBS | 2 weeks | Anti-IL-33 antibody (H4H9675) |

Lung Harvest for Cytokine Analysis

After exsanguination, the cranial and middle lobes of the right lung from each mouse were removed and placed into tubes containing a solution of tissue protein extraction reagent (1×T-PER reagent; Pierce, #78510) supplemented with 1× Halt Protease inhibitor cocktail (Pierce, #78430). All further steps were performed on ice. The volume of T-PER Reagent (containing the protease inhibitor cocktail) was adjusted for each sample to match a 1:8 (w/v) tissue to T-PER ratio. Lung samples were manually homogenized in the tubes, using disposable pestles (Kimble Chase, #749625-0010). The resulting lysates were centrifuged to pellet debris. The supernatants containing the soluble protein extracts were transferred to fresh tubes and stored at 4° C. until further analysis.

Total protein content in the lung protein extracts was measured using a Bradford assay. For the assay, 10 μL of diluted extract samples were plated into 96 well plates in duplicates and mixed with 200 μL of 1× Dye Reagent (Biorad, #500-0006). Serial dilutions of bovine serum albumin (Sigma, #A7979), starting at 700 μg/mL in 1×T-Per reagent were used as a standard to determine the exact protein concentration of the extracts. After a 5-minute incubation at room temperature, absorbance at 595 nm was measured on a Molecular Devices SpectraMax M5 plate reader. Data analysis to determine total protein content was performed using GraphPad Prism™ software.

Cytokine concentrations in the lung protein extracts were measured using a Proinflammatory Panel 1 (mouse) multiplex immunoassay kit (MesoScale Discovery, #K15048D-2), according to the manufacturer's instructions. Briefly, 50 μL/well of calibrators and samples (diluted in Diluent 41) were added to plates pre-coated with capture antibodies and incubated at room temperature while shaking at 700 rpm for 2 hours. The plates were then washed 3 times with 1×PBS containing 0.05% (w/v) Tween-20, followed by the addition of 25 μL of Detection Antibody Solution diluted in Diluent 45. After another 2-hour incubation at room temperature while shaking, the plate was washed 3 times, and 150 μL of 2× Read Buffer was added to each well. Electrochemiluminescence was immediately read on a MSD Spector® instrument. Data analysis was performed using GraphPad Prism™ software.

Each cytokine concentration in lung total protein extracts from all mice in each group was normalized to the total protein content of the extracts measured by the Bradford assay and expressed for each group as average pg of cytokine per mg of total lung proteins (pg/mg lung protein, ±SD) as shown in Table 15.

Lung Harvest for Cytokine Analysis

The level of the cytokines IL-4 and IL-5 released in the lungs of IL-33 Humin mice receiving HDM for 2 weeks was significantly higher than in IL-33 Humin mice challenged with saline buffer. In contrast, there was a trend towards reduced IL-4 and IL-5 levels in the lungs of IL-33 Humin mice treated with anti-IL-33 antibody during the course of the acute HDM challenge as compared to IL-33 Humin mice administered HDM without treatment or with isotype control.

TABLE 15

Cytokine concentration in lung protein extracts

| Experimental group | Mean [IL-4] in lung protein extracts (pg/mg lung protein) (±SD) | Mean [IL-5] in lung protein extracts (pg/mg lung protein) (±SD) |
|---|---|---|
| 1. 1X PBS challenge (n = 3) | 0.01 (±0.01) | 0.03 (±0.01) |
| 2. HDM challenge (n = 5) | 1.77 (±1.63) * | 4.72 (±4.14) ** |
| 3. HDM challenge + Isotype control Antibody (n = 6) | 0.79 (±0.52) * | 2.03 (±1.05) * |
| 4. HDM challenge + H4H9675P (n = 6) | 0.30 (±0.18) | 0.81 (±0.67) |

Note:
Statistical significance determined by Kruskal-Wallis One-way ANOVA with Dunn's multiple comparison post-hoc test is indicated (* = p < 0.05, ** = p < 0.01, compared to Group 1: IL33 HumIn mice, Saline challenge).

Lung Harvest for Pulmonary Cell Infiltrate Analysis

After exsanguination, the caudal lobe of the right lung from each mouse was removed, chopped into cubes that were approximately 2 to 3 mm in size, and then placed into a tube containing a solution of 20 μg/mL DNAse (Roche, #10104159001) and 0.7 U/mL Liberase TH (Roche, #05401151001) diluted in Hank's Balanced Salt Solution (HBSS) (Gibco, #14025), which was incubated in a 37° C. water bath for 20 minutes and vortexed every 5 minutes. The reaction was stopped by adding ethylenediaminetetraacetic acid (Gibco, #15575) at a final concentration of 10 mM. Each lung was subsequently dissociated using a gentleMACS dissociator® (Miltenyi Biotec, #130-095-937), then filtered through a 70 μm filter and centrifuged. The resulting lung pellet was resuspended in 1 mL of 1× red blood cell lysing buffer (Sigma, #R7757) to remove red blood cells. After incubation for 3 minutes at room temperature, 3 mL of 1×DMEM was added to deactivate the red blood cell lysing buffer. The cell suspensions were then centrifuged, and the resulting cell pellets were resuspended in 5 mL of MACS buffer (autoMACS Running Buffer; Miltenyi Biotec, #130-091-221). The resuspended samples were filtered through a 70 μm filter and 1×10$^6$ cells per well were plated in a 96-well V-bottom plate. Cells were then centrifuged and the pellets were washed in 1×PBS. After a second centrifugation, the cell pellets were resuspended in 100 μL of LIVE/DEAD® Fixable Aqua Dead Cell Stain (Life Technologies, #L34957) diluted at 1:1000 in 1×PBS to determine cell viability and incubated for 20 minutes at room temperature while protected from light. After one wash in 1×PBS, cells were incubated in a solution of MACS buffer containing 10 μg/mL of purified rat anti-mouse CD16/CD32 Fc Block, (Clone: 2.4G2; BD Biosciences, #553142) for 10 minutes at 4° C. The cells were washed once and then incubated in the appropriate antibody mixture (described in Table 16) diluted in MACS buffer for 30 minutes at 4° C. while protected from light. After antibody incubation, the cells were washed twice in MACS buffer, resuspended in BD cytofix (BD Biosciences, #554655) and then incubated for 15 minutes at 4° C. while protected from light. The cells were subsequently washed, resuspended in MACS buffer, and then transferred to BD FACS tubes (BD Biosciences, #352235) for analysis of eosinophils, innate lymphoid cell type 2 (ILC2) and lymphocytes by flow cytometry.

Activated CD4 T cells were defined as cells that were live, CD45$^+$, SSC$^{Lo}$, FSC$^{Lo}$, CD3$^+$, CD19$^-$, CD4$^+$, CD8$^-$, and CD69$^+$. Activated B cells were defined as cells that were live, CD45$^+$, SSC$^{Lo}$, FSC$^{Lo}$, CD3$^-$, CD69$^+$. Eosinophils were defined as live, CD45$^+$, GR1$^-$, CD11c$^{lo}$, SiglecF$^{hi}$. ILC2 cells were defined as live, CD45$^+$, Lineage- (Lineage: CD19, CD3, CD11b, CD11c, F4/80), CD127+, Sca$^-$1$^+$, ST2$^+$. Data for activated CD4 cells, expressed as frequency of activated cells (CD69$^+$) within the parent population (CD4, ±SD), are shown in Table 17.

TABLE 16

Antibodies Used for Flow Cytometry Analysis

| Antibody | Fluorochrome | Manufacturer | Catalog Number | Final dilution |
|---|---|---|---|---|
| CD11c | APC | BD Biosciences | 550261 | 1/100 |
| CD45 | PerCP Cy5.5 | eBiosciences | 45-0454-82 | 1/800 |
| F4/80 | Pacific Blue | eBiosciences | 48-4801-82 | 1/200 |
| Siglec-F | PE | BD Biosciences | 552126 | 1/100 |
| Ly6G (Gr-1) | APC-eFluor780 | eBiosciences | 47-5931-82 | 1/200 |
| CD3 | PE-Cy7 | BD Biosciences | 552774 | 1/200 |
| CD19 | eFluor 450 | eBiosciences | 48-0193-82 | 1/200 |
| CD4 | APC-H7 | BD Biosciences | 560181 | 1/200 |
| CD8 | APC | eBiosciences | 17-0081-82 | 1/200 |
| CD69 | PE | eBiosciences | 12-0691-82 | 1/200 |
| CD3 | eFluor 450 | eBiosciences | 48-0031-82 | 1/200 |
| CD11b | eFluor450 | eBiosciences | 40-0112-82 | 1/200 |
| CD11c | eFluor450 | eBiosciences | 48-0114-82 | 1/100 |
| CD127 | APC-eFluor780 | eBiosciences | 47-1271-82 | 1/200 |
| Sca-1 | FITC | BD Biosciences | 557405 | 1/200 |
| ST2 | APC | Biolegend | 145306 | 1/200 |

Pulmonary Cell Infiltrate Analysis

As shown in Table 17, the frequency of activated CD4$^+$ cells, eosinophils, and ILC2 in the lungs of IL-33 Humin mice receiving HDM for 2 weeks was significantly higher than in IL-33 Humin mice challenged with 1×PBS control. In contrast, a trend towards a reduced frequency of these infiltrates was observed in IL-33 Humin mice when treated with the anti-IL-33 antibody during the course of the acute HDM challenge as compared to IL-33 Humln mice administered HDM without treatment or with isotype control.

A trend towards an increase in the frequency of activated B cells was observed in the lungs of IL33 Humln mice challenged with HDM for 2 weeks compared to IL33 Humin mice challenged with 1×PBS control. Upon anti-IL-33 antibody treatment, a significant reduction in the frequency of pulmonary activated B cells in the lungs of IL33 Humln mice challenged with HDM was observed, as compared to IL-33 Humin mice administered HDM without treatment or with isotype control.

TABLE 17

Frequency of pulmonary cell infiltrate as determined by flow cytometry

| Experimental group | Mean Frequency of activated CD4+ T cells in CD4+ population (±SD) | Mean Frequency of activated B cells in the B cell population (±SD) | Mean Frequency of eosinophils in CD45+ population (±SD) | Mean Frequency of ILC2 in Lymphoid population (±SD) |
|---|---|---|---|---|
| 1. 1X PBS challenge (n = 3) | 6.17 (±0.59) | 6.85 (±3.09) | 2.55 (±0.79) | 0.33 (±0.05) |
| 2. HDM challenge (n = 5) | 29.52 (±8.57) * | 10.13 (±3.30) | 17.28 (±3.97) * | 1.15 (±0.37) * |
| 3. HDM challenge + Isotype control Antibody (n = 6) | 29.68 (±9.84) * | 11.01 (±2.31) | 19.19 (±11.55) * | 1.57 (±0.78) * |
| 4. HDM challenge + H4H9675P (n = 6) | 16.38 (±3.30) | 4.88 (±1.70) † | 10.32 (±4.63) | 0.53 (±0.12) |

Note:
Statistical significance determined by Kruskal-Wallis One-way ANOVA with Dunn's multiple comparison post-hoc test is indicated (* = p < 0.05, ** = p < 0.01, compared to groups 1: IL33 HumIn mice, Saline challenge; † p < 0.05, compared to group 3: IL33 Humin mice, HDM challenge 2 weeks + Isotype control antibody).

Example 12 mAb Testing in In Vivo Model; Chronic HDM-induced Fibrosis and Severe Lung Inflammation Model to Study Role of IL-33 in Lung Inflammation To determine the effect of an anti-IL-33 antibody, H4H9675P, in a relevant in vivo model, a chronic HDM-induced fibrosis and severe lung inflammation study was conducted in mice that were homozygous for the expression of human IL-33 in place of mouse IL-33 (IL-33 HumIn mice).

IL-33 HumIn mice were intranasally administered either 50 µg house dust mite extract (HDM; Greer, #XPB70D3A2.5) diluted in 20 µL of 1× phosphate buffered saline (PBS) or 20 µL of 1×PBS for 5 days per week for 12 weeks. A second control group of IL33 HumIn mice were administered 50 µg HDM extract diluted in 20 µL of 1×PBS for 5 days per week for 4 weeks, to assess the severity of the disease at the onset of antibody treatment. Two groups of HDM challenged mice were injected subcutaneously with 25 mg/kg of either an anti-IL-33 antibody, H4H9675P, or an isotype control antibody starting after 4 weeks of HDM challenge and then twice per week until the end of the HDM challenge (8 weeks of antibody treatment). On day 85 of the study, all mice were sacrificed and their lungs were harvested. Experimental dosing and treatment protocol for groups of mice are shown in Table 18.

TABLE 18

Experimental dosing and treatment protocol for groups of mice

| Group | Mice | Intranasal challenge | Length of intranasal challenge | Antibody |
|---|---|---|---|---|
| 1 | IL-33 HumIn mice | 1X PBS | 12 weeks | None |
| 2 | IL-33 HumIn mice | 50 µg HDM in 20 µL 1X PBS | 4 weeks | None |
| 3 | IL-33 HumIn mice | 50 µg HDM in 20 µL 1X PBS | 12 weeks | None |
| 4 | IL-33 HumIn mice | 50 µg HDM in 20 µL 1X PBS | 12 weeks | Isotype control antibody |
| 5 | IL-33 HumIn mice | 50 µg HDM in 20 µL 1X PBS | 12 weeks | Anti-IL-33 antibody (H4H9675P) |

Lung Harvest for Cytokine Analysis

After exsanguination, the cranial and middle lobes of the right lung from each mouse were removed and placed into tubes containing a solution of tissue protein extraction reagent (1×T-PER reagent; Pierce, #78510) supplemented with 1× Halt Protease inhibitor cocktail (Pierce, #78430). All further steps were performed on ice. The volume of T-PER Reagent (containing the protease inhibitor cocktail) was adjusted for each sample to match a 1:8 (w/v) tissue to T-PER ratio. Lung samples were manually homogenized in the tubes, using disposable pestles (Kimble Chase, #749625-0010). The resulting lysates were centrifuged to pellet debris. The supernatants containing the soluble protein extracts were transferred to fresh tubes and stored at 4° C. until further analysis.

Total protein content in the lung protein extracts was measured using a Bradford assay. For the assay, 10 µL of diluted extract samples were plated into 96 well plates in duplicates and mixed with 200 µL of 1× Dye Reagent (Biorad, #500-0006). Serial dilutions of bovine serum albumin (BSA; Sigma, #A7979), starting at 700 µg/mL in 1×T-Per reagent were used as a standard to determine the protein concentration of the extracts. After a 5-minute incubation at room temperature, absorbance at 595 nm was measured on a Molecular Devices SpectraMax M5 plate reader. Data analysis to determine total lung extract protein content based on the BSA standard was performed using GraphPad Prism™ software.

Cytokine concentrations in the lung protein extracts were measured using a Proinflammatory Panel 1 (mouse) multiplex immunoassay kit (MesoScale Discovery, # K15048D-2), according to the manufacturer's instructions. Briefly, 50 µL/well of calibrators and samples (diluted in Diluent 41) were added to plates pre-coated with capture antibodies and incubated at room temperature while shaking at 700 rpm for 2 hours. The plates were then washed 3 times with 1×PBS containing 0.05% (w/v) Tween-20, followed by the addition of 25 µL of Detection Antibody Solution diluted in Diluent 45. After another 2 hour incubation at room temperature while shaking, the plate was washed 3 times, and 150 µL of 2× Read Buffer was added to each well. Electrochemiluminescence was immediately read on a MSD Spector® instrument. Data analysis was performed using GraphPad Prism software.

Each cytokine concentration in lung total protein extracts from all mice in each group was normalized to the total protein content of the extracts measured by the Bradford assay, and expressed for each group as average pg of cytokine per mg of total lung proteins (pg/mg lung protein, ±SD) as shown in Table 19.

TABLE 19

Cytokine concentration in lung protein extracts

| Experimental group | Mean [IL-4] in lung protein extracts (pg/mg lung protein) (±SD) | Mean [IL-5] in lung protein extracts (pg/mg lung protein) (±SD) |
|---|---|---|
| 1. 1X PBS challenge, 12 weeks (n = 5) | 0.03 (±0.01) | 0.08 (±0.05) |
| 2. HDM challenge, 4 weeks (n = 6) | 2.84 (±2.22) * | 4.44 (±4.00) ** |
| 3. HDM challenge, 12 weeks (n = 3) | 7.31 (±3.94) ** | 6.23 (±3.81) * |
| 4. HDM challenge, 12 weeks + Isotype control antibody (n = 2) | 2.28 (±1.94) | 3.39 (±3.29) |
| 5. HDM challenge, 12 weeks + H4H9675P (n = 5) | 0.38 (±0.21) | 0.48 (±0.17) |

Note:
Statistical significance determined by Kruskal-Wallis One-way ANOVA with Dunn's multiple comparison post-hoc test is indicated (* = p < 0.05, ** = p < 0.01, compared to groups 1: IL33 HumIn mice, Saline challenge).

Lung Cytokines Analysis

The level of the cytokines IL-4 and IL-5 released in the lungs of IL-33 HumIn mice receiving HDM for 4 and 12 weeks was significantly higher than in IL-33 HumIn mice challenged with 1×PBS. In contrast, there was a trend towards reduced IL-4 and IL-5 levels in the lungs of IL-33 HumIn mice treated with anti-IL-33 antibody during the course of the chronic HDM challenge as compared to IL-33 HumIn mice administered HDM without treatment or with isotype control.

What is claimed is:

1. An isolated nucleic acid molecule encoding an antibody or antigen-binding fragment thereof that specifically binds human interleukin-33 (IL-33), wherein the antibody or antigen-binding fragment comprises the complementarity determining regions (CDRs) of a heavy chain variable region (HCVR) comprising the amino acid sequence selected from the group consisting of SEQ ID NOs: 50, 82, 98, 130, 178, and 274, and the CDRs of a light chain variable region (LCVR) comprising the amino acid sequence selected from the group consisting of SEQ ID NOs: 58, 90, 106, 138, 186, and 282.

2. An isolated expression vector comprising the nucleic acid molecule of claim 1.

3. An isolated host cell comprising the expression vector of claim 2.

4. The isolated nucleic acid molecule of claim 1, wherein the antibody or antigen-binding fragment comprises the heavy and light chain CDRs of a HCVR/LCVR amino acid sequence pair selected from the group consisting of: SEQ ID NOs: 50/58, 82/90, 98/106, 130/138, 178/186, and 274/282.

5. The isolated nucleic acid molecule of claim 1, wherein the antibody or antigen-binding fragment comprises HCDR1-HCDR2-HCDR3-LCDR1-LCDR2-LCDR3 domains, respectively, selected from the group consisting of: SEQ ID NOs: 52-54-56-60-62-64; 84-86-88-92-94-96; 100-102-104-108-110-112; 132-134-136-140-142-144; 180-182-184-188-190-192; and 276-278-280-284-286-288.

6. The isolated nucleic acid molecule of claim 1, wherein the antibody or antigen-binding fragment comprises: (a) a heavy chain variable region (HCVR) comprising the amino acid sequence selected from the group consisting of SEQ ID NOs: 50, 82, 98, 130, 178, and 274; and (b) a light chain variable region (LCVR) comprising the amino acid sequence selected from the group consisting of SEQ ID NOs: 58, 90, 106, 138, 186, and 282.

7. The isolated nucleic acid molecule of claim 6, wherein the antibody or antigen-binding fragment comprises a HCVR/LCVR amino acid sequence pair selected from the group consisting of: SEQ ID NOs: 50/58, 82/90, 98/106, 130/138, 178/186, and 274/282.

8. The isolated nucleic acid molecule of claim 7, wherein the antibody or antigen-binding fragment comprises a HCVR/LCVR amino acid sequence pair of SEQ ID NOs: 50/58.

9. The isolated nucleic acid molecule of claim 7, wherein the antibody or antigen-binding fragment comprises a HCVR/LCVR amino acid sequence pair of SEQ ID NOs: 82/90.

10. The isolated nucleic acid molecule of claim 7, wherein the antibody or antigen-binding fragment comprises a HCVR/LCVR amino acid sequence pair of SEQ ID NOs: 98/106.

11. The isolated nucleic acid molecule of claim 7, wherein the antibody or antigen-binding fragment comprises a HCVR/LCVR amino acid sequence pair of SEQ ID NOs: 130/138.

12. The isolated nucleic acid molecule of claim 7, wherein the antibody or antigen-binding fragment comprises a HCVR/LCVR amino acid sequence pair of SEQ ID NOs: 178/186.

13. The isolated nucleic acid molecule of claim 7, wherein the antibody or antigen-binding fragment comprises a HCVR/LCVR amino acid sequence pair of SEQ ID NOs: 274/282.

14. An isolated nucleic acid molecule encoding an antibody or antigen-binding fragment thereof that specifically binds human interleukin-33 (IL-33), wherein the antibody or antigen-binding fragment comprises a heavy chain variable region (HCVR) comprising the amino acid sequence selected from the group consisting of SEQ ID NOs: 50, 82, 98, 130, 178, and 274.

15. An isolated expression vector comprising the nucleic acid molecule of claim 5.

16. An isolated host cell comprising the expression vector of claim 15.

17. An isolated expression vector comprising the nucleic acid molecule of claim 7.

18. An isolated host cell comprising the expression vector of claim 17.

19. An isolated expression vector comprising the nucleic acid molecule of claim 13.

20. An isolated host cell comprising the expression vector of claim 19.

* * * * *

SEQUENCE LISTING

<160> NUMBER OF SEQ ID NOS: 323

<210> SEQ ID NO 1
<211> LENGTH: 366
<212> TYPE: DNA
<213> ORGANISM: Artificial Sequence
<220> FEATURE:
<223> OTHER INFORMATION: Synthetic

<400> SEQUENCE: 1

```
caggtgcagc tggtggagtc tgggggaggc gtggtccagc ctgggaggtc cctgagactc      60
tcctgtgcag cgtctggatt caccttcagt agttatggca tgcattgggt ccgccaggct     120
ccaggcaagg ggctggagtg ggtggcagtt atatggtatg atggaagaaa taaatactat     180
acagactccg tgaagggccg attcaccatc tccagagaca attccaagaa cacgctgtat     240
ctgcaaatgg acagcctgag agccgaggac acggctgtgt attactgtgc gagagagagg     300
tatatcagca gctattatgg ggggttcgac ccctggggcc agggagccct ggtcaccgtc     360
tcctca                                                                 366
```

<210> SEQ ID NO 2
<211> LENGTH: 122
<212> TYPE: PRT
<213> ORGANISM: Artificial Sequence
<220> FEATURE:
<223> OTHER INFORMATION: Synthetic

<400> SEQUENCE: 2

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Arg Asn Lys Tyr Tyr Thr Asp Ser Val
    50                  55                  60

Lys Gly Arg Phe Thr Ile Ser Arg Asp Asn Ser Lys Asn Thr Leu Tyr
65                  70                  75                  80

Leu Gln Met Asp Ser Leu Arg Ala Glu Asp Thr Ala Val Tyr Tyr Cys
                85                  90                  95

Ala Arg Glu Arg Tyr Ile Ser Ser Tyr Tyr Gly Gly Phe Asp Pro Trp
            100                 105                 110

Gly Gln Gly Ala Leu Val Thr Val Ser Ser
        115                 120
```

<210> SEQ ID NO 3
<211> LENGTH: 24
<212> TYPE: DNA
<213> ORGANISM: Artificial Sequence
<220> FEATURE:
<223> OTHER INFORMATION: Synthetic

<400> SEQUENCE: 3

```
ggattcacct tcagtagtta tggc                                              24
```

<210> SEQ ID NO 4
<211> LENGTH: 8
<212> TYPE: PRT
<213> ORGANISM: Artificial Sequence
<220> FEATURE:
<223> OTHER INFORMATION: Synthetic

<400> SEQUENCE: 4

Gly Phe Thr Phe Ser Ser Tyr Gly
1               5

<210> SEQ ID NO 5
<211> LENGTH: 24
<212> TYPE: DNA
<213> ORGANISM: Artificial Sequence
<220> FEATURE:
<223> OTHER INFORMATION: Synthetic

<400> SEQUENCE: 5
atatggtatg atggaagaaa taaa                                          24

<210> SEQ ID NO 6
<211> LENGTH: 8
<212> TYPE: PRT
<213> ORGANISM: Artificial Sequence
<220> FEATURE:
<223> OTHER INFORMATION: Synthetic

<400> SEQUENCE: 6

Ile Trp Tyr Asp Gly Arg Asn Lys
1               5

<210> SEQ ID NO 7
<211> LENGTH: 45
<212> TYPE: DNA
<213> ORGANISM: Artificial Sequence
<220> FEATURE:
<223> OTHER INFORMATION: Synthetic

<400> SEQUENCE: 7
gcgagagaga ggtatatcag cagctattat gggggttcg acccc                    45

<210> SEQ ID NO 8
<211> LENGTH: 15
<212> TYPE: PRT
<213> ORGANISM: Artificial Sequence
<220> FEATURE:
<223> OTHER INFORMATION: Synthetic

<400> SEQUENCE: 8

Ala Arg Glu Arg Tyr Ile Ser Ser Tyr Tyr Gly Gly Phe Asp Pro
1               5                   10                  15

<210> SEQ ID NO 9
<211> LENGTH: 321
<212> TYPE: DNA
<213> ORGANISM: Artificial Sequence
<220> FEATURE:
<223> OTHER INFORMATION: Synthetic

<400> SEQUENCE: 9
gacatccaga tgacccagtc tccatcctcc gtgtctgcat ctgtaggaga cagagtcacc    60
atcacttgtc gggcgagtca gggtattagt agttggttag cctggtatca gcagaaacca   120
gggaaagccc ctaaggtcct gatctatgct gcatccagtt tgcaaagtgg ggtcccatca   180
aggttcagcg gcagtggatc tgggacagat ttcactctca ccatcagcag cctgcagcct   240
gaagattttg caacttacta ttgtcaacag gctaacagtt tcccattcac tttcggccct   300
gggaccaaac tggatatcaa g                                              321

<210> SEQ ID NO 10
<211> LENGTH: 107
<212> TYPE: PRT
<213> ORGANISM: Artificial Sequence
<220> FEATURE:
<223> OTHER INFORMATION: Synthetic

<400> SEQUENCE: 10

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Val Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Phe
                85                  90                  95

Thr Phe Gly Pro Gly Thr Lys Leu Asp Ile Lys
            100                 105
```

<210> SEQ ID NO 11
<211> LENGTH: 18
<212> TYPE: DNA
<213> ORGANISM: Artificial Sequence
<220> FEATURE:
<223> OTHER INFORMATION: Synthetic

<400> SEQUENCE: 11
cagggtatta gtagttgg                                                        18

<210> SEQ ID NO 12
<211> LENGTH: 6
<212> TYPE: PRT
<213> ORGANISM: Artificial Sequence
<220> FEATURE:
<223> OTHER INFORMATION: Synthetic

<400> SEQUENCE: 12

```
Gln Gly Ile Ser Ser Trp
1               5
```

<210> SEQ ID NO 13
<211> LENGTH: 9
<212> TYPE: DNA
<213> ORGANISM: Artificial Sequence
<220> FEATURE:
<223> OTHER INFORMATION: Synthetic

<400> SEQUENCE: 13 gctgcatcc                                                                   9

<210> SEQ ID NO 14
<211> LENGTH: 3
<212> TYPE: PRT
<213> ORGANISM: Artificial Sequence
<220> FEATURE:
<223> OTHER INFORMATION: Synthetic

<400> SEQUENCE: 14

```
Ala Ala Ser
1
```

<210> SEQ ID NO 15
<211> LENGTH: 27
<212> TYPE: DNA
<213> ORGANISM: Artificial Sequence
<220> FEATURE:
<223> OTHER INFORMATION: Synthetic

<400> SEQUENCE: 15
caacaggcta acagtttccc attcact                                          27

<210> SEQ ID NO 16
<211> LENGTH: 9
<212> TYPE: PRT
<213> ORGANISM: Artificial Sequence
<220> FEATURE:
<223> OTHER INFORMATION: Synthetic

<400> SEQUENCE: 16

Gln Gln Ala Asn Ser Phe Pro Phe Thr
1               5

<210> SEQ ID NO 17
<211> LENGTH: 357
<212> TYPE: DNA
<213> ORGANISM: Artificial Sequence
<220> FEATURE:
<223> OTHER INFORMATION: Synthetic

<400> SEQUENCE: 17
gaggtgcagc tgttggagtc tgggggagac ttggtacagc ctggggggtc cctgagactc      60
tcctgtgcag cctctggatt caccttcagc agctatgcca tgagctgggt ccgccaggct     120
ccagggaagg gctggagtg gtctcagtt attagtggta gtggaagtag cacagactac       180
gcagactccg tgaagggccg gttcaccatt tccagagaca attccaggga cacgctgcat     240
ctgcaaatga acagcctgag agccgaggac acggccgtat attactgtgc gaaaacgttc     300
tactacttct acggtttgga cgtctggggc caagggacca cggtcaccgt ctcctca       357

<210> SEQ ID NO 18
<211> LENGTH: 119
<212> TYPE: PRT
<213> ORGANISM: Artificial Sequence
<220> FEATURE:
<223> OTHER INFORMATION: Synthetic

<400> SEQUENCE: 18

Glu Val Gln Leu Leu Glu Ser Gly Gly Asp Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Val Ile Ser Gly Ser Gly Ser Ser Thr Asp Tyr Ala Asp Ser Val
    50                  55                  60

Lys Gly Arg Phe Thr Ile Ser Arg Asp Asn Ser Arg Asp Thr Leu His
65                  70                  75                  80

Leu Gln Met Asn Ser Leu Arg Ala Glu Asp Thr Ala Val Tyr Tyr Cys
                85                  90                  95

Ala Lys Thr Phe Tyr Tyr Phe Tyr Gly Leu Asp Val Trp Gly Gln Gly
            100                 105                 110

Thr Thr Val Thr Val Ser Ser
        115

<210> SEQ ID NO 19
<211> LENGTH: 24
<212> TYPE: DNA
<213> ORGANISM: Artificial Sequence
<220> FEATURE:
<223> OTHER INFORMATION: Synthetic

<400> SEQUENCE: 19
ggattcacct tcagcagcta tgcc                                          24

<210> SEQ ID NO 20
<211> LENGTH: 8
<212> TYPE: PRT
<213> ORGANISM: Artificial Sequence
<220> FEATURE:
<223> OTHER INFORMATION: Synthetic

<400> SEQUENCE: 20

Gly Phe Thr Phe Ser Ser Tyr Ala
1               5

<210> SEQ ID NO 21
<211> LENGTH: 24
<212> TYPE: DNA
<213> ORGANISM: Artificial Sequence
<220> FEATURE:
<223> OTHER INFORMATION: Synthetic

<400> SEQUENCE: 21
attagtggta gtggaagtag caca                                          24

<210> SEQ ID NO 22
<211> LENGTH: 8
<212> TYPE: PRT
<213> ORGANISM: Artificial Sequence
<220> FEATURE:
<223> OTHER INFORMATION: Synthetic

<400> SEQUENCE: 22

Ile Ser Gly Ser Gly Ser Ser Thr
1               5

<210> SEQ ID NO 23
<211> LENGTH: 36
<212> TYPE: DNA
<213> ORGANISM: Artificial Sequence
<220> FEATURE:
<223> OTHER INFORMATION: Synthetic

<400> SEQUENCE: 23
gcgaaaacgt tctactactt ctacggtttg gacgtc                             36

<210> SEQ ID NO 24
<211> LENGTH: 12
<212> TYPE: PRT
<213> ORGANISM: Artificial Sequence
<220> FEATURE:
<223> OTHER INFORMATION: Synthetic

<400> SEQUENCE: 24

Ala Lys Thr Phe Tyr Tyr Phe Tyr Gly Leu Asp Val
1               5                   10

<210> SEQ ID NO 25
<211> LENGTH: 321
<212> TYPE: DNA
<213> ORGANISM: Artificial Sequence
<220> FEATURE:
<223> OTHER INFORMATION: Synthetic

<400> SEQUENCE: 25

```
gacatccaga tgacccagtc tccatcctcc ctgtctgcat ctttaagaga cagagtcacc      60
atcacttgcc gggcgagtca gggcattagc aattatttag cctggtatca gcagaaacca     120
gggaaagttc ctaaggtcct aatctatgct gcatccactt tgcaatcagg ggtcccatct     180
cggttcagtg gcagtggatc tgggacagtt ttcactctca ccatcagcag cctgcagact     240
gaagatgttg caacttatta ctgtcaaaag tatagcagtg ccccattcac tttcggccct     300
gggaccaaag tggatatcaa a                                               321
```

<210> SEQ ID NO 26
<211> LENGTH: 107
<212> TYPE: PRT
<213> ORGANISM: Artificial Sequence
<220> FEATURE:
<223> OTHER INFORMATION: Synthetic

<400> SEQUENCE: 26

```
Asp Ile Gln Met Thr Gln Ser Pro Ser Ser Leu Ser Ala Ser Leu Arg
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Val Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Val Phe Thr Leu Thr Ile Ser Ser Leu Gln Thr
65                  70                  75                  80

Glu Asp Val Ala Thr Tyr Tyr Cys Gln Lys Tyr Ser Ser Ala Pro Phe
                85                  90                  95

Thr Phe Gly Pro Gly Thr Lys Val Asp Ile Lys
            100                 105
```

<210> SEQ ID NO 27
<211> LENGTH: 18
<212> TYPE: DNA
<213> ORGANISM: Artificial Sequence
<220> FEATURE:
<223> OTHER INFORMATION: Synthetic

<400> SEQUENCE: 27

```
cagggcatta gcaattat                                                    18
```

<210> SEQ ID NO 28
<211> LENGTH: 6
<212> TYPE: PRT
<213> ORGANISM: Artificial Sequence
<220> FEATURE:
<223> OTHER INFORMATION: Synthetic

<400> SEQUENCE: 28

```
Gln Gly Ile Ser Asn Tyr
1               5
```

<210> SEQ ID NO 29

```
<211> LENGTH: 9
<212> TYPE: DNA
<213> ORGANISM: Artificial Sequence
<220> FEATURE:
<223> OTHER INFORMATION: Synthetic

<400> SEQUENCE: 29 gctgcatcc                                                                    9

<210> SEQ ID NO 30
<211> LENGTH: 3
<212> TYPE: PRT
<213> ORGANISM: Artificial Sequence
<220> FEATURE:
<223> OTHER INFORMATION: Synthetic

<400> SEQUENCE: 30

Ala Ala Ser
1

<210> SEQ ID NO 31
<211> LENGTH: 27
<212> TYPE: DNA
<213> ORGANISM: Artificial Sequence
<220> FEATURE:
<223> OTHER INFORMATION: Synthetic

<400> SEQUENCE: 31
caaaagtata gcagtgcccc attcact                                               27

<210> SEQ ID NO 32
<211> LENGTH: 9
<212> TYPE: PRT
<213> ORGANISM: Artificial Sequence
<220> FEATURE:
<223> OTHER INFORMATION: Synthetic

<400> SEQUENCE: 32

Gln Lys Tyr Ser Ser Ala Pro Phe Thr
1               5

<210> SEQ ID NO 33
<211> LENGTH: 351
<212> TYPE: DNA
<213> ORGANISM: Artificial Sequence
<220> FEATURE:
<223> OTHER INFORMATION: Synthetic

<400> SEQUENCE: 33
caggtgcttc tggtacagtc tggggctgag gtgaagaagc ctggggccac agtgaaggtc            60
tcctgcaagg cttctggatc cactttcacc ggctactata tgcactgggt gcgacaggcc           120
cctggacaag gcttgagtg gatgggatgg atcaaccta acaatggtgg cacaaactat            180
gcacagaagt tcagggcag ggtcaccatg accagggaca cgtccatcag cacagcctac            240
atggaattga gcaggctgag atctgacgac acggccgtat attactgtgc gagagagttg           300
cggtataact ggaagtcctg gggccaggga accctggtca ccgtctcctc a                    351

<210> SEQ ID NO 34
<211> LENGTH: 117
<212> TYPE: PRT
<213> ORGANISM: Artificial Sequence
<220> FEATURE:
<223> OTHER INFORMATION: Synthetic

<400> SEQUENCE: 34
```

Gln Val Leu Val Gln Ser Gly Ala Glu Val Lys Lys Pro Gly Ala
1               5                   10                  15

Thr Val Lys Val Ser Cys Lys Ala Ser Gly Ser Thr Phe Thr Gly Tyr
            20                  25                  30

Tyr Met His Trp Val Arg Gln Ala Pro Gly Gln Gly Leu Glu Trp Met
            35                  40                  45

Gly Trp Ile Asn Pro Asn Asn Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Leu Arg Tyr Asn Trp Lys Ser Trp Gly Gln Gly Thr Leu
            100                 105                 110

Val Thr Val Ser Ser
        115

<210> SEQ ID NO 35
<211> LENGTH: 24
<212> TYPE: DNA
<213> ORGANISM: Artificial Sequence
<220> FEATURE:
<223> OTHER INFORMATION: Synthetic

<400> SEQUENCE: 35
ggatccactt tcaccggcta ctat                                      24

<210> SEQ ID NO 36
<211> LENGTH: 8
<212> TYPE: PRT
<213> ORGANISM: Artificial Sequence
<220> FEATURE:
<223> OTHER INFORMATION: Synthetic

<400> SEQUENCE: 36

Gly Ser Thr Phe Thr Gly Tyr Tyr
1               5

<210> SEQ ID NO 37
<211> LENGTH: 24
<212> TYPE: DNA
<213> ORGANISM: Artificial Sequence
<220> FEATURE:
<223> OTHER INFORMATION: Synthetic

<400> SEQUENCE: 37
atcaacccta acaatggtgg caca                                      24

<210> SEQ ID NO 38
<211> LENGTH: 8
<212> TYPE: PRT
<213> ORGANISM: Artificial Sequence
<220> FEATURE:
<223> OTHER INFORMATION: Synthetic

<400> SEQUENCE: 38

Ile Asn Pro Asn Asn Gly Gly Thr
1               5

<210> SEQ ID NO 39
<211> LENGTH: 30
<212> TYPE: DNA

```
<213> ORGANISM: Artificial Sequence
<220> FEATURE:
<223> OTHER INFORMATION: Synthetic

<400> SEQUENCE: 39
gcgagagagt tgcggtataa ctggaagtcc                                              30

<210> SEQ ID NO 40
<211> LENGTH: 10
<212> TYPE: PRT
<213> ORGANISM: Artificial Sequence
<220> FEATURE:
<223> OTHER INFORMATION: Synthetic

<400> SEQUENCE: 40

Ala Arg Glu Leu Arg Tyr Asn Trp Lys Ser
1               5                   10

<210> SEQ ID NO 41
<211> LENGTH: 324
<212> TYPE: DNA
<213> ORGANISM: Artificial Sequence
<220> FEATURE:
<223> OTHER INFORMATION: Synthetic

<400> SEQUENCE: 41
gaaattgtgt tgacgcagtc tccaggcacc ctgtctttgt ctccagggga aagagtcacc             60
ctctcctgca gggccagtca gagtgttggc aggccctact tagcctggta ccaacagata            120
cctggccagg ctcccaggct cctcatctat ggtgcatcca gcagggccac tgacatccca            180
gacaggttca gtggcaatgg gtctgggaca gacttcactc tcaccatcag tagactggag            240
cctgaagatt ttgcagtgta ttactgtcag cagtatgata attccccctta tactttggc            300 caggggacca ggctggagat caaa                                                    324

<210> SEQ ID NO 42
<211> LENGTH: 108
<212> TYPE: PRT
<213> ORGANISM: Artificial Sequence
<220> FEATURE:
<223> OTHER INFORMATION: Synthetic

<400> SEQUENCE: 42

Glu Ile Val Leu Thr Gln Ser Pro Gly Thr Leu Ser Leu Ser Pro Gly
1               5                   10                  15

Glu Arg Val Thr Leu Ser Cys Arg Ala Ser Gln Ser Val Gly Arg Pro
            20                  25                  30

Tyr Leu Ala Trp Tyr Gln Gln Ile Pro Gly Gln Ala Pro Arg Leu Leu
        35                  40                  45

Ile Tyr Gly Ala Ser Ser Arg Ala Thr Asp Ile Pro Asp Arg Phe Ser
    50                  55                  60

Gly Asn Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Asp Asn Ser Pro
                85                  90                  95

Tyr Thr Phe Gly Gln Gly Thr Arg Leu Glu Ile Lys
            100                 105

<210> SEQ ID NO 43
<211> LENGTH: 21
<212> TYPE: DNA
<213> ORGANISM: Artificial Sequence
```

<220> FEATURE:
<223> OTHER INFORMATION: Synthetic

<400> SEQUENCE: 43
cagagtgttg gcaggcccta c                                                    21

<210> SEQ ID NO 44
<211> LENGTH: 7
<212> TYPE: PRT
<213> ORGANISM: Artificial Sequence
<220> FEATURE:
<223> OTHER INFORMATION: Synthetic

<400> SEQUENCE: 44

Gln Ser Val Gly Arg Pro Tyr
1               5

<210> SEQ ID NO 45
<211> LENGTH: 9
<212> TYPE: DNA
<213> ORGANISM: Artificial Sequence
<220> FEATURE:
<223> OTHER INFORMATION: Synthetic

<400> SEQUENCE: 45 ggtgcatcc                                                                  9

<210> SEQ ID NO 46
<211> LENGTH: 3
<212> TYPE: PRT
<213> ORGANISM: Artificial Sequence
<220> FEATURE:
<223> OTHER INFORMATION: Synthetic

<400> SEQUENCE: 46

Gly Ala Ser
1

<210> SEQ ID NO 47
<211> LENGTH: 27
<212> TYPE: DNA
<213> ORGANISM: Artificial Sequence
<220> FEATURE:
<223> OTHER INFORMATION: Synthetic

<400> SEQUENCE: 47
cagcagtatg ataattcccc ttatact                                              27

<210> SEQ ID NO 48
<211> LENGTH: 9
<212> TYPE: PRT
<213> ORGANISM: Artificial Sequence
<220> FEATURE:
<223> OTHER INFORMATION: Synthetic

<400> SEQUENCE: 48

Gln Gln Tyr Asp Asn Ser Pro Tyr Thr
1               5

<210> SEQ ID NO 49
<211> LENGTH: 366
<212> TYPE: DNA
<213> ORGANISM: Artificial Sequence
<220> FEATURE:
<223> OTHER INFORMATION: Synthetic

<400> SEQUENCE: 49

```
gaggtgcagc tggtggagtc tggggggaggc ttggtacaac ctgggggtc cctgagactc      60 tcctgtgcag cctctggatt caccttaga agctttgcca tgagctgggt ccgccaggct      120
ccagggaagg ggctggaatt ggtctcagat ctcaggacta gtggtggtag tacatactac      180
gcagactccg tgaagggccg gctcaccatc tccagagaca attccaagaa cacgctgtat      240
ctgcaaatga acagcctgag agccgaggac acggccgtat attactgtgc gaaaagccac      300
tatagcacca gctggttcgg gggctttgac tactggggcc agggaaccct ggtcactgtc      360
tcctca                                                                 366
```

```
<210> SEQ ID NO 50
<211> LENGTH: 122
<212> TYPE: PRT
<213> ORGANISM: Artificial Sequence
<220> FEATURE:
<223> OTHER INFORMATION: Synthetic

<400> SEQUENCE: 50
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Ser Phe
            20                  25                  30

Ala Met Ser Trp Val Arg Gln Ala Pro Gly Lys Gly Leu Glu Leu Val
        35                  40                  45

Ser Asp Leu Arg Thr Ser Gly Gly Ser Thr Tyr Tyr Ala Asp Ser Val
    50                  55                  60

Lys Gly Arg Leu Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser His Tyr Ser Thr Ser Trp Phe Gly Gly Phe Asp Tyr Trp
            100                 105                 110

Gly Gln Gly Thr Leu Val Thr Val Ser Ser
        115                 120

```
<210> SEQ ID NO 51
<211> LENGTH: 24
<212> TYPE: DNA
<213> ORGANISM: Artificial Sequence
<220> FEATURE:
<223> OTHER INFORMATION: Synthetic

<400> SEQUENCE: 51
ggattcacct ttagaagctt tgcc                                             24

<210> SEQ ID NO 52
<211> LENGTH: 8
<212> TYPE: PRT
<213> ORGANISM: Artificial Sequence
<220> FEATURE:
<223> OTHER INFORMATION: Synthetic

<400> SEQUENCE: 52
```

Gly Phe Thr Phe Arg Ser Phe Ala
1               5

```
<210> SEQ ID NO 53
<211> LENGTH: 24
<212> TYPE: DNA
<213> ORGANISM: Artificial Sequence
```

```
<220> FEATURE:
<223> OTHER INFORMATION: Synthetic

<400> SEQUENCE: 53
ctcaggacta gtggtggtag taca                                              24

<210> SEQ ID NO 54
<211> LENGTH: 8
<212> TYPE: PRT
<213> ORGANISM: Artificial Sequence
<220> FEATURE:
<223> OTHER INFORMATION: Synthetic

<400> SEQUENCE: 54

Leu Arg Thr Ser Gly Gly Ser Thr
1               5

<210> SEQ ID NO 55
<211> LENGTH: 45
<212> TYPE: DNA
<213> ORGANISM: Artificial Sequence
<220> FEATURE:
<223> OTHER INFORMATION: Synthetic

<400> SEQUENCE: 55
gcgaaaagcc actatagcac cagctggttc gggggctttg actac                       45

<210> SEQ ID NO 56
<211> LENGTH: 15
<212> TYPE: PRT
<213> ORGANISM: Artificial Sequence
<220> FEATURE:
<223> OTHER INFORMATION: Synthetic

<400> SEQUENCE: 56

Ala Lys Ser His Tyr Ser Thr Ser Trp Phe Gly Gly Phe Asp Tyr
1               5                   10                  15

<210> SEQ ID NO 57
<211> LENGTH: 321
<212> TYPE: DNA
<213> ORGANISM: Artificial Sequence
<220> FEATURE:
<223> OTHER INFORMATION: Synthetic

<400> SEQUENCE: 57
gacatccaga tgacccagtc tccatcttcc gtgtctgctt ctgtaggaga cagagtcacc        60
atcacttgtc gggcgagtca gggttttagc agctggttag cctggtatca gcagaaacca      120
gggaaagccc ctaagctcct gatctatgct gcatccagtt tgcaaagtgg ggtcccatca      180
aggttcagcg gcagtggatc tgggacagat ttcactctca ccatcaccaa cctgcagcct      240
gaagattttg caacttacta ttgtcaacag gctaacagtt tccctctcac tttcggcgga      300
gggaccaagg tggagatcaa a                                                321

<210> SEQ ID NO 58
<211> LENGTH: 107
<212> TYPE: PRT
<213> ORGANISM: Artificial Sequence
<220> FEATURE:
<223> OTHER INFORMATION: Synthetic

<400> SEQUENCE: 58

Asp Ile Gln Met Thr Gln Ser Pro Ser Ser Val Ser Ala Ser Val Gly
1               5                   10                  15
```

Asp Arg Val Thr Ile Thr Cys Arg Ala Ser Gln Gly Phe Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Thr Asn Leu Gln Pro
65                  70                  75                  80

Glu Asp Phe Ala Thr Tyr Tyr Cys Gln Gln Ala Asn Ser Phe Pro Leu
                85                  90                  95

Thr Phe Gly Gly Gly Thr Lys Val Glu Ile Lys
            100                 105

<210> SEQ ID NO 59
<211> LENGTH: 18
<212> TYPE: DNA
<213> ORGANISM: Artificial Sequence
<220> FEATURE:
<223> OTHER INFORMATION: Synthetic

<400> SEQUENCE: 59 cagggttttta gcagctgg                                              18

<210> SEQ ID NO 60
<211> LENGTH: 6
<212> TYPE: PRT
<213> ORGANISM: Artificial Sequence
<220> FEATURE:
<223> OTHER INFORMATION: Synthetic

<400> SEQUENCE: 60

Gln Gly Phe Ser Ser Trp
1               5

<210> SEQ ID NO 61
<211> LENGTH: 9
<212> TYPE: DNA
<213> ORGANISM: Artificial Sequence
<220> FEATURE:
<223> OTHER INFORMATION: Synthetic

<400> SEQUENCE: 61 gctgcatcc                                                          9

<210> SEQ ID NO 62
<211> LENGTH: 3
<212> TYPE: PRT
<213> ORGANISM: Artificial Sequence
<220> FEATURE:
<223> OTHER INFORMATION: Synthetic

<400> SEQUENCE: 62

Ala Ala Ser
1

<210> SEQ ID NO 63
<211> LENGTH: 27
<212> TYPE: DNA
<213> ORGANISM: Artificial Sequence
<220> FEATURE:
<223> OTHER INFORMATION: Synthetic

<400> SEQUENCE: 63

```
caacaggcta acagtttccc tctcact                                              27
```

<210> SEQ ID NO 64
<211> LENGTH: 9
<212> TYPE: PRT
<213> ORGANISM: Artificial Sequence
<220> FEATURE:
<223> OTHER INFORMATION: Synthetic

<400> SEQUENCE: 64

Gln Gln Ala Asn Ser Phe Pro Leu Thr
1               5

<210> SEQ ID NO 65
<211> LENGTH: 366
<212> TYPE: DNA
<213> ORGANISM: Artificial Sequence
<220> FEATURE:
<223> OTHER INFORMATION: Synthetic

<400> SEQUENCE: 65

```
gaggtgcagc tggtggagtc tgggggaggc ttggtacagc ctggggggtc cctgagactc    60
tcctgtgcag cctctggatt cacgtttagc agctatgtca tgagctgggt ccgccaggct   120
ccagggaagg ggctggagtg ggtctcaagt attagtggta atggtggtag cacaaactac   180
gcagactccg tgaagggccg gttcaccatc tccagagaca attccaagaa cacgctgttt   240
ctggaaatga acagcctgag agccgaggac acggccgtat attactgtgc gaaatcactg   300
ggaactacca cgactttttt ggggtttgac tattggggcc agggaaccct ggtcaccgtc   360
tcctca                                                              366
```

<210> SEQ ID NO 66
<211> LENGTH: 122
<212> TYPE: PRT
<213> ORGANISM: Artificial Sequence
<220> FEATURE:
<223> OTHER INFORMATION: Synthetic

<400> SEQUENCE: 66

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Val Met Ser Trp Val Arg Gln Ala Pro Gly Lys Gly Leu Glu Trp Val
        35                  40                  45

Ser Ser Ile Ser Gly Asn Gly Gly Ser Thr Asn Tyr Ala Asp Ser Val
    50                  55                  60

Lys Gly Arg Phe Thr Ile Ser Arg Asp Asn Ser Lys Asn Thr Leu Phe
65                  70                  75                  80

Leu Glu Met Asn Ser Leu Arg Ala Glu Asp Thr Ala Val Tyr Tyr Cys
                85                  90                  95

Ala Lys Ser Leu Gly Thr Thr Thr Thr Phe Leu Gly Phe Asp Tyr Trp
            100                 105                 110

Gly Gln Gly Thr Leu Val Thr Val Ser Ser
        115                 120

<210> SEQ ID NO 67
<211> LENGTH: 24
<212> TYPE: DNA
<213> ORGANISM: Artificial Sequence
<220> FEATURE:

<223> OTHER INFORMATION: Synthetic

<400> SEQUENCE: 67
ggattcacgt ttagcagcta tgtc                                    24

<210> SEQ ID NO 68
<211> LENGTH: 8
<212> TYPE: PRT
<213> ORGANISM: Artificial Sequence
<220> FEATURE:
<223> OTHER INFORMATION: Synthetic

<400> SEQUENCE: 68

Gly Phe Thr Phe Ser Ser Tyr Val
1               5

<210> SEQ ID NO 69
<211> LENGTH: 24
<212> TYPE: DNA
<213> ORGANISM: Artificial Sequence
<220> FEATURE:
<223> OTHER INFORMATION: Synthetic

<400> SEQUENCE: 69
attagtggta atggtggtag caca                                    24

<210> SEQ ID NO 70
<211> LENGTH: 8
<212> TYPE: PRT
<213> ORGANISM: Artificial Sequence
<220> FEATURE:
<223> OTHER INFORMATION: Synthetic

<400> SEQUENCE: 70

Ile Ser Gly Asn Gly Gly Ser Thr
1               5

<210> SEQ ID NO 71
<211> LENGTH: 45
<212> TYPE: DNA
<213> ORGANISM: Artificial Sequence
<220> FEATURE:
<223> OTHER INFORMATION: Synthetic

<400> SEQUENCE: 71
gcgaaatcac tgggaactac cacgactttt tgggggtttg actat             45

<210> SEQ ID NO 72
<211> LENGTH: 15
<212> TYPE: PRT
<213> ORGANISM: Artificial Sequence
<220> FEATURE:
<223> OTHER INFORMATION: Synthetic

<400> SEQUENCE: 72

Ala Lys Ser Leu Gly Thr Thr Thr Thr Phe Leu Gly Phe Asp Tyr
1               5                   10                  15

<210> SEQ ID NO 73
<211> LENGTH: 321
<212> TYPE: DNA
<213> ORGANISM: Artificial Sequence
<220> FEATURE:
<223> OTHER INFORMATION: Synthetic

<400> SEQUENCE: 73

-continued

```
gacatccaga tgacccagtc tccatcttcc gtgtctgcat ctgtaggaga cagagtcacc    60
atcacttgtc gggcgagtca gggtattagc agctggttag cctggtatca gcagaaacca   120
gggaaagccc ctaaactcct gatctatgct gcatccagtt tgcaaagtgg ggtcccatca   180
aggttcagcg gcagtggatc tgggacatat ttcactctca ccatcagcag cctgcagcct   240
gaagattttg caacttacta ttgtcaacag gctaacagtt tccctctcac tttcggcgga   300
gggaccaagg tggagatcaa a                                             321
```

<210> SEQ ID NO 74
<211> LENGTH: 107
<212> TYPE: PRT
<213> ORGANISM: Artificial Sequence
<220> FEATURE:
<223> OTHER INFORMATION: Synthetic

<400> SEQUENCE: 74

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Tyr Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Leu
                85                  90                  95

Thr Phe Gly Gly Gly Thr Lys Val Glu Ile Lys
            100                 105

<210> SEQ ID NO 75
<211> LENGTH: 18
<212> TYPE: DNA
<213> ORGANISM: Artificial Sequence
<220> FEATURE:
<223> OTHER INFORMATION: Synthetic

<400> SEQUENCE: 75

```
cagggtatta gcagctgg                                                  18
```

<210> SEQ ID NO 76
<211> LENGTH: 6
<212> TYPE: PRT
<213> ORGANISM: Artificial Sequence
<220> FEATURE:
<223> OTHER INFORMATION: Synthetic

<400> SEQUENCE: 76

Gln Gly Ile Ser Ser Trp
1               5

<210> SEQ ID NO 77
<211> LENGTH: 9
<212> TYPE: DNA
<213> ORGANISM: Artificial Sequence
<220> FEATURE:
<223> OTHER INFORMATION: Synthetic

<400> SEQUENCE: 77

```
gctgcatcc                                                             9
```

<210> SEQ ID NO 78
<211> LENGTH: 3
<212> TYPE: PRT
<213> ORGANISM: Artificial Sequence
<220> FEATURE:
<223> OTHER INFORMATION: Synthetic

<400> SEQUENCE: 78

Ala Ala Ser
1

<210> SEQ ID NO 79
<211> LENGTH: 27
<212> TYPE: DNA
<213> ORGANISM: Artificial Sequence
<220> FEATURE:
<223> OTHER INFORMATION: Synthetic

<400> SEQUENCE: 79
caacaggcta acagtttccc tctcact                                        27

<210> SEQ ID NO 80
<211> LENGTH: 9
<212> TYPE: PRT
<213> ORGANISM: Artificial Sequence
<220> FEATURE:
<223> OTHER INFORMATION: Synthetic

<400> SEQUENCE: 80

Gln Gln Ala Asn Ser Phe Pro Leu Thr
1               5

<210> SEQ ID NO 81
<211> LENGTH: 363
<212> TYPE: DNA
<213> ORGANISM: Artificial Sequence
<220> FEATURE:
<223> OTHER INFORMATION: Synthetic

<400> SEQUENCE: 81
caggtgcagc tgcaggagtc gggcccagga ctggtgaagc cttcggagac cctgtccctc    60
acctgcactg tctctggtgg ctccatcagt agttattact ggagctggat ccggcagccc   120
ccagggaagg gactggagtt gattgggtat atttattaca gtgggagcac caattataac   180
ccctccctca gagtcgagt caccatatct gtagacacgt ccaagaacca cttctccctg   240
aagctgagct ctgtgaccgc tgcggacacg gccgtatatt actgtgcgag atcccagtat   300
accagtagtt ggtacggttc ttttgatatc tggggccaag ggacaatggt caccgtctct   360
tca                                                                 363

<210> SEQ ID NO 82
<211> LENGTH: 121
<212> TYPE: PRT
<213> ORGANISM: Artificial Sequence
<220> FEATURE:
<223> OTHER INFORMATION: Synthetic

<400> SEQUENCE: 82

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Leu Ile
            35                  40                  45

Gly Tyr Ile Tyr Tyr Ser Gly Ser Thr Asn Tyr Asn Pro Ser Leu Lys
 50                  55                  60

Ser Arg Val Thr Ile Ser Val Asp Thr Ser Lys Asn His Phe Ser Leu
65                  70                  75                  80

Lys Leu Ser Ser Val Thr Ala Ala Asp Thr Ala Val Tyr Tyr Cys Ala
                85                  90                  95

Arg Ser Gln Tyr Thr Ser Ser Trp Tyr Gly Ser Phe Asp Ile Trp Gly
            100                 105                 110

Gln Gly Thr Met Val Thr Val Ser Ser
        115                 120

<210> SEQ ID NO 83
<211> LENGTH: 24
<212> TYPE: DNA
<213> ORGANISM: Artificial Sequence
<220> FEATURE:
<223> OTHER INFORMATION: Synthetic

<400> SEQUENCE: 83
ggtggctcca tcagtagtta ttac                                    24

<210> SEQ ID NO 84
<211> LENGTH: 8
<212> TYPE: PRT
<213> ORGANISM: Artificial Sequence
<220> FEATURE:
<223> OTHER INFORMATION: Synthetic

<400> SEQUENCE: 84

Gly Gly Ser Ile Ser Ser Tyr Tyr
1               5

<210> SEQ ID NO 85
<211> LENGTH: 21
<212> TYPE: DNA
<213> ORGANISM: Artificial Sequence
<220> FEATURE:
<223> OTHER INFORMATION: Synthetic

<400> SEQUENCE: 85
atttattaca gtgggagcac c                                       21

<210> SEQ ID NO 86
<211> LENGTH: 7
<212> TYPE: PRT
<213> ORGANISM: Artificial Sequence
<220> FEATURE:
<223> OTHER INFORMATION: Synthetic

<400> SEQUENCE: 86

Ile Tyr Tyr Ser Gly Ser Thr
1               5

<210> SEQ ID NO 87
<211> LENGTH: 45
<212> TYPE: DNA
<213> ORGANISM: Artificial Sequence
<220> FEATURE:
<223> OTHER INFORMATION: Synthetic

<400> SEQUENCE: 87
gcgagatccc agtataccag tagttggtac ggttcttttg atatc              45

<210> SEQ ID NO 88
<211> LENGTH: 15
<212> TYPE: PRT
<213> ORGANISM: Artificial Sequence
<220> FEATURE:
<223> OTHER INFORMATION: Synthetic

<400> SEQUENCE: 88

Ala Arg Ser Gln Tyr Thr Ser Ser Trp Tyr Gly Ser Phe Asp Ile
1               5                   10                  15

<210> SEQ ID NO 89
<211> LENGTH: 321
<212> TYPE: DNA
<213> ORGANISM: Artificial Sequence
<220> FEATURE:
<223> OTHER INFORMATION: Synthetic

<400> SEQUENCE: 89
gacatccaga tgacccagtc tccatcttcc gtgtctgcat ctgtaggaga cagagtcacc    60
atcacttgtc gggcgagtca gggtattagc acctggttag cctggtttca gcagaaacca   120
gggaaagccc ctaagctcct gatctatgct gcatccactt tacaaggtgg ggtcccatca   180
aggttcagcg gcagtggatc tgggccagaa ttcactctca ccatcagcag cctgcagcct   240
gaagattttg caacttacta ttgtcaacag gctaacagtt tcccgtggac gttcggccaa   300
gggaccaagg tggaaatcaa a                                             321

<210> SEQ ID NO 90
<211> LENGTH: 107
<212> TYPE: PRT
<213> ORGANISM: Artificial Sequence
<220> FEATURE:
<223> OTHER INFORMATION: Synthetic

<400> SEQUENCE: 90

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Thr Trp
            20                  25                  30

Leu Ala Trp Phe Gln Gln Lys Pro Gly Lys Ala Pro Lys Leu Leu Ile
        35                  40                  45

Tyr Ala Ala Ser Thr Leu Gln Gly Gly Val Pro Ser Arg Phe Ser Gly
    50                  55                  60

Ser Gly Ser Gly Pro Glu Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Trp
                85                  90                  95

Thr Phe Gly Gln Gly Thr Lys Val Glu Ile Lys
            100                 105

<210> SEQ ID NO 91
<211> LENGTH: 18
<212> TYPE: DNA
<213> ORGANISM: Artificial Sequence
<220> FEATURE:
<223> OTHER INFORMATION: Synthetic

<400> SEQUENCE: 91
cagggtatta gcacctgg                                                  18

```
<210> SEQ ID NO 92
<211> LENGTH: 6
<212> TYPE: PRT
<213> ORGANISM: Artificial Sequence
<220> FEATURE:
<223> OTHER INFORMATION: Synthetic

<400> SEQUENCE: 92

Gln Gly Ile Ser Thr Trp
1               5

<210> SEQ ID NO 93
<211> LENGTH: 9
<212> TYPE: DNA
<213> ORGANISM: Artificial Sequence
<220> FEATURE:
<223> OTHER INFORMATION: Synthetic

<400> SEQUENCE: 93 gctgcatcc                                                              9

<210> SEQ ID NO 94
<211> LENGTH: 3
<212> TYPE: PRT
<213> ORGANISM: Artificial Sequence
<220> FEATURE:
<223> OTHER INFORMATION: Synthetic

<400> SEQUENCE: 94

Ala Ala Ser
1

<210> SEQ ID NO 95
<211> LENGTH: 27
<212> TYPE: DNA
<213> ORGANISM: Artificial Sequence
<220> FEATURE:
<223> OTHER INFORMATION: Synthetic

<400> SEQUENCE: 95
caacaggcta acagtttccc gtggacg                                         27

<210> SEQ ID NO 96
<211> LENGTH: 9
<212> TYPE: PRT
<213> ORGANISM: Artificial Sequence
<220> FEATURE:
<223> OTHER INFORMATION: Synthetic

<400> SEQUENCE: 96

Gln Gln Ala Asn Ser Phe Pro Trp Thr
1               5

<210> SEQ ID NO 97
<211> LENGTH: 366
<212> TYPE: DNA
<213> ORGANISM: Artificial Sequence
<220> FEATURE:
<223> OTHER INFORMATION: Synthetic

<400> SEQUENCE: 97
caggttcagc tggtgcagtc tggagctgag gtgaagaagc ctggggcctc agtgaaggtc     60
tcctgcaagg cctctggtta cacctttaac agctatggta tcagctgggt gcgacaggcc    120
cctggacaag ggcttgagtg gatgggatgg atcagctccc acaatggtaa cagtcactat    180
```

```
gtacagaagt tccagggcag agtctccatg accacagaca catccacgag tacagcctac    240
atggaactga ggagccttag atctgacgac acggccgtgt attactgtgc gagacactcg    300
tataccacca gctggtacgg gggttttgac tattggggcc agggaaccct ggtcaccgtc    360
tcctca                                                                366
```

<210> SEQ ID NO 98
<211> LENGTH: 122
<212> TYPE: PRT
<213> ORGANISM: Artificial Sequence
<220> FEATURE:
<223> OTHER INFORMATION: Synthetic

<400> SEQUENCE: 98

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Asn Ser Tyr
            20                  25                  30

Gly Ile Ser Trp Val Arg Gln Ala Pro Gly Gln Gly Leu Glu Trp Met
        35                  40                  45

Gly Trp Ile Ser Ser His Asn Gly Asn Ser His Tyr Val Gln Lys Phe
    50                  55                  60

Gln Gly Arg Val Ser Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg His Ser Tyr Thr Thr Ser Trp Tyr Gly Gly Phe Asp Tyr Trp
            100                 105                 110

Gly Gln Gly Thr Leu Val Thr Val Ser Ser
        115                 120
```

<210> SEQ ID NO 99
<211> LENGTH: 24
<212> TYPE: DNA
<213> ORGANISM: Artificial Sequence
<220> FEATURE:
<223> OTHER INFORMATION: Synthetic

<400> SEQUENCE: 99

```
ggttacacct ttaacagcta tggt                                            24
```

<210> SEQ ID NO 100
<211> LENGTH: 8
<212> TYPE: PRT
<213> ORGANISM: Artificial Sequence
<220> FEATURE:
<223> OTHER INFORMATION: Synthetic

<400> SEQUENCE: 100

```
Gly Tyr Thr Phe Asn Ser Tyr Gly
1               5
```

<210> SEQ ID NO 101
<211> LENGTH: 24
<212> TYPE: DNA
<213> ORGANISM: Artificial Sequence
<220> FEATURE:
<223> OTHER INFORMATION: Synthetic

<400> SEQUENCE: 101

```
atcagctccc acaatggtaa cagt                                            24
```

<210> SEQ ID NO 102
<211> LENGTH: 8
<212> TYPE: PRT
<213> ORGANISM: Artificial Sequence
<220> FEATURE:
<223> OTHER INFORMATION: Synthetic

<400> SEQUENCE: 102

Ile Ser Ser His Asn Gly Asn Ser
1               5

<210> SEQ ID NO 103
<211> LENGTH: 45
<212> TYPE: DNA
<213> ORGANISM: Artificial Sequence
<220> FEATURE:
<223> OTHER INFORMATION: Synthetic

<400> SEQUENCE: 103
gcgagacact cgtataccac cagctggtac gggggttttg actat              45

<210> SEQ ID NO 104
<211> LENGTH: 15
<212> TYPE: PRT
<213> ORGANISM: Artificial Sequence
<220> FEATURE:
<223> OTHER INFORMATION: Synthetic

<400> SEQUENCE: 104

Ala Arg His Ser Tyr Thr Thr Ser Trp Tyr Gly Gly Phe Asp Tyr
1               5                   10                  15

<210> SEQ ID NO 105
<211> LENGTH: 321
<212> TYPE: DNA
<213> ORGANISM: Artificial Sequence
<220> FEATURE:
<223> OTHER INFORMATION: Synthetic

<400> SEQUENCE: 105
gacatccaga tgacccagtc tccatcttcc gtgtctgcat ctgtaggaga cagagtcacc     60
atcacttgtc gggcgagtca gggttttagc agctggttag cctggtatca gcagaaacca    120
gggaaagccc ctcagctcct gatctatgct gcatccagtt tgcaaagtgg ggtcccatca    180
aggttcagcg gcagtggatc tgggtcagat ttcactctca ccatcagcag cctgcagcct    240
gaagattttg caacttacta ttgtcaacag gctaacagtt tccctctcac tttcggcgga    300
gggaccaagg tggagatcaa a                                              321

<210> SEQ ID NO 106
<211> LENGTH: 107
<212> TYPE: PRT
<213> ORGANISM: Artificial Sequence
<220> FEATURE:
<223> OTHER INFORMATION: Synthetic

<400> SEQUENCE: 106

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Phe Ser Ser Trp
            20                  25                  30

Leu Ala Trp Tyr Gln Gln Lys Pro Gly Lys Ala Pro Gln Leu Leu Ile
        35                  40                  45

```
Tyr Ala Ala Ser Ser Leu Gln Ser Gly Val Pro Ser Arg Phe Ser Gly
        50                  55                  60

Ser Gly Ser Gly Ser Asp Phe Thr Leu Thr Ile Ser Ser Leu Gln Pro
 65                  70                  75                  80

Glu Asp Phe Ala Thr Tyr Tyr Cys Gln Gln Ala Asn Ser Phe Pro Leu
                 85                  90                  95

Thr Phe Gly Gly Gly Thr Lys Val Glu Ile Lys
                100                 105

<210> SEQ ID NO 107
<211> LENGTH: 18
<212> TYPE: DNA
<213> ORGANISM: Artificial Sequence
<220> FEATURE:
<223> OTHER INFORMATION: Synthetic

<400> SEQUENCE: 107
cagggtttta gcagctgg                                                       18

<210> SEQ ID NO 108
<211> LENGTH: 6
<212> TYPE: PRT
<213> ORGANISM: Artificial Sequence
<220> FEATURE:
<223> OTHER INFORMATION: Synthetic

<400> SEQUENCE: 108

Gln Gly Phe Ser Ser Trp
 1               5

<210> SEQ ID NO 109
<211> LENGTH: 9
<212> TYPE: DNA
<213> ORGANISM: Artificial Sequence
<220> FEATURE:
<223> OTHER INFORMATION: Synthetic

<400> SEQUENCE: 109 gctgcatcc                                                                  9

<210> SEQ ID NO 110
<211> LENGTH: 3
<212> TYPE: PRT
<213> ORGANISM: Artificial Sequence
<220> FEATURE:
<223> OTHER INFORMATION: Synthetic

<400> SEQUENCE: 110

Ala Ala Ser
 1

<210> SEQ ID NO 111
<211> LENGTH: 27
<212> TYPE: DNA
<213> ORGANISM: Artificial Sequence
<220> FEATURE:
<223> OTHER INFORMATION: Synthetic

<400> SEQUENCE: 111
caacaggcta acagtttccc tctcact                                             27

<210> SEQ ID NO 112
<211> LENGTH: 9
<212> TYPE: PRT
<213> ORGANISM: Artificial Sequence
```

<220> FEATURE:
<223> OTHER INFORMATION: Synthetic

<400> SEQUENCE: 112

Gln Gln Ala Asn Ser Phe Pro Leu Thr
1               5

<210> SEQ ID NO 113
<211> LENGTH: 366
<212> TYPE: DNA
<213> ORGANISM: Artificial Sequence
<220> FEATURE:
<223> OTHER INFORMATION: Synthetic

<400> SEQUENCE: 113

```
gaggtgcagc tggtggagtc cggggggaggc ttggttcagc cggggggggtc cctgagactc      60 tcctgtgcag cctctggaat caccttgagc agctatggca tgagctgggt ccgccaggct     120
ccagggaagg gactggagtg ggtcgcatcc attttggta gtggtggtgg cccatactac     180
gcagactccg tgaagggccg gttcaccatg tccagagaca attccaagaa cacgctgtat     240
ttgcaaatga acagcctgag agccgaggac acggccgtat attattgtgc gaaagatcga     300
tacagtggga gctactacgg aggttttgac tactggggcc ggggaaccct ggtcaccgtc     360
tcctca                                                                366
```

<210> SEQ ID NO 114
<211> LENGTH: 122
<212> TYPE: PRT
<213> ORGANISM: Artificial Sequence
<220> FEATURE:
<223> OTHER INFORMATION: Synthetic

<400> SEQUENCE: 114

Glu Val Gln Leu Val Glu Ser Gly Gly Gly Leu Val Gln Pro Gly Gly
1               5                   10                  15

Ser Leu Arg Leu Ser Cys Ala Ala Ser Gly Ile Thr Leu Ser Ser Tyr
            20                  25                  30

Gly Met Ser Trp Val Arg Gln Ala Pro Gly Lys Gly Leu Glu Trp Val
        35                  40                  45

Ala Ser Ile Phe Gly Ser Gly Gly Pro Tyr Tyr Ala Asp Ser Val
    50                  55                  60

Lys Gly Arg Phe Thr Met Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Tyr Ser Gly Ser Tyr Tyr Gly Gly Phe Asp Tyr Trp
            100                 105                 110

Gly Arg Gly Thr Leu Val Thr Val Ser Ser
        115                 120

<210> SEQ ID NO 115
<211> LENGTH: 24
<212> TYPE: DNA
<213> ORGANISM: Artificial Sequence
<220> FEATURE:
<223> OTHER INFORMATION: Synthetic

<400> SEQUENCE: 115

```
ggaatcaccct tgagcagcta tggc                                            24
```

<210> SEQ ID NO 116
<211> LENGTH: 8
<212> TYPE: PRT
<213> ORGANISM: Artificial Sequence
<220> FEATURE:
<223> OTHER INFORMATION: Synthetic

<400> SEQUENCE: 116

Gly Ile Thr Leu Ser Ser Tyr Gly
1               5

<210> SEQ ID NO 117
<211> LENGTH: 24
<212> TYPE: DNA
<213> ORGANISM: Artificial Sequence
<220> FEATURE:
<223> OTHER INFORMATION: Synthetic

<400> SEQUENCE: 117
atttttggta gtggtggtgg ccca                                          24

<210> SEQ ID NO 118
<211> LENGTH: 8
<212> TYPE: PRT
<213> ORGANISM: Artificial Sequence
<220> FEATURE:
<223> OTHER INFORMATION: Synthetic

<400> SEQUENCE: 118

Ile Phe Gly Ser Gly Gly Gly Pro
1               5

<210> SEQ ID NO 119
<211> LENGTH: 45
<212> TYPE: DNA
<213> ORGANISM: Artificial Sequence
<220> FEATURE:
<223> OTHER INFORMATION: Synthetic

<400> SEQUENCE: 119
gcgaaagatc gatacagtgg gagctactac ggaggttttg actac                   45

<210> SEQ ID NO 120
<211> LENGTH: 15
<212> TYPE: PRT
<213> ORGANISM: Artificial Sequence
<220> FEATURE:
<223> OTHER INFORMATION: Synthetic

<400> SEQUENCE: 120

Ala Lys Asp Arg Tyr Ser Gly Ser Tyr Tyr Gly Gly Phe Asp Tyr
1               5                   10                  15

<210> SEQ ID NO 121
<211> LENGTH: 321
<212> TYPE: DNA
<213> ORGANISM: Artificial Sequence
<220> FEATURE:
<223> OTHER INFORMATION: Synthetic

<400> SEQUENCE: 121
gacatccaga tgacccagtc tccatcttcc gtgtctgcat ctgtaggaga cagagtcacc   60
atcacttgtc gggcgagtca gggtattacc agctggttag cctggtatca gcagaaacca  120
gggaaagccc ctacactcct gatctatgct gcatccagtt tgcaaactgg ggtcccatca  180
aggttcagcg gcagtggatc tgggacagat ttcactctca ccatcagcag cctgcagcct  240

```
gaacattttg caacttacta ttgtcaacag gctaacagtt tccctcctac tttcggcgga    300
gggaccaagg tggagatcaa a                                              321
```

<210> SEQ ID NO 122
<211> LENGTH: 107
<212> TYPE: PRT
<213> ORGANISM: Artificial Sequence
<220> FEATURE:
<223> OTHER INFORMATION: Synthetic

<400> SEQUENCE: 122

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Thr Ser Trp
            20                  25                  30

Leu Ala Trp Tyr Gln Gln Lys Pro Gly Lys Ala Pro Thr Leu Leu Ile
        35                  40                  45

Tyr Ala Ala Ser Ser Leu Gln Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu His Phe Ala Thr Tyr Tyr Cys Gln Gln Ala Asn Ser Phe Pro Pro
                85                  90                  95

Thr Phe Gly Gly Gly Thr Lys Val Glu Ile Lys
            100                 105
```

<210> SEQ ID NO 123
<211> LENGTH: 18
<212> TYPE: DNA
<213> ORGANISM: Artificial Sequence
<220> FEATURE:
<223> OTHER INFORMATION: Synthetic

<400> SEQUENCE: 123

```
cagggtatta ccagctgg                                                  18
```

<210> SEQ ID NO 124
<211> LENGTH: 6
<212> TYPE: PRT
<213> ORGANISM: Artificial Sequence
<220> FEATURE:
<223> OTHER INFORMATION: Synthetic

<400> SEQUENCE: 124

```
Gln Gly Ile Thr Ser Trp
1               5
```

<210> SEQ ID NO 125
<211> LENGTH: 9
<212> TYPE: DNA
<213> ORGANISM: Artificial Sequence
<220> FEATURE:
<223> OTHER INFORMATION: Synthetic

<400> SEQUENCE: 125

```
gctgcatcc                                                             9
```

<210> SEQ ID NO 126
<211> LENGTH: 3
<212> TYPE: PRT
<213> ORGANISM: Artificial Sequence
<220> FEATURE:

<223> OTHER INFORMATION: Synthetic

<400> SEQUENCE: 126

Ala Ala Ser
1

<210> SEQ ID NO 127
<211> LENGTH: 27
<212> TYPE: DNA
<213> ORGANISM: Artificial Sequence
<220> FEATURE:
<223> OTHER INFORMATION: Synthetic

<400> SEQUENCE: 127

```
caacaggcta acagtttccc tcctact                                              27
```

<210> SEQ ID NO 128
<211> LENGTH: 9
<212> TYPE: PRT
<213> ORGANISM: Artificial Sequence
<220> FEATURE:
<223> OTHER INFORMATION: Synthetic

<400> SEQUENCE: 128

Gln Gln Ala Asn Ser Phe Pro Pro Thr
1               5

<210> SEQ ID NO 129
<211> LENGTH: 366
<212> TYPE: DNA
<213> ORGANISM: Artificial Sequence
<220> FEATURE:
<223> OTHER INFORMATION: Synthetic

<400> SEQUENCE: 129

```
gaggtgcagc tggtggagtc tgggggaggc ttggtacagc ctggggggtc cctaagactc          60
tcctgtgcag cctctggatt cacctttagc agttatgcct tgacctgggt ccgccaggct         120
ccagggaagg ggctggagtg ggtctctttt attagtggta gtggtggtag gccattctac         180
gcagactccg tgaagggccg gttcaccatc tccagagaca attccaagaa catgctgtat         240
ctgcaaatga acagcctgag agccgaggac acggccatat attactgtgc gaagtccctg         300
tataccacca gctggtacgg ggggttcgac tcctggggcc agggaacccct ggtcaccgtc         360
tcctca                                                                   366
```

<210> SEQ ID NO 130
<211> LENGTH: 122
<212> TYPE: PRT
<213> ORGANISM: Artificial Sequence
<220> FEATURE:
<223> OTHER INFORMATION: Synthetic

<400> SEQUENCE: 130

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Leu Thr Trp Val Arg Gln Ala Pro Gly Lys Gly Leu Glu Trp Val
        35                  40                  45

Ser Phe Ile Ser Gly Ser Gly Gly Arg Pro Tyr Ala Asp Ser Val
    50                  55                  60

Lys Gly Arg Phe Thr Ile Ser Arg Asp Asn Ser Lys Asn Met Leu Tyr

```
            65                  70                  75                  80
Leu Gln Met Asn Ser Leu Arg Ala Glu Asp Thr Ala Ile Tyr Tyr Cys
                    85                  90                  95
Ala Lys Ser Leu Tyr Thr Thr Ser Trp Tyr Gly Gly Phe Asp Ser Trp
                100                 105                 110
Gly Gln Gly Thr Leu Val Thr Val Ser Ser
            115                 120
```

<210> SEQ ID NO 131
<211> LENGTH: 24
<212> TYPE: DNA
<213> ORGANISM: Artificial Sequence
<220> FEATURE:
<223> OTHER INFORMATION: Synthetic

<400> SEQUENCE: 131
ggattcacct ttagcagtta tgcc                                           24

<210> SEQ ID NO 132
<211> LENGTH: 8
<212> TYPE: PRT
<213> ORGANISM: Artificial Sequence
<220> FEATURE:
<223> OTHER INFORMATION: Synthetic

<400> SEQUENCE: 132

Gly Phe Thr Phe Ser Ser Tyr Ala
1               5

<210> SEQ ID NO 133
<211> LENGTH: 24
<212> TYPE: DNA
<213> ORGANISM: Artificial Sequence
<220> FEATURE:
<223> OTHER INFORMATION: Synthetic

<400> SEQUENCE: 133
attagtggta gtggtggtag gcca                                           24

<210> SEQ ID NO 134
<211> LENGTH: 8
<212> TYPE: PRT
<213> ORGANISM: Artificial Sequence
<220> FEATURE:
<223> OTHER INFORMATION: Synthetic

<400> SEQUENCE: 134

Ile Ser Gly Ser Gly Gly Arg Pro
1               5

<210> SEQ ID NO 135
<211> LENGTH: 45
<212> TYPE: DNA
<213> ORGANISM: Artificial Sequence
<220> FEATURE:
<223> OTHER INFORMATION: Synthetic

<400> SEQUENCE: 135
gcgaagtccc tgtataccac cagctggtac gggggggttcg actcc                   45

<210> SEQ ID NO 136
<211> LENGTH: 15
<212> TYPE: PRT
<213> ORGANISM: Artificial Sequence
<220> FEATURE:

<223> OTHER INFORMATION: Synthetic

<400> SEQUENCE: 136

Ala Lys Ser Leu Tyr Thr Thr Ser Trp Tyr Gly Gly Phe Asp Ser
1               5                   10                  15

<210> SEQ ID NO 137
<211> LENGTH: 321
<212> TYPE: DNA
<213> ORGANISM: Artificial Sequence
<220> FEATURE:
<223> OTHER INFORMATION: Synthetic

<400> SEQUENCE: 137
gacatccaga tgacccagtc tccatcttcc gtgtctgcat ctgtaggaga cagagtcacc    60
atcacttgtc gggcgagtca gggtgtcgtc agctggttag cctggtatca gcagaaacca   120
gggaaagccc ctaagctcct gatctatgct gcatccagtt tgcaaagtgg ggtcccatca   180
aggttcagcg gcagtggatc tgggacagat ttcactctca ccatcagcag cctgcagcct   240
gaagattttg caacttatta ttgtcaacag tctaacagtt tccctttcac tctcggccct   300
gggaccaaag tggatatcaa a                                             321

<210> SEQ ID NO 138
<211> LENGTH: 107
<212> TYPE: PRT
<213> ORGANISM: Artificial Sequence
<220> FEATURE:
<223> OTHER INFORMATION: Synthetic

<400> SEQUENCE: 138

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Val Val Ser Trp
                20                  25                  30

Leu Ala Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asn Ser Phe Pro Phe
                85                  90                  95

Thr Leu Gly Pro Gly Thr Lys Val Asp Ile Lys
            100                 105

<210> SEQ ID NO 139
<211> LENGTH: 18
<212> TYPE: DNA
<213> ORGANISM: Artificial Sequence
<220> FEATURE:
<223> OTHER INFORMATION: Synthetic

<400> SEQUENCE: 139
cagggtgtcg tcagctgg                                                  18

<210> SEQ ID NO 140
<211> LENGTH: 6
<212> TYPE: PRT
<213> ORGANISM: Artificial Sequence
<220> FEATURE:
<223> OTHER INFORMATION: Synthetic

<400> SEQUENCE: 140

Gln Gly Val Val Ser Trp
1               5

<210> SEQ ID NO 141
<211> LENGTH: 9
<212> TYPE: DNA
<213> ORGANISM: Artificial Sequence
<220> FEATURE:
<223> OTHER INFORMATION: Synthetic

<400> SEQUENCE: 141 gctgcatcc                                                                 9

<210> SEQ ID NO 142
<211> LENGTH: 3
<212> TYPE: PRT
<213> ORGANISM: Artificial Sequence
<220> FEATURE:
<223> OTHER INFORMATION: Synthetic

<400> SEQUENCE: 142

Ala Ala Ser
1

<210> SEQ ID NO 143
<211> LENGTH: 24
<212> TYPE: DNA
<213> ORGANISM: Artificial Sequence
<220> FEATURE:
<223> OTHER INFORMATION: Synthetic

<400> SEQUENCE: 143
caacagtcta acagtttccc tttc                                               24

<210> SEQ ID NO 144
<211> LENGTH: 8
<212> TYPE: PRT
<213> ORGANISM: Artificial Sequence
<220> FEATURE:
<223> OTHER INFORMATION: Synthetic

<400> SEQUENCE: 144

Gln Gln Ser Asn Ser Phe Pro Phe
1               5

<210> SEQ ID NO 145
<211> LENGTH: 366
<212> TYPE: DNA
<213> ORGANISM: Artificial Sequence
<220> FEATURE:
<223> OTHER INFORMATION: Synthetic

<400> SEQUENCE: 145
caggtgcagc tggtgcagtc tggggctgaa gtgaagaagc ctggggcctc agtgaaggtc    60
tcctgcaagg cttctggata caccttcacc ggccactata tgtactggat cgacaggcc   120 cctggacaag gcttgagtg gatgggatgg atcaaccta acagtggtgg cacaaactat    180
gcacagaagt ttcaggacag ggtcaccatg accagggaca cgtccatcag cacagcctac   240
atggagctga gcaggctgag atctgacgac acggccgtgt attactgtgc gagagggaga   300
tatggcagta gctggtacgg gggggtttgag tactgggggcc agggaaccct ggtcaccgtc   360
tcctca                                                                 366

<210> SEQ ID NO 146
<211> LENGTH: 122
<212> TYPE: PRT
<213> ORGANISM: Artificial Sequence
<220> FEATURE:
<223> OTHER INFORMATION: Synthetic

<400> SEQUENCE: 146

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly His
            20                  25                  30

Tyr Met Tyr Trp Met Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Asp Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Arg Tyr Gly Ser Ser Trp Tyr Gly Gly Phe Glu Tyr Trp
            100                 105                 110

Gly Gln Gly Thr Leu Val Thr Val Ser Ser
        115                 120
```

<210> SEQ ID NO 147
<211> LENGTH: 24
<212> TYPE: DNA
<213> ORGANISM: Artificial Sequence
<220> FEATURE:
<223> OTHER INFORMATION: Synthetic

<400> SEQUENCE: 147
ggatacacct tcaccggcca ctat                                      24

<210> SEQ ID NO 148
<211> LENGTH: 8
<212> TYPE: PRT
<213> ORGANISM: Artificial Sequence
<220> FEATURE:
<223> OTHER INFORMATION: Synthetic

<400> SEQUENCE: 148

```
Gly Tyr Thr Phe Thr Gly His Tyr
1               5
```

<210> SEQ ID NO 149
<211> LENGTH: 24
<212> TYPE: DNA
<213> ORGANISM: Artificial Sequence
<220> FEATURE:
<223> OTHER INFORMATION: Synthetic

<400> SEQUENCE: 149
atcaacccta acagtggtgg caca                                      24

<210> SEQ ID NO 150
<211> LENGTH: 8
<212> TYPE: PRT
<213> ORGANISM: Artificial Sequence
<220> FEATURE:
<223> OTHER INFORMATION: Synthetic

<400> SEQUENCE: 150

Ile Asn Pro Asn Ser Gly Gly Thr
1               5

<210> SEQ ID NO 151
<211> LENGTH: 45
<212> TYPE: DNA
<213> ORGANISM: Artificial Sequence
<220> FEATURE:
<223> OTHER INFORMATION: Synthetic

<400> SEQUENCE: 151
gcgagaggga gatatggcag tagctggtac gggggtttg agtac         45

<210> SEQ ID NO 152
<211> LENGTH: 15
<212> TYPE: PRT
<213> ORGANISM: Artificial Sequence
<220> FEATURE:
<223> OTHER INFORMATION: Synthetic

<400> SEQUENCE: 152

Ala Arg Gly Arg Tyr Gly Ser Ser Trp Tyr Gly Gly Phe Glu Tyr
1               5                   10                  15

<210> SEQ ID NO 153
<211> LENGTH: 321
<212> TYPE: DNA
<213> ORGANISM: Artificial Sequence
<220> FEATURE:
<223> OTHER INFORMATION: Synthetic

<400> SEQUENCE: 153
gacatccaga tgacccagtc tccatcttcc gtgtctgcat ctgttggaga cagagtcacc    60
atcacttgtc gggcgagtca gggtattacc agctggttag cctggtatca gcagaaacca   120
gggaaagccc ctaacctcct gatctatgct gcagccagtt tacaaagtgg ggtcccatca   180
aggttcagcg gcagtggatc tgggacggat ttcactctca ccatcagcag cctgcagcct   240
gaagacttta caacttacta ttgtcaacag gcttacagtc tccctctcac tttcggcgga   300
gggaccaagg tggagatcaa a                                              321

<210> SEQ ID NO 154
<211> LENGTH: 107
<212> TYPE: PRT
<213> ORGANISM: Artificial Sequence
<220> FEATURE:
<223> OTHER INFORMATION: Synthetic

<400> SEQUENCE: 154

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Thr Ser Trp
                20                  25                  30

Leu Ala Trp Tyr Gln Gln Lys Pro Gly Lys Ala Pro Asn Leu Leu Ile
            35                  40                  45

Tyr Ala Ala Ala Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Thr Thr Tyr Tyr Cys Gln Gln Ala Tyr Ser Leu Pro Leu 85                  90                  95

Thr Phe Gly Gly Gly Thr Lys Val Glu Ile Lys
            100                 105

<210> SEQ ID NO 155
<211> LENGTH: 18
<212> TYPE: DNA
<213> ORGANISM: Artificial Sequence
<220> FEATURE:
<223> OTHER INFORMATION: Synthetic

<400> SEQUENCE: 155
cagggtatta ccagctgg                                                    18

<210> SEQ ID NO 156
<211> LENGTH: 6
<212> TYPE: PRT
<213> ORGANISM: Artificial Sequence
<220> FEATURE:
<223> OTHER INFORMATION: Synthetic

<400> SEQUENCE: 156

Gln Gly Ile Thr Ser Trp
1               5

<210> SEQ ID NO 157
<211> LENGTH: 9
<212> TYPE: DNA
<213> ORGANISM: Artificial Sequence
<220> FEATURE:
<223> OTHER INFORMATION: Synthetic

<400> SEQUENCE: 157 gctgcagcc                                                               9

<210> SEQ ID NO 158
<211> LENGTH: 3
<212> TYPE: PRT
<213> ORGANISM: Artificial Sequence
<220> FEATURE:
<223> OTHER INFORMATION: Synthetic

<400> SEQUENCE: 158

Ala Ala Ala
1

<210> SEQ ID NO 159
<211> LENGTH: 27
<212> TYPE: DNA
<213> ORGANISM: Artificial Sequence
<220> FEATURE:
<223> OTHER INFORMATION: Synthetic

<400> SEQUENCE: 159
caacaggctt acagtctccc tctcact                                          27

<210> SEQ ID NO 160
<211> LENGTH: 9
<212> TYPE: PRT
<213> ORGANISM: Artificial Sequence
<220> FEATURE:
<223> OTHER INFORMATION: Synthetic

<400> SEQUENCE: 160

Gln Gln Ala Tyr Ser Leu Pro Leu Thr
1               5

<210> SEQ ID NO 161
<211> LENGTH: 366
<212> TYPE: DNA
<213> ORGANISM: Artificial Sequence
<220> FEATURE:
<223> OTHER INFORMATION: Synthetic

<400> SEQUENCE: 161

```
caggtgcagc tggtggagtc tgggggaggc gtggtccagc ctgggaggtc cctgagactc      60
tcctgtgcag cctctggatt caccttcagt agctatggct tgcactgggt ccgccagtct     120
ccaggcaagg ggctggaatg ggtggcactt atatcatatg acggaagtaa taaatactat     180
gcagactccg tgaagggccg attcaccatc tccagagaca attccaagaa cacgctgtat     240
ctgcaaatga acagcctgag acctgaggac acggctggat atttctgtgc gaaatcccta     300
tatacaacca gctggtacgg gggctttgac tattggggcc agggaaccct ggtcaccgtc     360
tcctca                                                                366
```

<210> SEQ ID NO 162
<211> LENGTH: 122
<212> TYPE: PRT
<213> ORGANISM: Artificial Sequence
<220> FEATURE:
<223> OTHER INFORMATION: Synthetic

<400> SEQUENCE: 162

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Leu His Trp Val Arg Gln Ser Pro Gly Lys Gly Leu Glu Trp Val
        35                  40                  45

Ala Leu Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Gly Tyr Phe Cys
                85                  90                  95

Ala Lys Ser Leu Tyr Thr Thr Ser Trp Tyr Gly Gly Phe Asp Tyr Trp
            100                 105                 110

Gly Gln Gly Thr Leu Val Thr Val Ser Ser
        115                 120
```

<210> SEQ ID NO 163
<211> LENGTH: 24
<212> TYPE: DNA
<213> ORGANISM: Artificial Sequence
<220> FEATURE:
<223> OTHER INFORMATION: Synthetic

<400> SEQUENCE: 163

```
ggattcacct tcagtagcta tggc                                             24
```

<210> SEQ ID NO 164
<211> LENGTH: 8
<212> TYPE: PRT
<213> ORGANISM: Artificial Sequence
<220> FEATURE:
<223> OTHER INFORMATION: Synthetic

<400> SEQUENCE: 164

Gly Phe Thr Phe Ser Ser Tyr Gly
1               5

<210> SEQ ID NO 165
<211> LENGTH: 24
<212> TYPE: DNA
<213> ORGANISM: Artificial Sequence
<220> FEATURE:
<223> OTHER INFORMATION: Synthetic

<400> SEQUENCE: 165
atatcatatg acggaagtaa taaa                                              24

<210> SEQ ID NO 166
<211> LENGTH: 8
<212> TYPE: PRT
<213> ORGANISM: Artificial Sequence
<220> FEATURE:
<223> OTHER INFORMATION: Synthetic

<400> SEQUENCE: 166

Ile Ser Tyr Asp Gly Ser Asn Lys
1               5

<210> SEQ ID NO 167
<211> LENGTH: 45
<212> TYPE: DNA
<213> ORGANISM: Artificial Sequence
<220> FEATURE:
<223> OTHER INFORMATION: Synthetic

<400> SEQUENCE: 167
gcgaaatccc tatatacaac cagctggtac gggggctttg actat                       45

<210> SEQ ID NO 168
<211> LENGTH: 15
<212> TYPE: PRT
<213> ORGANISM: Artificial Sequence
<220> FEATURE:
<223> OTHER INFORMATION: Synthetic

<400> SEQUENCE: 168

Ala Lys Ser Leu Tyr Thr Thr Ser Trp Tyr Gly Gly Phe Asp Tyr
1               5                   10                  15

<210> SEQ ID NO 169
<211> LENGTH: 321
<212> TYPE: DNA
<213> ORGANISM: Artificial Sequence
<220> FEATURE:
<223> OTHER INFORMATION: Synthetic

<400> SEQUENCE: 169
gacatccaga tgacccagtc tccatcttcc gtgtctgcat ctgtaggaga cagagtcacc        60
atcacttgtc gggcgagtca gggtattaga agctggttag cctggtatca gcaaaaacca       120
gggaaagccc ctaacctcct gatctatgct gcgtccagtt tgcaaagtgg ggtcccatca       180
aggttcagcg gcagtggatc tgggacagat ttcactctca ccatcagcag cctgcagcct       240
gaagattttg caacttacta ttgtcaacag gctaacagtt tccctcccac tttcggccct       300
gggaccaaag tggatatcaa a                                                 321

<210> SEQ ID NO 170

```
<211> LENGTH: 107
<212> TYPE: PRT
<213> ORGANISM: Artificial Sequence
<220> FEATURE:
<223> OTHER INFORMATION: Synthetic

<400> SEQUENCE: 170

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Arg Ser Trp
            20                  25                  30

Leu Ala Trp Tyr Gln Gln Lys Pro Gly Lys Ala Pro Asn Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Pro
                85                  90                  95

Thr Phe Gly Pro Gly Thr Lys Val Asp Ile Lys
            100                 105

<210> SEQ ID NO 171
<211> LENGTH: 18
<212> TYPE: DNA
<213> ORGANISM: Artificial Sequence
<220> FEATURE:
<223> OTHER INFORMATION: Synthetic

<400> SEQUENCE: 171
cagggtatta gaagctgg                                                        18

<210> SEQ ID NO 172
<211> LENGTH: 6
<212> TYPE: PRT
<213> ORGANISM: Artificial Sequence
<220> FEATURE:
<223> OTHER INFORMATION: Synthetic

<400> SEQUENCE: 172

Gln Gly Ile Arg Ser Trp
1               5

<210> SEQ ID NO 173
<211> LENGTH: 9
<212> TYPE: DNA
<213> ORGANISM: Artificial Sequence
<220> FEATURE:
<223> OTHER INFORMATION: Synthetic

<400> SEQUENCE: 173 gctgcgtcc                                                                   9

<210> SEQ ID NO 174
<211> LENGTH: 3
<212> TYPE: PRT
<213> ORGANISM: Artificial Sequence
<220> FEATURE:
<223> OTHER INFORMATION: Synthetic

<400> SEQUENCE: 174

Ala Ala Ser
1
```

<210> SEQ ID NO 175
<211> LENGTH: 27
<212> TYPE: DNA
<213> ORGANISM: Artificial Sequence
<220> FEATURE:
<223> OTHER INFORMATION: Synthetic

<400> SEQUENCE: 175
caacaggcta acagtttccc tcccact                                          27

<210> SEQ ID NO 176
<211> LENGTH: 9
<212> TYPE: PRT
<213> ORGANISM: Artificial Sequence
<220> FEATURE:
<223> OTHER INFORMATION: Synthetic

<400> SEQUENCE: 176

Gln Gln Ala Asn Ser Phe Pro Pro Thr
1               5

<210> SEQ ID NO 177
<211> LENGTH: 366
<212> TYPE: DNA
<213> ORGANISM: Artificial Sequence
<220> FEATURE:
<223> OTHER INFORMATION: Synthetic

<400> SEQUENCE: 177
gaggtgcagc tggtggagtc tgggggaggc ttggtacagc ctggggggtc cctgagactc      60
tcctgtgcag cctctgggtt caccttcagc aactatgcca tgacctgggt ccgccaggct     120
ccagggaagg ggctggagtg gtctcaact atcagtggca gtggtgataa cacatactac      180
gcagactccg tgcagggccg gttcaccatc tccagaggcc attccaagaa cacgctgtat     240
ctgcaaatga acagcctgag agccgaggac acggccgtat attactgtgc gaaacctacg    300
tatagcagaa gctggtacgg tgcttttgat ttctggggcc aagggacaat ggtcaccgtc    360
tcttca                                                                366

<210> SEQ ID NO 178
<211> LENGTH: 122
<212> TYPE: PRT
<213> ORGANISM: Artificial Sequence
<220> FEATURE:
<223> OTHER INFORMATION: Synthetic

<400> SEQUENCE: 178

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Thr Trp Val Arg Gln Ala Pro Gly Lys Gly Leu Glu Trp Val
        35                  40                  45

Ser Thr Ile Ser Gly Ser Gly Asp Asn Thr Tyr Tyr Ala Asp Ser Val
    50                  55                  60

Gln Gly Arg Phe Thr Ile Ser Arg Gly His Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Thr Tyr Ser Arg Ser Trp Tyr Gly Ala Phe Asp Phe Trp
            100                 105                 110

Gly Gln Gly Thr Met Val Thr Val Ser Ser
        115                 120

<210> SEQ ID NO 179
<211> LENGTH: 24
<212> TYPE: DNA
<213> ORGANISM: Artificial Sequence
<220> FEATURE:
<223> OTHER INFORMATION: Synthetic

<400> SEQUENCE: 179
gggttcacct tcagcaacta tgcc                                          24

<210> SEQ ID NO 180
<211> LENGTH: 8
<212> TYPE: PRT
<213> ORGANISM: Artificial Sequence
<220> FEATURE:
<223> OTHER INFORMATION: Synthetic

<400> SEQUENCE: 180

Gly Phe Thr Phe Ser Asn Tyr Ala
1               5

<210> SEQ ID NO 181
<211> LENGTH: 24
<212> TYPE: DNA
<213> ORGANISM: Artificial Sequence
<220> FEATURE:
<223> OTHER INFORMATION: Synthetic

<400> SEQUENCE: 181
atcagtggca gtggtgataa caca                                          24

<210> SEQ ID NO 182
<211> LENGTH: 8
<212> TYPE: PRT
<213> ORGANISM: Artificial Sequence
<220> FEATURE:
<223> OTHER INFORMATION: Synthetic

<400> SEQUENCE: 182

Ile Ser Gly Ser Gly Asp Asn Thr
1               5

<210> SEQ ID NO 183
<211> LENGTH: 45
<212> TYPE: DNA
<213> ORGANISM: Artificial Sequence
<220> FEATURE:
<223> OTHER INFORMATION: Synthetic

<400> SEQUENCE: 183
gcgaaaccta cgtatagcag aagctggtac ggtgcttttg atttc                   45

<210> SEQ ID NO 184
<211> LENGTH: 15
<212> TYPE: PRT
<213> ORGANISM: Artificial Sequence
<220> FEATURE:
<223> OTHER INFORMATION: Synthetic

<400> SEQUENCE: 184

Ala Lys Pro Thr Tyr Ser Arg Ser Trp Tyr Gly Ala Phe Asp Phe
1               5                   10                  15

<210> SEQ ID NO 185
<211> LENGTH: 321
<212> TYPE: DNA
<213> ORGANISM: Artificial Sequence
<220> FEATURE:
<223> OTHER INFORMATION: Synthetic

<400> SEQUENCE: 185

```
gacatccaga tgacccagtc tccatcctcc gtgtctgcat ctgtaggaga cagagtcacc     60
atcacttgtc gggcgagtca gggtattagc agctggttag cctggtatca gcagaaaccg    120
gggaaagccc ctcaactcct gatctatgct gcatccagat tgcaaagtgg ggtcccatca    180
aggttctggg gcagtggatc tgggacagat ttcactctca ccatcagcag cctgcagcct    240
gaagattttg caacttacta ttgtcaacag gctaacaatt tcccattcac tttcggccct    300
gggaccaaag tggatatcaa a                                              321
```

<210> SEQ ID NO 186
<211> LENGTH: 107
<212> TYPE: PRT
<213> ORGANISM: Artificial Sequence
<220> FEATURE:
<223> OTHER INFORMATION: Synthetic

<400> SEQUENCE: 186

Asp Ile Gln Met Thr Gln Ser Pro Ser Ser Val Ser Ala Ser Val Gly
1               5                   10                  15
Asp Arg Val Thr Ile Thr Cys Arg Ala Ser Gln Gly Ile Ser Ser Trp
            20                  25                  30
Leu Ala Trp Tyr Gln Gln Lys Pro Gly Lys Ala Pro Gln Leu Leu Ile
        35                  40                  45
Tyr Ala Ala Ser Arg Leu Gln Ser Gly Val Pro Ser Arg Phe Trp Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Ala Asn Asn Phe Pro Phe
                85                  90                  95
Thr Phe Gly Pro Gly Thr Lys Val Asp Ile Lys
            100                 105

<210> SEQ ID NO 187
<211> LENGTH: 18
<212> TYPE: DNA
<213> ORGANISM: Artificial Sequence
<220> FEATURE:
<223> OTHER INFORMATION: Synthetic

<400> SEQUENCE: 187

```
cagggtatta gcagctgg                                                   18
```

<210> SEQ ID NO 188
<211> LENGTH: 6
<212> TYPE: PRT
<213> ORGANISM: Artificial Sequence
<220> FEATURE:
<223> OTHER INFORMATION: Synthetic

<400> SEQUENCE: 188

Gln Gly Ile Ser Ser Trp
1               5

```
<210> SEQ ID NO 189
<211> LENGTH: 9
<212> TYPE: DNA
<213> ORGANISM: Artificial Sequence
<220> FEATURE:
<223> OTHER INFORMATION: Synthetic

<400> SEQUENCE: 189 gctgcatcc                                                                  9

<210> SEQ ID NO 190
<211> LENGTH: 3
<212> TYPE: PRT
<213> ORGANISM: Artificial Sequence
<220> FEATURE:
<223> OTHER INFORMATION: Synthetic

<400> SEQUENCE: 190

Ala Ala Ser
1

<210> SEQ ID NO 191
<211> LENGTH: 27
<212> TYPE: DNA
<213> ORGANISM: Artificial Sequence
<220> FEATURE:
<223> OTHER INFORMATION: Synthetic

<400> SEQUENCE: 191
caacaggcta acaatttccc attcact                                             27

<210> SEQ ID NO 192
<211> LENGTH: 9
<212> TYPE: PRT
<213> ORGANISM: Artificial Sequence
<220> FEATURE:
<223> OTHER INFORMATION: Synthetic

<400> SEQUENCE: 192

Gln Gln Ala Asn Asn Phe Pro Phe Thr
1               5

<210> SEQ ID NO 193
<211> LENGTH: 366
<212> TYPE: DNA
<213> ORGANISM: Artificial Sequence
<220> FEATURE:
<223> OTHER INFORMATION: Synthetic

<400> SEQUENCE: 193
caggttcagc tggtgcagtc tggagctgag gtgaagaagc ctggggcctc agtgaaggtc          60
tcctgcaagg cttctggtta ccctttacc agttatggta tcagctgggt gcgacaggcc         120
cctggacaag gccttgagtg gatgggatgg atccgcgctt acaatggtta cacaaactat         180
gcacagaagt ttcagggcag agtcaccatg accacagaca catccacgaa caccgcctac         240
atggagctga ggaccctgaa ttctgacgat acggccgttt attactgtgc gagagatcga         300
tatagtggga gcttccacgg taactttgac tactggggcc agggaaccct ggtcaccgtc         360
tcctca                                                                   366

<210> SEQ ID NO 194
<211> LENGTH: 122
<212> TYPE: PRT
<213> ORGANISM: Artificial Sequence
<220> FEATURE:
```

<223> OTHER INFORMATION: Synthetic

<400> SEQUENCE: 194

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Arg Ala Tyr Asn Gly Tyr Thr Asn Tyr Ala Gln Lys Phe
    50                  55                  60

Gln Gly Arg Val Thr Met Thr Thr Asp Thr Ser Thr Asn Thr Ala Tyr
65                  70                  75                  80

Met Glu Leu Arg Thr Leu Asn Ser Asp Asp Thr Ala Val Tyr Tyr Cys
                85                  90                  95

Ala Arg Asp Arg Tyr Ser Gly Ser Phe His Gly Asn Phe Asp Tyr Trp
            100                 105                 110

Gly Gln Gly Thr Leu Val Thr Val Ser Ser
        115                 120

<210> SEQ ID NO 195
<211> LENGTH: 24
<212> TYPE: DNA
<213> ORGANISM: Artificial Sequence
<220> FEATURE:
<223> OTHER INFORMATION: Synthetic

<400> SEQUENCE: 195
ggttacacct ttaccagtta tggt                                          24

<210> SEQ ID NO 196
<211> LENGTH: 8
<212> TYPE: PRT
<213> ORGANISM: Artificial Sequence
<220> FEATURE:
<223> OTHER INFORMATION: Synthetic

<400> SEQUENCE: 196

Gly Tyr Thr Phe Thr Ser Tyr Gly
1               5

<210> SEQ ID NO 197
<211> LENGTH: 24
<212> TYPE: DNA
<213> ORGANISM: Artificial Sequence
<220> FEATURE:
<223> OTHER INFORMATION: Synthetic

<400> SEQUENCE: 197
atccgcgctt acaatggtta caca                                          24

<210> SEQ ID NO 198
<211> LENGTH: 8
<212> TYPE: PRT
<213> ORGANISM: Artificial Sequence
<220> FEATURE:
<223> OTHER INFORMATION: Synthetic

<400> SEQUENCE: 198

Ile Arg Ala Tyr Asn Gly Tyr Thr
1               5

```
<210> SEQ ID NO 199
<211> LENGTH: 45
<212> TYPE: DNA
<213> ORGANISM: Artificial Sequence
<220> FEATURE:
<223> OTHER INFORMATION: Synthetic

<400> SEQUENCE: 199
gcgagagatc gatatagtgg gagcttccac ggtaactttg actac            45

<210> SEQ ID NO 200
<211> LENGTH: 15
<212> TYPE: PRT
<213> ORGANISM: Artificial Sequence
<220> FEATURE:
<223> OTHER INFORMATION: Synthetic

<400> SEQUENCE: 200

Ala Arg Asp Arg Tyr Ser Gly Ser Phe His Gly Asn Phe Asp Tyr
1               5                   10                  15

<210> SEQ ID NO 201
<211> LENGTH: 321
<212> TYPE: DNA
<213> ORGANISM: Artificial Sequence
<220> FEATURE:
<223> OTHER INFORMATION: Synthetic

<400> SEQUENCE: 201
gacatccaga tgacccagtc tccatcttcc gtgtctgcgt ctgtaggaga cagagtgacc    60
atcacttgtc gggcgagtca gggtattttc agctggttag cctggtatca gcagaaacca   120
gggaaagccc ctaaggtcct aatctatgct gcatccaatt tggaaagtgg ggtcccatca   180
aggttcagcg gcagtggatc tgggacagat ttcactctca ccatcagcag cctgcagcct   240
gaagattttg caacttacta ttgtcaacag gctaacagtt taccgctcac tttcggcgga   300
gggaccaagg tggagatcaa a                                             321

<210> SEQ ID NO 202
<211> LENGTH: 107
<212> TYPE: PRT
<213> ORGANISM: Artificial Sequence
<220> FEATURE:
<223> OTHER INFORMATION: Synthetic

<400> SEQUENCE: 202

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Phe Ser Trp
                20                  25                  30

Leu Ala Trp Tyr Gln Gln Lys Pro Gly Lys Ala Pro Lys Val Leu Ile
            35                  40                  45

Tyr Ala Ala Ser Asn Leu Glu Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Leu Pro Leu
                85                  90                  95

Thr Phe Gly Gly Gly Thr Lys Val Glu Ile Lys
            100                 105

<210> SEQ ID NO 203
```

```
<211> LENGTH: 18
<212> TYPE: DNA
<213> ORGANISM: Artificial Sequence
<220> FEATURE:
<223> OTHER INFORMATION: Synthetic

<400> SEQUENCE: 203
cagggtattt tcagctgg                                                   18

<210> SEQ ID NO 204
<211> LENGTH: 6
<212> TYPE: PRT
<213> ORGANISM: Artificial Sequence
<220> FEATURE:
<223> OTHER INFORMATION: Synthetic

<400> SEQUENCE: 204

Gln Gly Ile Phe Ser Trp
1               5

<210> SEQ ID NO 205
<211> LENGTH: 9
<212> TYPE: DNA
<213> ORGANISM: Artificial Sequence
<220> FEATURE:
<223> OTHER INFORMATION: Synthetic

<400> SEQUENCE: 205 gctgcatcc                                                              9

<210> SEQ ID NO 206
<211> LENGTH: 3
<212> TYPE: PRT
<213> ORGANISM: Artificial Sequence
<220> FEATURE:
<223> OTHER INFORMATION: Synthetic

<400> SEQUENCE: 206

Ala Ala Ser
1

<210> SEQ ID NO 207
<211> LENGTH: 27
<212> TYPE: DNA
<213> ORGANISM: Artificial Sequence
<220> FEATURE:
<223> OTHER INFORMATION: Synthetic

<400> SEQUENCE: 207
caacaggcta acagtttacc gctcact                                         27

<210> SEQ ID NO 208
<211> LENGTH: 9
<212> TYPE: PRT
<213> ORGANISM: Artificial Sequence
<220> FEATURE:
<223> OTHER INFORMATION: Synthetic

<400> SEQUENCE: 208

Gln Gln Ala Asn Ser Leu Pro Leu Thr
1               5

<210> SEQ ID NO 209
<211> LENGTH: 366
<212> TYPE: DNA
<213> ORGANISM: Artificial Sequence
<220> FEATURE:
```

<223> OTHER INFORMATION: Synthetic

<400> SEQUENCE: 209

```
gaggtgcagc tggtggagtc tgggggaggc ttggtccagc ctggggggtc cctgagactc      60
tcctgtgcag cctctggatt caccttcagt acctattcta tgcactgggt ccgccaggct     120
ccagggaagg gactggaata tgtttcaact attaataata tggggatac cacatattat      180
gcagactctg tgaagggcag attcaccatc tccagagaca attccaagaa cacgctgtat     240
cttcaactgg gcagcctgag acctgaggac atggctgtgt attactgtgc gagacagacg     300
tataccagca gctggtacgg ggggttcgac tcctggggcc agggaaccct ggtcaccgtc     360
tcctca                                                                366
```

<210> SEQ ID NO 210
<211> LENGTH: 122
<212> TYPE: PRT
<213> ORGANISM: Artificial Sequence
<220> FEATURE:
<223> OTHER INFORMATION: Synthetic

<400> SEQUENCE: 210

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Thr Tyr
            20                  25                  30

Ser Met His Trp Val Arg Gln Ala Pro Gly Lys Gly Leu Glu Tyr Val
        35                  40                  45

Ser Thr Ile Asn Asn Asn Gly Asp Thr Thr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Leu Gly Ser Leu Arg Pro Glu Asp Met Ala Val Tyr Tyr Cys
                85                  90                  95

Ala Arg Gln Thr Tyr Thr Ser Ser Trp Tyr Gly Gly Phe Asp Ser Trp
            100                 105                 110

Gly Gln Gly Thr Leu Val Thr Val Ser Ser
        115                 120
```

<210> SEQ ID NO 211
<211> LENGTH: 24
<212> TYPE: DNA
<213> ORGANISM: Artificial Sequence
<220> FEATURE:
<223> OTHER INFORMATION: Synthetic

<400> SEQUENCE: 211

```
ggattcacct tcagtaccta ttct                                             24
```

<210> SEQ ID NO 212
<211> LENGTH: 8
<212> TYPE: PRT
<213> ORGANISM: Artificial Sequence
<220> FEATURE:
<223> OTHER INFORMATION: Synthetic

<400> SEQUENCE: 212

```
Gly Phe Thr Phe Ser Thr Tyr Ser
 1               5
```

<210> SEQ ID NO 213

<211> LENGTH: 24
<212> TYPE: DNA
<213> ORGANISM: Artificial Sequence
<220> FEATURE:
<223> OTHER INFORMATION: Synthetic

<400> SEQUENCE: 213
attaataata atgggatac caca                                          24

<210> SEQ ID NO 214
<211> LENGTH: 8
<212> TYPE: PRT
<213> ORGANISM: Artificial Sequence
<220> FEATURE:
<223> OTHER INFORMATION: Synthetic

<400> SEQUENCE: 214

Ile Asn Asn Asn Gly Asp Thr Thr
1               5

<210> SEQ ID NO 215
<211> LENGTH: 45
<212> TYPE: DNA
<213> ORGANISM: Artificial Sequence
<220> FEATURE:
<223> OTHER INFORMATION: Synthetic

<400> SEQUENCE: 215
gcgagacaga cgtataccag cagctggtac gggggggttcg actcc                 45

<210> SEQ ID NO 216
<211> LENGTH: 15
<212> TYPE: PRT
<213> ORGANISM: Artificial Sequence
<220> FEATURE:
<223> OTHER INFORMATION: Synthetic

<400> SEQUENCE: 216

Ala Arg Gln Thr Tyr Thr Ser Ser Trp Tyr Gly Gly Phe Asp Ser
1               5                   10                  15

<210> SEQ ID NO 217
<211> LENGTH: 321
<212> TYPE: DNA
<213> ORGANISM: Artificial Sequence
<220> FEATURE:
<223> OTHER INFORMATION: Synthetic

<400> SEQUENCE: 217
gacatccaga tgacccagtc tccatcttcc gtgtctgcat ctgtaggcga cagagtcacc      60
atcacttgtc gggcgagtca gggtattacc agctggttag cctggtatca gcagaaacca     120
gggaaagccc ctaaactcct gatctatgct gcatccaatt tgcaaagtgg ggtcccatca     180
aggttcagcg gcagtggatc tgggacagat tcactctca ccatcaccag cctgcagcct     240
gaggattttg caacttacta ttgtcaacag gctaacagtc tcccattcac tttcggccct     300
gggaccaaag tggatatcaa a                                              321

<210> SEQ ID NO 218
<211> LENGTH: 107
<212> TYPE: PRT
<213> ORGANISM: Artificial Sequence
<220> FEATURE:
<223> OTHER INFORMATION: Synthetic

<400> SEQUENCE: 218

-continued

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Thr Ser Trp
            20                  25                  30

Leu Ala Trp Tyr Gln Lys Pro Gly Lys Ala Pro Lys Leu Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Asp Phe Thr Leu Thr Ile Thr Ser Leu Gln Pro
65                  70                  75                  80

Glu Asp Phe Ala Thr Tyr Tyr Cys Gln Gln Ala Asn Ser Leu Pro Phe
                85                  90                  95

Thr Phe Gly Pro Gly Thr Lys Val Asp Ile Lys
            100                 105
```

<210> SEQ ID NO 219
<211> LENGTH: 18
<212> TYPE: DNA
<213> ORGANISM: Artificial Sequence
<220> FEATURE:
<223> OTHER INFORMATION: Synthetic

<400> SEQUENCE: 219
cagggtatta ccagctgg                                              18

<210> SEQ ID NO 220
<211> LENGTH: 6
<212> TYPE: PRT
<213> ORGANISM: Artificial Sequence
<220> FEATURE:
<223> OTHER INFORMATION: Synthetic

<400> SEQUENCE: 220

```
Gln Gly Ile Thr Ser Trp
1               5
```

<210> SEQ ID NO 221
<211> LENGTH: 9
<212> TYPE: DNA
<213> ORGANISM: Artificial Sequence
<220> FEATURE:
<223> OTHER INFORMATION: Synthetic

<400> SEQUENCE: 221 gctgcatcc                                                        9

<210> SEQ ID NO 222
<211> LENGTH: 3
<212> TYPE: PRT
<213> ORGANISM: Artificial Sequence
<220> FEATURE:
<223> OTHER INFORMATION: Synthetic

<400> SEQUENCE: 222

```
Ala Ala Ser
1
```

<210> SEQ ID NO 223
<211> LENGTH: 27
<212> TYPE: DNA
<213> ORGANISM: Artificial Sequence
<220> FEATURE:
<223> OTHER INFORMATION: Synthetic

<400> SEQUENCE: 223
caacaggcta acagtctccc attcact    27

<210> SEQ ID NO 224
<211> LENGTH: 9
<212> TYPE: PRT
<213> ORGANISM: Artificial Sequence
<220> FEATURE:
<223> OTHER INFORMATION: Synthetic

<400> SEQUENCE: 224

Gln Gln Ala Asn Ser Leu Pro Phe Thr
1               5

<210> SEQ ID NO 225
<211> LENGTH: 366
<212> TYPE: DNA
<213> ORGANISM: Artificial Sequence
<220> FEATURE:
<223> OTHER INFORMATION: Synthetic

<400> SEQUENCE: 225
gaggtgcagc tggtggagtc tgggggaggc ttggtacagc ctggggggtc cctgagactc    60
tcctgtgcag cctctggatt caccttagc agctatgcca tgagctgggt ccgccaggct   120
ccagggaagg gctggagtg gtctcagct attagtggta gtggtggcag cacatactac   180
gcagactccg tgaagggccg gttcaccatc tccagagaca attccaagaa ctcgctgtat   240
ctgcaattga acagcctgag agccgaggac acggccgtat attactgtgc gaagacgctg   300
tatactacca gctggtacgg gggcttccag cactgggggcc agggcaccct ggtcactgtc   360
tcctca    366

<210> SEQ ID NO 226
<211> LENGTH: 122
<212> TYPE: PRT
<213> ORGANISM: Artificial Sequence
<220> FEATURE:
<223> OTHER INFORMATION: Synthetic

<400> SEQUENCE: 226

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Ser Leu Tyr
65                  70                  75                  80

Leu Gln Leu Asn Ser Leu Arg Ala Glu Asp Thr Ala Val Tyr Tyr Cys
                85                  90                  95

Ala Lys Thr Leu Tyr Thr Thr Ser Trp Tyr Gly Gly Phe Gln His Trp
            100                 105                 110

Gly Gln Gly Thr Leu Val Thr Val Ser Ser
        115                 120

<210> SEQ ID NO 227
<211> LENGTH: 24

<210> SEQ ID NO 227
<211> LENGTH: 24
<212> TYPE: DNA
<213> ORGANISM: Artificial Sequence
<220> FEATURE:
<223> OTHER INFORMATION: Synthetic

<400> SEQUENCE: 227
ggattcaccc ttagcagcta tgcc                                           24

<210> SEQ ID NO 228
<211> LENGTH: 8
<212> TYPE: PRT
<213> ORGANISM: Artificial Sequence
<220> FEATURE:
<223> OTHER INFORMATION: Synthetic

<400> SEQUENCE: 228

Gly Phe Thr Leu Ser Ser Tyr Ala
1               5

<210> SEQ ID NO 229
<211> LENGTH: 24
<212> TYPE: DNA
<213> ORGANISM: Artificial Sequence
<220> FEATURE:
<223> OTHER INFORMATION: Synthetic

<400> SEQUENCE: 229
attagtggta gtggtggcag caca                                           24

<210> SEQ ID NO 230
<211> LENGTH: 8
<212> TYPE: PRT
<213> ORGANISM: Artificial Sequence
<220> FEATURE:
<223> OTHER INFORMATION: Synthetic

<400> SEQUENCE: 230

Ile Ser Gly Ser Gly Gly Ser Thr
1               5

<210> SEQ ID NO 231
<211> LENGTH: 45
<212> TYPE: DNA
<213> ORGANISM: Artificial Sequence
<220> FEATURE:
<223> OTHER INFORMATION: Synthetic

<400> SEQUENCE: 231
gcgaagacgc tgtatactac cagctggtac gggggcttcc agcac                    45

<210> SEQ ID NO 232
<211> LENGTH: 15
<212> TYPE: PRT
<213> ORGANISM: Artificial Sequence
<220> FEATURE:
<223> OTHER INFORMATION: Synthetic

<400> SEQUENCE: 232

Ala Lys Thr Leu Tyr Thr Thr Ser Trp Tyr Gly Gly Phe Gln His
1               5                   10                  15

<210> SEQ ID NO 233
<211> LENGTH: 321
<212> TYPE: DNA
<213> ORGANISM: Artificial Sequence
<220> FEATURE:
<223> OTHER INFORMATION: Synthetic

<400> SEQUENCE: 233

```
gacatccaga tgacccagtc tccatcttcc gtgtctgcat ctataggaga cagagtcacc      60
atcacttgtc gggcgagtca gggaatcagc agttggttag cctggtatca gcagaaacca     120
gggaaagtcc ctaagctcct gatctatgct gcgtcctctt tgcaaagtgg gttcccatca     180
aggttcagcg gcagtggatc tgggacagat tcactctcac catcagtag cctgcagccc      240
gaagattttg caacttacta ttgtcaacag actcacagtt tcccgtggac ggtcggccaa     300
gggaccaagg tggaaatcaa a                                               321
```

<210> SEQ ID NO 234
<211> LENGTH: 107
<212> TYPE: PRT
<213> ORGANISM: Artificial Sequence
<220> FEATURE:
<223> OTHER INFORMATION: Synthetic

<400> SEQUENCE: 234

```
Asp Ile Gln Met Thr Gln Ser Pro Ser Ser Val Ser Ala Ser Ile Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Val Pro Lys Leu Leu Ile
        35                  40                  45

Tyr Ala Ala Ser Ser Leu Gln Ser Gly Phe Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr His Ser Phe Pro Trp
                85                  90                  95

Thr Val Gly Gln Gly Thr Lys Val Glu Ile Lys
            100                 105
```

<210> SEQ ID NO 235
<211> LENGTH: 18
<212> TYPE: DNA
<213> ORGANISM: Artificial Sequence
<220> FEATURE:
<223> OTHER INFORMATION: Synthetic

<400> SEQUENCE: 235

```
cagggaatca gcagttgg                                                    18
```

<210> SEQ ID NO 236
<211> LENGTH: 6
<212> TYPE: PRT
<213> ORGANISM: Artificial Sequence
<220> FEATURE:
<223> OTHER INFORMATION: Synthetic

<400> SEQUENCE: 236

```
Gln Gly Ile Ser Ser Trp
1               5
```

<210> SEQ ID NO 237
<211> LENGTH: 9
<212> TYPE: DNA
<213> ORGANISM: Artificial Sequence
<220> FEATURE:
<223> OTHER INFORMATION: Synthetic

```
<400> SEQUENCE: 237 gctgcgtcc                                                                9

<210> SEQ ID NO 238
<211> LENGTH: 3
<212> TYPE: PRT
<213> ORGANISM: Artificial Sequence
<220> FEATURE:
<223> OTHER INFORMATION: Synthetic

<400> SEQUENCE: 238

Ala Ala Ser
1

<210> SEQ ID NO 239
<211> LENGTH: 24
<212> TYPE: DNA
<213> ORGANISM: Artificial Sequence
<220> FEATURE:
<223> OTHER INFORMATION: Synthetic

<400> SEQUENCE: 239
caacagactc acagtttccc gtgg                                              24

<210> SEQ ID NO 240
<211> LENGTH: 8
<212> TYPE: PRT
<213> ORGANISM: Artificial Sequence
<220> FEATURE:
<223> OTHER INFORMATION: Synthetic

<400> SEQUENCE: 240

Gln Gln Thr His Ser Phe Pro Trp
1               5

<210> SEQ ID NO 241
<211> LENGTH: 366
<212> TYPE: DNA
<213> ORGANISM: Artificial Sequence
<220> FEATURE:
<223> OTHER INFORMATION: Synthetic

<400> SEQUENCE: 241
gaggtgcagc tggtggagtc tgggggaggc ttggtacagc ctgggggtc cctgagactc        60 tcctgtgcag cctctggatt caccttagg agctatttca tgacctgggt ccgccaggtt      120
ccagggaagg ggctggaggg ggtctcagct attagtggca ttagtggtgg cacatactac     180
acagactccg ttaagggccg gttcaccatc tccagagaca attccaagaa cacgctgttt     240
ctgcaaatga acagcctgag agccgaggac acggccgtat atttctgtgc gagaacggtg     300
tatagtagta gttactacgg gggcttccag cactgggggcc agggcaccct ggtcaccgtc    360
tcctca                                                                366

<210> SEQ ID NO 242
<211> LENGTH: 122
<212> TYPE: PRT
<213> ORGANISM: Artificial Sequence
<220> FEATURE:
<223> OTHER INFORMATION: Synthetic

<400> SEQUENCE: 242

Glu Val Gln Leu Val Glu Ser Gly Gly Gly Leu Val Gln Pro Gly Gly
1               5                   10                  15
```

-continued

```
Ser Leu Arg Leu Ser Cys Ala Ala Ser Gly Phe Thr Leu Arg Ser Tyr
            20                  25                  30

Phe Met Thr Trp Val Arg Gln Val Pro Gly Lys Gly Leu Glu Gly Val
        35                  40                  45

Ser Ala Ile Ser Gly Ile Ser Gly Gly Thr Tyr Tyr Thr Asp Ser Val
50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Phe Cys
                85                  90                  95

Ala Arg Thr Val Tyr Ser Ser Tyr Tyr Gly Gly Phe Gln His Trp
            100                 105                 110

Gly Gln Gly Thr Leu Val Thr Val Ser Ser
        115                 120

<210> SEQ ID NO 243
<211> LENGTH: 24
<212> TYPE: DNA
<213> ORGANISM: Artificial Sequence
<220> FEATURE:
<223> OTHER INFORMATION: Synthetic

<400> SEQUENCE: 243
ggattcaccc ttaggagcta tttc                                           24

<210> SEQ ID NO 244
<211> LENGTH: 8
<212> TYPE: PRT
<213> ORGANISM: Artificial Sequence
<220> FEATURE:
<223> OTHER INFORMATION: Synthetic

<400> SEQUENCE: 244

Gly Phe Thr Leu Arg Ser Tyr Phe
1               5

<210> SEQ ID NO 245
<211> LENGTH: 24
<212> TYPE: DNA
<213> ORGANISM: Artificial Sequence
<220> FEATURE:
<223> OTHER INFORMATION: Synthetic

<400> SEQUENCE: 245
attagtggca ttagtggtgg caca                                           24

<210> SEQ ID NO 246
<211> LENGTH: 8
<212> TYPE: PRT
<213> ORGANISM: Artificial Sequence
<220> FEATURE:
<223> OTHER INFORMATION: Synthetic

<400> SEQUENCE: 246

Ile Ser Gly Ile Ser Gly Gly Thr
1               5

<210> SEQ ID NO 247
<211> LENGTH: 45
<212> TYPE: DNA
<213> ORGANISM: Artificial Sequence
<220> FEATURE:
<223> OTHER INFORMATION: Synthetic
```

-continued

<400> SEQUENCE: 247
gcgagaacgg tgtatagtag tagttactac gggggcttcc agcac    45

<210> SEQ ID NO 248
<211> LENGTH: 15
<212> TYPE: PRT
<213> ORGANISM: Artificial Sequence
<220> FEATURE:
<223> OTHER INFORMATION: Synthetic

<400> SEQUENCE: 248

Ala Arg Thr Val Tyr Ser Ser Ser Tyr Tyr Gly Gly Phe Gln His
1               5                   10                  15

<210> SEQ ID NO 249
<211> LENGTH: 321
<212> TYPE: DNA
<213> ORGANISM: Artificial Sequence
<220> FEATURE:
<223> OTHER INFORMATION: Synthetic

<400> SEQUENCE: 249
gacatccaga tgacccagtc tccatcttcc gtgtctgtat ctgtaggaga cagagtcacc     60
atcacttgtc gggcgagtca gggtattagc agttggttag cctggtatca gcagaaacca    120
gggaaagccc ctaagctcct gatctatgtt gcatccagtt tacaaagtgg ggtcccatca    180
aggttcagcg gcagtggatc tgggacagat ttcactctca ccatcagcag cctgcagcct    240
gaagattttg caacttacta ttgtcaacag actaacagtt ccctctcac tttcggcgga    300 gggaccaagg tggagatcaa a                                              321

<210> SEQ ID NO 250
<211> LENGTH: 107
<212> TYPE: PRT
<213> ORGANISM: Artificial Sequence
<220> FEATURE:
<223> OTHER INFORMATION: Synthetic

<400> SEQUENCE: 250

Asp Ile Gln Met Thr Gln Ser Pro Ser Ser Val Ser Val Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Val Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Asn Ser Phe Pro Leu
                85                  90                  95

Thr Phe Gly Gly Gly Thr Lys Val Glu Ile Lys
            100                 105

<210> SEQ ID NO 251
<211> LENGTH: 18
<212> TYPE: DNA
<213> ORGANISM: Artificial Sequence
<220> FEATURE:
<223> OTHER INFORMATION: Synthetic

<400> SEQUENCE: 251

```
cagggtatta gcagttgg                                                  18

<210> SEQ ID NO 252
<211> LENGTH: 6
<212> TYPE: PRT
<213> ORGANISM: Artificial Sequence
<220> FEATURE:
<223> OTHER INFORMATION: Synthetic

<400> SEQUENCE: 252

Gln Gly Ile Ser Ser Trp
1               5

<210> SEQ ID NO 253
<211> LENGTH: 9
<212> TYPE: DNA
<213> ORGANISM: Artificial Sequence
<220> FEATURE:
<223> OTHER INFORMATION: Synthetic

<400> SEQUENCE: 253 gttgcatcc                                                             9

<210> SEQ ID NO 254
<211> LENGTH: 3
<212> TYPE: PRT
<213> ORGANISM: Artificial Sequence
<220> FEATURE:
<223> OTHER INFORMATION: Synthetic

<400> SEQUENCE: 254

Val Ala Ser
1

<210> SEQ ID NO 255
<211> LENGTH: 27
<212> TYPE: DNA
<213> ORGANISM: Artificial Sequence
<220> FEATURE:
<223> OTHER INFORMATION: Synthetic

<400> SEQUENCE: 255
caacagacta acagtttccc tctcact                                        27

<210> SEQ ID NO 256
<211> LENGTH: 9
<212> TYPE: PRT
<213> ORGANISM: Artificial Sequence
<220> FEATURE:
<223> OTHER INFORMATION: Synthetic

<400> SEQUENCE: 256

Gln Gln Thr Asn Ser Phe Pro Leu Thr
1               5

<210> SEQ ID NO 257
<211> LENGTH: 366
<212> TYPE: DNA
<213> ORGANISM: Artificial Sequence
<220> FEATURE:
<223> OTHER INFORMATION: Synthetic

<400> SEQUENCE: 257
gaggtgcagc tggtggagtc tgggggaggc ttggtacagc ctggggggtc cctgagactc    60
tcctgtgcag cctctggatt cacccttagg agttatgtca tgactgggt ccgccagggt   120
```

```
ccagggaagg ggctggaggg ggtctcaggt attagtggca gtagtggtgg cacatactac    180
acagactccg tgaagggccg gttcaccatc tccagagaca attccaagaa cacgctgttt    240
ctgcaaatga acagcctgag agccgaggac acggccgtat atttctgtgc gagatcggtg    300
tatagtacca cctggtacgg gggcttccag cactggggcc agggcaccct ggtcaccgtc    360
tcctca                                                               366
```

<210> SEQ ID NO 258
<211> LENGTH: 122
<212> TYPE: PRT
<213> ORGANISM: Artificial Sequence
<220> FEATURE:
<223> OTHER INFORMATION: Synthetic

<400> SEQUENCE: 258

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Arg Ser Tyr
            20                  25                  30

Val Met Tyr Trp Val Arg Gln Gly Pro Gly Lys Gly Leu Glu Gly Val
        35                  40                  45

Ser Gly Ile Ser Gly Ser Gly Gly Thr Tyr Tyr Thr Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Phe Cys
                85                  90                  95

Ala Arg Ser Val Tyr Ser Thr Thr Trp Tyr Gly Gly Phe Gln His Trp
            100                 105                 110

Gly Gln Gly Thr Leu Val Thr Val Ser Ser
        115                 120

<210> SEQ ID NO 259
<211> LENGTH: 24
<212> TYPE: DNA
<213> ORGANISM: Artificial Sequence
<220> FEATURE:
<223> OTHER INFORMATION: Synthetic

<400> SEQUENCE: 259
ggattcaccc ttaggagtta tgtc                                            24

<210> SEQ ID NO 260
<211> LENGTH: 8
<212> TYPE: PRT
<213> ORGANISM: Artificial Sequence
<220> FEATURE:
<223> OTHER INFORMATION: Synthetic

<400> SEQUENCE: 260

Gly Phe Thr Leu Arg Ser Tyr Val
1               5

<210> SEQ ID NO 261
<211> LENGTH: 24
<212> TYPE: DNA
<213> ORGANISM: Artificial Sequence
<220> FEATURE:
<223> OTHER INFORMATION: Synthetic

<400> SEQUENCE: 261

```
attagtggca gtagtggtgg caca                                          24

<210> SEQ ID NO 262
<211> LENGTH: 8
<212> TYPE: PRT
<213> ORGANISM: Artificial Sequence
<220> FEATURE:
<223> OTHER INFORMATION: Synthetic

<400> SEQUENCE: 262

Ile Ser Gly Ser Ser Gly Gly Thr
1               5

<210> SEQ ID NO 263
<211> LENGTH: 45
<212> TYPE: DNA
<213> ORGANISM: Artificial Sequence
<220> FEATURE:
<223> OTHER INFORMATION: Synthetic

<400> SEQUENCE: 263
gcgagatcgg tgtatagtac cacctggtac gggggcttcc agcac                   45

<210> SEQ ID NO 264
<211> LENGTH: 15
<212> TYPE: PRT
<213> ORGANISM: Artificial Sequence
<220> FEATURE:
<223> OTHER INFORMATION: Synthetic

<400> SEQUENCE: 264

Ala Arg Ser Val Tyr Ser Thr Thr Trp Tyr Gly Gly Phe Gln His
1               5                   10                  15

<210> SEQ ID NO 265
<211> LENGTH: 321
<212> TYPE: DNA
<213> ORGANISM: Artificial Sequence
<220> FEATURE:
<223> OTHER INFORMATION: Synthetic

<400> SEQUENCE: 265
gacatccaga tgacccagtc tccatcttcc gtgtctgtat ctgtgggaga cagagtcacc    60
atcacttgtc gggcgagtca ggttattagc agttggttag cctggtatca gctgaaacca   120
gggaaagccc ctaaactcct gatctatgct gcatccagtt acaaagtggg gtcccatca    180 aggttcagcg gcagtggatc tgggacagat ttcactctca ccatcagcgg cctgcagcct   240
gaagattttg cagtttacta ttgtcaacag actaacagtt tccctctcac tttcggcgga   300
gggaccaagg tggagatcaa a                                             321

<210> SEQ ID NO 266
<211> LENGTH: 107
<212> TYPE: PRT
<213> ORGANISM: Artificial Sequence
<220> FEATURE:
<223> OTHER INFORMATION: Synthetic

<400> SEQUENCE: 266

Asp Ile Gln Met Thr Gln Ser Pro Ser Ser Val Ser Val Ser Val Gly
1               5                   10                  15

Asp Arg Val Thr Ile Thr Cys Arg Ala Ser Gln Val Ile Ser Ser Trp
            20                  25                  30
```

```
Leu Ala Trp Tyr Gln Leu Lys Pro Gly Lys Ala Pro Lys Leu Leu Ile
            35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Gly Leu Gln Pro
 65                  70                  75                  80

Glu Asp Phe Ala Val Tyr Tyr Cys Gln Gln Thr Asn Ser Phe Pro Leu
                 85                  90                  95

Thr Phe Gly Gly Gly Thr Lys Val Glu Ile Lys
            100                 105
```

<210> SEQ ID NO 267
<211> LENGTH: 18
<212> TYPE: DNA
<213> ORGANISM: Artificial Sequence
<220> FEATURE:
<223> OTHER INFORMATION: Synthetic

<400> SEQUENCE: 267
caggttatta gcagttgg                                               18

<210> SEQ ID NO 268
<211> LENGTH: 6
<212> TYPE: PRT
<213> ORGANISM: Artificial Sequence
<220> FEATURE:
<223> OTHER INFORMATION: Synthetic

<400> SEQUENCE: 268

```
Gln Val Ile Ser Ser Trp
1               5
```

<210> SEQ ID NO 269
<211> LENGTH: 9
<212> TYPE: DNA
<213> ORGANISM: Artificial Sequence
<220> FEATURE:
<223> OTHER INFORMATION: Synthetic

<400> SEQUENCE: 269 gctgcatcc                                                          9

<210> SEQ ID NO 270
<211> LENGTH: 3
<212> TYPE: PRT
<213> ORGANISM: Artificial Sequence
<220> FEATURE:
<223> OTHER INFORMATION: Synthetic

<400> SEQUENCE: 270

```
Ala Ala Ser
1
```

<210> SEQ ID NO 271
<211> LENGTH: 27
<212> TYPE: DNA
<213> ORGANISM: Artificial Sequence
<220> FEATURE:
<223> OTHER INFORMATION: Synthetic

<400> SEQUENCE: 271
caacagacta acagtttccc tctcact                                     27

<210> SEQ ID NO 272

<210> SEQ ID NO 272
<211> LENGTH: 9
<212> TYPE: PRT
<213> ORGANISM: Artificial Sequence
<220> FEATURE:
<223> OTHER INFORMATION: Synthetic

<400> SEQUENCE: 272

Gln Gln Thr Asn Ser Phe Pro Leu Thr
1               5

<210> SEQ ID NO 273
<211> LENGTH: 366
<212> TYPE: DNA
<213> ORGANISM: Artificial Sequence
<220> FEATURE:
<223> OTHER INFORMATION: Synthetic

<400> SEQUENCE: 273
gaggtgcagc tggtggagtc tgggggaaac ttggaacagc ctggggggtc ccttagactc      60
tcctgtacag cctctggatt cacctttagc agatctgcca tgaactgggt ccgccgggct     120
ccagggaagg ggctggagtg ggtctcagga attagtggta gtggtggtcg aacatactac     180
gcagactccg tgaagggccg gttcaccatc tccagagaca attccaagaa tacgctatat     240
ctgcaaatga acagcctgag cgccgaggac acggccgcat attactgtgc gaaagattcg     300
tatactacca gttggtacgg aggtatggac gtctggggcc acgggaccac ggtcaccgtc     360
tcctca                                                                366

<210> SEQ ID NO 274
<211> LENGTH: 122
<212> TYPE: PRT
<213> ORGANISM: Artificial Sequence
<220> FEATURE:
<223> OTHER INFORMATION: Synthetic

<400> SEQUENCE: 274

Glu Val Gln Leu Val Glu Ser Gly Gly Asn Leu Glu Gln Pro Gly Gly
1               5                  10                  15

Ser Leu Arg Leu Ser Cys Thr Ala Ser Gly Phe Thr Phe Ser Arg Ser
            20                  25                  30

Ala Met Asn Trp Val Arg Arg Ala Pro Gly Lys Gly Leu Glu Trp Val
        35                  40                  45

Ser Gly Ile Ser Gly Ser Gly Gly Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Ser Ala Glu Asp Thr Ala Ala Tyr Tyr Cys
                85                  90                  95

Ala Lys Asp Ser Tyr Thr Thr Ser Trp Tyr Gly Gly Met Asp Val Trp
            100                 105                 110

Gly His Gly Thr Thr Val Thr Val Ser Ser
        115                 120

<210> SEQ ID NO 275
<211> LENGTH: 24
<212> TYPE: DNA
<213> ORGANISM: Artificial Sequence
<220> FEATURE:
<223> OTHER INFORMATION: Synthetic

<400> SEQUENCE: 275

```
ggattcacct ttagcagatc tgcc                                            24
```

<210> SEQ ID NO 276
<211> LENGTH: 8
<212> TYPE: PRT
<213> ORGANISM: Artificial Sequence
<220> FEATURE:
<223> OTHER INFORMATION: Synthetic

<400> SEQUENCE: 276

```
Gly Phe Thr Phe Ser Arg Ser Ala
1               5
```

<210> SEQ ID NO 277
<211> LENGTH: 24
<212> TYPE: DNA
<213> ORGANISM: Artificial Sequence
<220> FEATURE:
<223> OTHER INFORMATION: Synthetic

<400> SEQUENCE: 277

```
attagtggta gtggtggtcg aaca                                            24
```

<210> SEQ ID NO 278
<211> LENGTH: 8
<212> TYPE: PRT
<213> ORGANISM: Artificial Sequence
<220> FEATURE:
<223> OTHER INFORMATION: Synthetic

<400> SEQUENCE: 278

```
Ile Ser Gly Ser Gly Gly Arg Thr
1               5
```

<210> SEQ ID NO 279
<211> LENGTH: 45
<212> TYPE: DNA
<213> ORGANISM: Artificial Sequence
<220> FEATURE:
<223> OTHER INFORMATION: Synthetic

<400> SEQUENCE: 279

```
gcgaaagatt cgtatactac cagttggtac ggaggtatgg acgtc              45
```

<210> SEQ ID NO 280
<211> LENGTH: 15
<212> TYPE: PRT
<213> ORGANISM: Artificial Sequence
<220> FEATURE:
<223> OTHER INFORMATION: Synthetic

<400> SEQUENCE: 280

```
Ala Lys Asp Ser Tyr Thr Thr Ser Trp Tyr Gly Gly Met Asp Val
1               5                   10                  15
```

<210> SEQ ID NO 281
<211> LENGTH: 321
<212> TYPE: DNA
<213> ORGANISM: Artificial Sequence
<220> FEATURE:
<223> OTHER INFORMATION: Synthetic

<400> SEQUENCE: 281

```
gacatccaga tgacccagtc tccatcttcc gtgtctgcat ctgtaggaga cagagtcacc    60
atcacttgtc gggcgagtca gggtattttc agctggttag cctggtatca gcagaaacca   120
```

```
ggaaaagccc ctaagctcct gatctatgct gcttccagtt tacaaagtgg ggtcccatca    180
agattcagcg gcagtggatc tgggacagat ttcactctca ccatcagcag cctgcagcct    240
gaggattttg caatttacta ttgtcaacag gctaacagtg tcccgatcac cttcggccaa    300
gggacacgac tggagattaa a                                              321
```

<210> SEQ ID NO 282
<211> LENGTH: 107
<212> TYPE: PRT
<213> ORGANISM: Artificial Sequence
<220> FEATURE:
<223> OTHER INFORMATION: Synthetic

<400> SEQUENCE: 282

```
Asp Ile Gln Met Thr Gln Ser Pro Ser Val Ser Ala Ser Val Gly
1               5                   10                  15

Asp Arg Val Thr Ile Thr Cys Arg Ala Ser Gln Gly Ile Phe Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Ile Tyr Tyr Cys Gln Gln Ala Asn Ser Val Pro Ile
                85                  90                  95

Thr Phe Gly Gln Gly Thr Arg Leu Glu Ile Lys
            100                 105
```

<210> SEQ ID NO 283
<211> LENGTH: 18
<212> TYPE: DNA
<213> ORGANISM: Artificial Sequence
<220> FEATURE:
<223> OTHER INFORMATION: Synthetic

<400> SEQUENCE: 283

```
cagggtattt tcagctgg                                                   18
```

<210> SEQ ID NO 284
<211> LENGTH: 6
<212> TYPE: PRT
<213> ORGANISM: Artificial Sequence
<220> FEATURE:
<223> OTHER INFORMATION: Synthetic

<400> SEQUENCE: 284

```
Gln Gly Ile Phe Ser Trp
1               5
```

<210> SEQ ID NO 285
<211> LENGTH: 9
<212> TYPE: DNA
<213> ORGANISM: Artificial Sequence
<220> FEATURE:
<223> OTHER INFORMATION: Synthetic

<400> SEQUENCE: 285

```
gctgcttcc                                                              9
```

<210> SEQ ID NO 286
<211> LENGTH: 3

```
<212> TYPE: PRT
<213> ORGANISM: Artificial Sequence
<220> FEATURE:
<223> OTHER INFORMATION: Synthetic

<400> SEQUENCE: 286

Ala Ala Ser
1

<210> SEQ ID NO 287
<211> LENGTH: 27
<212> TYPE: DNA
<213> ORGANISM: Artificial Sequence
<220> FEATURE:
<223> OTHER INFORMATION: Synthetic

<400> SEQUENCE: 287
caacaggcta acagtgtccc gatcacc                                            27

<210> SEQ ID NO 288
<211> LENGTH: 9
<212> TYPE: PRT
<213> ORGANISM: Artificial Sequence
<220> FEATURE:
<223> OTHER INFORMATION: Synthetic

<400> SEQUENCE: 288

Gln Gln Ala Asn Ser Val Pro Ile Thr
1               5

<210> SEQ ID NO 289
<211> LENGTH: 366
<212> TYPE: DNA
<213> ORGANISM: Artificial Sequence
<220> FEATURE:
<223> OTHER INFORMATION: Synthetic

<400> SEQUENCE: 289
gaggtgcagc tggtggagtc tgggggaggc ttggtacagc ctggggggtc cctgagactc         60
tcctgttcag cctctggatt cacctttagc agctatgcca tgaactgggt ccgccaggct        120
ccagggaagg ggctggagtg ggtcaccgct attagtggag tggtggtgg cacatactac         180 gcagactccg tgaagggccg gttcaccatc tccagacaca attccaagaa ctcgctgttt        240
ctgcaattga acagcctgag agccgaggac acggccgtgt attactgtgc gaaacaaacg        300
tataccagca gctggtacgg tggctttgat atctggggcc aggggacaat ggtcaccgtc        360
tcttca                                                                   366

<210> SEQ ID NO 290
<211> LENGTH: 122
<212> TYPE: PRT
<213> ORGANISM: Artificial Sequence
<220> FEATURE:
<223> OTHER INFORMATION: Synthetic

<400> SEQUENCE: 290

Glu Val Gln Leu Val Glu Ser Gly Gly Gly Leu Val Gln Pro Gly Gly
1               5                   10                  15

Ser Leu Arg Leu Ser Cys Ser Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Thr Ala Ile Ser Gly Ser Gly Gly Gly Thr Tyr Tyr Ala Asp Ser Val
```

```
                50                  55                  60
Lys Gly Arg Phe Thr Ile Ser Arg Asp Asn Ser Lys Asn Ser Leu Phe
 65                  70                  75                  80

Leu Gln Leu Asn Ser Leu Arg Ala Glu Asp Thr Ala Val Tyr Tyr Cys
                 85                  90                  95

Ala Lys Gln Thr Tyr Thr Ser Ser Trp Tyr Gly Phe Asp Ile Trp
            100                 105                 110

Gly Gln Gly Thr Met Val Thr Val Ser Ser
        115                 120
```

<210> SEQ ID NO 291
<211> LENGTH: 24
<212> TYPE: DNA
<213> ORGANISM: Artificial Sequence
<220> FEATURE:
<223> OTHER INFORMATION: Synthetic

<400> SEQUENCE: 291
ggattcacct ttagcagcta tgcc                                           24

<210> SEQ ID NO 292
<211> LENGTH: 8
<212> TYPE: PRT
<213> ORGANISM: Artificial Sequence
<220> FEATURE:
<223> OTHER INFORMATION: Synthetic

<400> SEQUENCE: 292

```
Gly Phe Thr Phe Ser Ser Tyr Ala
 1               5
```

<210> SEQ ID NO 293
<211> LENGTH: 24
<212> TYPE: DNA
<213> ORGANISM: Artificial Sequence
<220> FEATURE:
<223> OTHER INFORMATION: Synthetic

<400> SEQUENCE: 293
attagtggca gtggtggtgg caca                                           24

<210> SEQ ID NO 294
<211> LENGTH: 8
<212> TYPE: PRT
<213> ORGANISM: Artificial Sequence
<220> FEATURE:
<223> OTHER INFORMATION: Synthetic

<400> SEQUENCE: 294

```
Ile Ser Gly Ser Gly Gly Gly Thr
 1               5
```

<210> SEQ ID NO 295
<211> LENGTH: 45
<212> TYPE: DNA
<213> ORGANISM: Artificial Sequence
<220> FEATURE:
<223> OTHER INFORMATION: Synthetic

<400> SEQUENCE: 295
gcgaaacaaa cgtataccag cagctggtac ggtggctttg atatc                    45

<210> SEQ ID NO 296
<211> LENGTH: 15

```
<212> TYPE: PRT
<213> ORGANISM: Artificial Sequence
<220> FEATURE:
<223> OTHER INFORMATION: Synthetic

<400> SEQUENCE: 296

Ala Lys Gln Thr Tyr Thr Ser Ser Trp Tyr Gly Gly Phe Asp Ile
1               5                   10                  15

<210> SEQ ID NO 297
<211> LENGTH: 321
<212> TYPE: DNA
<213> ORGANISM: Artificial Sequence
<220> FEATURE:
<223> OTHER INFORMATION: Synthetic

<400> SEQUENCE: 297
gacatccaga tgacccagtc gccatcttcc gtgtccgcgt ctgtaggaga cagagtcacc      60
atcacttgtc gggcgagtca gggttttagt tcctggttag cctggtatca gcagatacca    120
gggaaagccc ccaagctcct gatctatgct gcatcaaggt tgcaaagtgg ggtcccatcc    180
aggttccgcg gcagtggatc tgggacagat tcactctcac catcagcag cctgcagcct     240 gaggattttg caacttacta ttgtcaacag gctaacagtt tcccgctcac tttcggcgga    300
gggaccaagg tggagatcaa a                                              321

<210> SEQ ID NO 298
<211> LENGTH: 107
<212> TYPE: PRT
<213> ORGANISM: Artificial Sequence
<220> FEATURE:
<223> OTHER INFORMATION: Synthetic

<400> SEQUENCE: 298

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Phe Ser Ser Trp
            20                  25                  30

Leu Ala Trp Tyr Gln Gln Ile Pro Gly Lys Ala Pro Lys Leu Leu Ile
        35                  40                  45

Tyr Ala Ala Ser Arg Leu Gln Ser Gly Val Pro Ser Arg Phe Arg Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Leu
                85                  90                  95

Thr Phe Gly Gly Gly Thr Lys Val Glu Ile Lys
            100                 105

<210> SEQ ID NO 299
<211> LENGTH: 18
<212> TYPE: DNA
<213> ORGANISM: Artificial Sequence
<220> FEATURE:
<223> OTHER INFORMATION: Synthetic

<400> SEQUENCE: 299
cagggtttta gttcctgg                                                   18

<210> SEQ ID NO 300
<211> LENGTH: 6
<212> TYPE: PRT
```

```
<213> ORGANISM: Artificial Sequence
<220> FEATURE:
<223> OTHER INFORMATION: Synthetic

<400> SEQUENCE: 300

Gln Gly Phe Ser Ser Trp
1               5

<210> SEQ ID NO 301
<211> LENGTH: 9
<212> TYPE: DNA
<213> ORGANISM: Artificial Sequence
<220> FEATURE:
<223> OTHER INFORMATION: Synthetic

<400> SEQUENCE: 301 gctgcatca                                                                9

<210> SEQ ID NO 302
<211> LENGTH: 3
<212> TYPE: PRT
<213> ORGANISM: Artificial Sequence
<220> FEATURE:
<223> OTHER INFORMATION: Synthetic

<400> SEQUENCE: 302

Ala Ala Ser
1

<210> SEQ ID NO 303
<211> LENGTH: 27
<212> TYPE: DNA
<213> ORGANISM: Artificial Sequence
<220> FEATURE:
<223> OTHER INFORMATION: Synthetic

<400> SEQUENCE: 303
caacaggcta acagtttccc gctcact                                           27

<210> SEQ ID NO 304
<211> LENGTH: 9
<212> TYPE: PRT
<213> ORGANISM: Artificial Sequence
<220> FEATURE:
<223> OTHER INFORMATION: Synthetic

<400> SEQUENCE: 304

Gln Gln Ala Asn Ser Phe Pro Leu Thr
1               5

<210> SEQ ID NO 305
<211> LENGTH: 167
<212> TYPE: PRT
<213> ORGANISM: Artificial Sequence
<220> FEATURE:
<223> OTHER INFORMATION: Synthetic

<400> SEQUENCE: 305

Ser Ile Thr Gly Ile Ser Pro Ile Thr Glu Ser Leu Ala Ser Leu Ser
1               5                   10                  15

Thr Tyr Asn Asp Gln Ser Ile Thr Phe Ala Leu Glu Asp Glu Ser Tyr
            20                  25                  30

Glu Ile Tyr Val Glu Asp Leu Lys Lys Asp Lys Lys Lys Asp Lys Val
        35                  40                  45

Leu Leu Ser Tyr Tyr Glu Ser Gln His Pro Ser Ser Glu Ser Gly Asp
```

```
                    50                  55                  60
Gly Val Asp Gly Lys Met Leu Met Val Thr Leu Ser Pro Thr Lys Asp
 65                  70                  75                  80

Phe Trp Leu Gln Ala Asn Asn Lys Glu His Ser Val Glu Leu His Lys
                     85                  90                  95

Cys Glu Lys Pro Leu Pro Asp Gln Ala Phe Phe Val Leu His Asn Arg
                100                 105                 110

Ser Phe Asn Cys Val Ser Phe Glu Cys Lys Thr Asp Pro Gly Val Phe
            115                 120                 125

Ile Gly Val Lys Asp Asn His Leu Ala Leu Ile Lys Val Asp Tyr Ser
        130                 135                 140

Glu Asn Leu Gly Ser Glu Asn Ile Leu Phe Lys Leu Ser Glu Ile Leu
145                 150                 155                 160

Glu His His His His His His
                165

<210> SEQ ID NO 306
<211> LENGTH: 167
<212> TYPE: PRT
<213> ORGANISM: Artificial Sequence
<220> FEATURE:
<223> OTHER INFORMATION: Synthetic

<400> SEQUENCE: 306

Ser Ile Thr Gly Ile Ser Pro Ile Thr Glu Ser Leu Ala Ser Leu Ser
  1               5                  10                  15

Thr Tyr Asn Asp Gln Ser Ile Thr Phe Ala Leu Glu Asp Glu Ser Tyr
             20                  25                  30

Glu Ile Tyr Val Glu Asp Leu Lys Lys Asp Lys Lys Asp Lys Val
         35                  40                  45

Leu Leu Ser Tyr Tyr Glu Ser Gln His Pro Ser Ser Glu Ser Gly Asp
     50                  55                  60

Gly Val Asp Gly Lys Met Leu Met Val Thr Leu Ser Pro Thr Lys Asp
 65                  70                  75                  80

Phe Trp Leu Gln Ala Asn Asn Lys Glu His Ser Val Glu Leu His Lys
                     85                  90                  95

Cys Glu Lys Pro Leu Pro Asp Gln Ala Phe Phe Val Leu His Asn Arg
                100                 105                 110

Ser Phe Asn Cys Val Ser Phe Glu Cys Lys Thr Asp Pro Gly Val Phe
            115                 120                 125

Ile Gly Val Lys Asp Asn His Leu Ala Leu Ile Lys Val Asp Tyr Ser
        130                 135                 140

Glu Asn Leu Gly Ser Glu Asn Ile Leu Phe Lys Leu Ser Glu Ile Leu
145                 150                 155                 160

Glu His His His His His His
                165

<210> SEQ ID NO 307
<211> LENGTH: 354
<212> TYPE: DNA
<213> ORGANISM: Artificial Sequence
<220> FEATURE:
<223> OTHER INFORMATION: Synthetic

<400> SEQUENCE: 307
caggtcacct tgaaggagtc tggtcctgtg ctggtgaaac ccacagagag cctcacgctg      60
acctgctccg tctctggatt ctcactcagt aatgttagaa tgggtgtgag ctggatccgt     120
```

```
cagtccccag ggaaggccct ggagtggctt gcacacattt tttcgaatga cgaaaaatcc    180
tacaccacat ctctgaagac caggctcacc atctccaagg acacctccag aagccaggtg    240
gtccttacca tgaccgacat ggaccctggg gacacagcca tatattactg tgcacggata    300
cggaatttgg cctttaatta ctggggccag ggaaccctgg tcaccgtctc ctca          354
```

```
<210> SEQ ID NO 308
<211> LENGTH: 118
<212> TYPE: PRT
<213> ORGANISM: Artificial Sequence
<220> FEATURE:
<223> OTHER INFORMATION: Synthetic

<400> SEQUENCE: 308
```

Gln Val Thr Leu Lys Glu Ser Gly Pro Val Leu Val Lys Pro Thr Glu
1               5                   10                  15

Ser Leu Thr Leu Thr Cys Ser Val Ser Gly Phe Ser Leu Ser Asn Val
            20                  25                  30

Arg Met Gly Val Ser Trp Ile Arg Gln Ser Pro Gly Lys Ala Leu Glu
        35                  40                  45

Trp Leu Ala His Ile Phe Ser Asn Asp Glu Lys Ser Tyr Thr Thr Ser
    50                  55                  60

Leu Lys Thr Arg Leu Thr Ile Ser Lys Asp Thr Ser Arg Ser Gln Val
65                  70                  75                  80

Val Leu Thr Met Thr Asp Met Asp Pro Gly Asp Thr Ala Thr Tyr Tyr
                85                  90                  95

Cys Ala Arg Ile Arg Asn Leu Ala Phe Asn Tyr Trp Gly Gln Gly Thr
            100                 105                 110

Leu Val Thr Val Ser Ser
        115

```
<210> SEQ ID NO 309
<211> LENGTH: 30
<212> TYPE: DNA
<213> ORGANISM: Artificial Sequence
<220> FEATURE:
<223> OTHER INFORMATION: Synthetic

<400> SEQUENCE: 309
ggattctcac tcagtaatgt tagaatgggt                                      30
```

```
<210> SEQ ID NO 310
<211> LENGTH: 10
<212> TYPE: PRT
<213> ORGANISM: Artificial Sequence
<220> FEATURE:
<223> OTHER INFORMATION: Synthetic

<400> SEQUENCE: 310
```

Gly Phe Ser Leu Ser Asn Val Arg Met Gly
1               5                   10

```
<210> SEQ ID NO 311
<211> LENGTH: 21
<212> TYPE: DNA
<213> ORGANISM: Artificial Sequence
<220> FEATURE:
<223> OTHER INFORMATION: Synthetic

<400> SEQUENCE: 311
attttttcga atgacgaaaa a                                               21
```

```
<210> SEQ ID NO 312
<211> LENGTH: 7
<212> TYPE: PRT
<213> ORGANISM: Artificial Sequence
<220> FEATURE:
<223> OTHER INFORMATION: Synthetic

<400> SEQUENCE: 312

Ile Phe Ser Asn Asp Glu Lys
1               5

<210> SEQ ID NO 313
<211> LENGTH: 30
<212> TYPE: DNA
<213> ORGANISM: Artificial Sequence
<220> FEATURE:
<223> OTHER INFORMATION: Synthetic

<400> SEQUENCE: 313
gcacggatac ggaatttggc ctttaattac                                    30

<210> SEQ ID NO 314
<211> LENGTH: 10
<212> TYPE: PRT
<213> ORGANISM: Artificial Sequence
<220> FEATURE:
<223> OTHER INFORMATION: Synthetic

<400> SEQUENCE: 314

Ala Arg Ile Arg Asn Leu Ala Phe Asn Tyr
1               5                   10

<210> SEQ ID NO 315
<211> LENGTH: 339
<212> TYPE: DNA
<213> ORGANISM: Artificial Sequence
<220> FEATURE:
<223> OTHER INFORMATION: Synthetic

<400> SEQUENCE: 315
gacttcgtga tgacccagtc tccagactcc ctggctgtgt ctctgggcga gagggccacc    60
atcaactgca gtccagccag agtgtgttta cacaggtcca gcaataagaa ctacttagct   120
tggtatcagc agaagccagg acagcctcct aacctgctca tttactgggc atctacccgg   180
gaatccgggg tccctgaccg attcagtggc agcgggtctg ggacagattt cactctcacc   240
atcagcagcc tgcaggctga agatgtggca gtttattact gtcagcaata ttatggtact   300
ctatttactt tcggccctgg gaccaaagtg gatatcaaa                          339

<210> SEQ ID NO 316
<211> LENGTH: 113
<212> TYPE: PRT
<213> ORGANISM: Artificial Sequence
<220> FEATURE:
<223> OTHER INFORMATION: Synthetic

<400> SEQUENCE: 316

Asp Phe Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu His Arg
            20                  25                  30

Ser Ser Asn Lys Asn Tyr Leu Ala Trp Tyr Gln Gln Lys Pro Gly Gln
        35                  40                  45
```

```
Pro Pro Asn Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Gly Thr Leu Phe Thr Phe Gly Pro Gly Thr Lys Val Asp Ile
            100                 105                 110

Lys

<210> SEQ ID NO 317
<211> LENGTH: 36
<212> TYPE: DNA
<213> ORGANISM: Artificial Sequence
<220> FEATURE:
<223> OTHER INFORMATION: Synthetic

<400> SEQUENCE: 317
cagagtgtgt tacacaggtc cagcaataag aactac                         36

<210> SEQ ID NO 318
<211> LENGTH: 12
<212> TYPE: PRT
<213> ORGANISM: Artificial Sequence
<220> FEATURE:
<223> OTHER INFORMATION: Synthetic

<400> SEQUENCE: 318

Gln Ser Val Leu His Arg Ser Ser Asn Lys Asn Tyr
1               5                   10

<210> SEQ ID NO 319
<211> LENGTH: 9
<212> TYPE: DNA
<213> ORGANISM: Artificial Sequence
<220> FEATURE:
<223> OTHER INFORMATION: Synthetic

<400> SEQUENCE: 319 tgggcatct                                                        9

<210> SEQ ID NO 320
<211> LENGTH: 3
<212> TYPE: PRT
<213> ORGANISM: Artificial Sequence
<220> FEATURE:
<223> OTHER INFORMATION: Synthetic

<400> SEQUENCE: 320

Trp Ala Ser
1

<210> SEQ ID NO 321
<211> LENGTH: 27
<212> TYPE: DNA
<213> ORGANISM: Artificial Sequence
<220> FEATURE:
<223> OTHER INFORMATION: Synthetic

<400> SEQUENCE: 321
cagcaatatt atggtactct atttact                                   27

<210> SEQ ID NO 322
```

```
<211> LENGTH: 9
<212> TYPE: PRT
<213> ORGANISM: Artificial Sequence
<220> FEATURE:
<223> OTHER INFORMATION: Synthetic

<400> SEQUENCE: 322

Gln Gln Tyr Tyr Gly Thr Leu Phe Thr
1               5

<210> SEQ ID NO 323
<211> LENGTH: 338
<212> TYPE: PRT
<213> ORGANISM: Artificial Sequence
<220> FEATURE:
<223> OTHER INFORMATION: synthetic
      Amino acids 1-310: Human ST2 (K19-S328 of
      accession number NP_057316.3)
      Amino acids 311-338: Myc-Myc-hexahistidine tag

<400> SEQUENCE: 323

Lys Phe Ser Lys Gln Ser Trp Gly Leu Glu Asn Glu Ala Leu Ile Val
1               5                   10                  15

Arg Cys Pro Arg Gln Gly Lys Pro Ser Tyr Thr Val Asp Trp Tyr Tyr
            20                  25                  30

Ser Gln Thr Asn Lys Ser Ile Pro Thr Gln Glu Arg Asn Arg Val Phe
        35                  40                  45

Ala Ser Gly Gln Leu Leu Lys Phe Leu Pro Ala Ala Val Ala Asp Ser
    50                  55                  60

Gly Ile Tyr Thr Cys Ile Val Arg Ser Pro Thr Phe Asn Arg Thr Gly
65                  70                  75                  80

Tyr Ala Asn Val Thr Ile Tyr Lys Lys Gln Ser Asp Cys Asn Val Pro
                85                  90                  95

Asp Tyr Leu Met Tyr Ser Thr Val Ser Gly Ser Glu Lys Asn Ser Lys
            100                 105                 110

Ile Tyr Cys Pro Thr Ile Asp Leu Tyr Asn Trp Thr Ala Pro Leu Glu
        115                 120                 125

Trp Phe Lys Asn Cys Gln Ala Leu Gln Gly Ser Arg Tyr Arg Ala His
    130                 135                 140

Lys Ser Phe Leu Val Ile Asp Asn Val Met Thr Glu Asp Ala Gly Asp
145                 150                 155                 160

Tyr Thr Cys Lys Phe Ile His Asn Glu Asn Gly Ala Asn Tyr Ser Val
                165                 170                 175

Thr Ala Thr Arg Ser Phe Thr Val Lys Asp Glu Gln Gly Phe Ser Leu
            180                 185                 190

Phe Pro Val Ile Gly Ala Pro Ala Gln Asn Glu Ile Lys Glu Val Glu
        195                 200                 205

Ile Gly Lys Asn Ala Asn Leu Thr Cys Ser Ala Cys Phe Gly Lys Gly
    210                 215                 220

Thr Gln Phe Leu Ala Ala Val Leu Trp Gln Leu Asn Gly Thr Lys Ile
225                 230                 235                 240

Thr Asp Phe Gly Glu Pro Arg Ile Gln Gln Glu Glu Gly Gln Asn Gln
                245                 250                 255

Ser Phe Ser Asn Gly Leu Ala Cys Leu Asp Met Val Leu Arg Ile Ala
            260                 265                 270

Asp Val Lys Glu Glu Asp Leu Leu Leu Gln Tyr Asp Cys Leu Ala Leu
        275                 280                 285

Asn Leu His Gly Leu Arg Arg His Thr Val Arg Leu Ser Arg Lys Asn
```

```
     290                 295                 300
Pro Ile Asp His His Ser Glu Gln Lys Leu Ile Ser Glu Glu Asp Leu
305                 310                 315                 320

Gly Gly Glu Gln Lys Leu Ile Ser Glu Glu Asp Leu His His His His
                325                 330                 335

His His
```